United States Patent
Vertikov

(10) Patent No.: US 9,439,570 B2
(45) Date of Patent: Sep. 13, 2016

(54) TISSUE IMAGING AND IMAGE GUIDANCE IN LUMINAL ANATOMIC STRUCTURES AND BODY CAVITIES

(71) Applicant: LX Medical, Inc., Westwood, MA (US)

(72) Inventor: Andrei Vertikov, Westwood, MA (US)

(73) Assignee: LX Medical Corporation, Westwood, MA (US)

( * ) Notice: Subject to any disclaimer, the term of this patent is extended or adjusted under 35 U.S.C. 154(b) by 237 days.

(21) Appl. No.: 14/040,084

(22) Filed: Sep. 27, 2013

(65) Prior Publication Data

US 2014/0276108 A1    Sep. 18, 2014

Related U.S. Application Data

(63) Continuation-in-part of application No. 13/832,868, filed on Mar. 15, 2013.

(51) Int. Cl.
| | | |
|---|---|---|
| A61B 5/00 | (2006.01) | |
| A61B 5/107 | (2006.01) | |
| A61B 5/06 | (2006.01) | |

(52) U.S. Cl.
CPC ........... *A61B 5/0084* (2013.01); *A61B 5/0066* (2013.01); *A61B 5/062* (2013.01); *A61B 5/1079* (2013.01)

(58) Field of Classification Search
CPC .... A61B 5/0084; A61B 5/1079; A61B 1/07; A61B 1/00137; A61B 1/00009
See application file for complete search history.

(56) References Cited

U.S. PATENT DOCUMENTS

| | | | |
|---|---|---|---|
| 4,826,299 A | 5/1989 | Powell | |
| 5,321,501 A | 6/1994 | Swanson et al. | |
| 5,707,684 A | 1/1998 | Hayes et al. | |
| 6,015,969 A | 1/2000 | Nathel et al. | |
| 6,069,698 A | 5/2000 | Ozawa et al. | |
| 6,134,003 A * | 10/2000 | Tearney | A61B 1/00096 356/479 |
| 6,445,939 B1 | 9/2002 | Swanson et al. | |

(Continued)

OTHER PUBLICATIONS

Davis, et al., "Interferometric Synthetic Aperture Microscopy: Computed Imaging for Scanned Coherent Microscopy", Sensors 2008, www.mdpi.org/sensors, pp. 3903-3931.

(Continued)

*Primary Examiner* — Bo J Peng
(74) *Attorney, Agent, or Firm* — Yakov Sidorin; Quarles & Brady LLP

(57) ABSTRACT

Navigational imaging system and method for use in branched luminal structure. Flexible, spatially steerable probe is equipped with forward- and side-imaging mutually complementing means to enable sub-surface imaging, quantitative determination of probe's positioning with respect to anatomical identifiers of structure, forming 3D image of structure in a volume defined by the imaging means, and positioning of probe in registration with a 3D coordinate system that is independent from the structure. Method includes determining anatomical identifiers of luminal structure branches based on 3D and sub-surface images, assigning such identifiers as fiducial points, and correlating the determined identifiers with those obtained from anatomical model to select target branch for further steering the probe. Optionally, data representing a distance between a branch of lumen from fiducial point and angular orientation of the branch is extracted from complete 3D and quantitative image of lumen obtained during a pull-back of probe along the lumen.

20 Claims, 41 Drawing Sheets

(56) References Cited

U.S. PATENT DOCUMENTS

| | | |
|---|---|---|
| 6,564,089 B2 | 5/2003 | Izatt et al. |
| 6,888,119 B2 | 5/2005 | Iizuka et al. |
| 7,233,820 B2 | 6/2007 | Gilboa |
| 7,474,407 B2 | 1/2009 | Gutin |
| 7,602,501 B2 | 10/2009 | Ralston et al. |
| 7,706,646 B2 | 4/2010 | Wang et al. |
| 7,848,791 B2 | 12/2010 | Schmitt et al. |
| 7,935,060 B2 | 5/2011 | Schmitt et al. |
| 2005/0182295 A1* | 8/2005 | Soper ............ A61B 1/0008 600/117 |
| 2007/0188855 A1 | 8/2007 | Shishkov et al. |
| 2009/0024191 A1* | 1/2009 | Seibel ............ A61B 1/0008 607/92 |
| 2009/0185191 A1* | 7/2009 | Boppart ............ A61B 5/0066 356/479 |
| 2011/0098572 A1 | 4/2011 | Chen et al. |
| 2014/0211213 A1* | 7/2014 | Weiss ............ A61B 1/005 356/601 |

OTHER PUBLICATIONS

Reed, et al, "Gradient-Index fiber-optic microprobes for minimally invasive in vivo low-coherence interferometry", Optics Letters, Oct. 15, 2002, vol. 27, No. 20, pp. 1794-1796.

A. Huttunen, Optmization of dual-coe and micosuctue fber geometries for dispersion compensation and large mode area, Optics Express, Jan. 24, 2005, vol. 13, No. 2, pp. 627.

Alexis Méndez, T. F. Morse, "Speciaity optical fibers handbook", Academic Press: 2007.

Mingua Xu, et al., "Photoacoustic Imaging in BioMedicine", Review of Scientific Instuments 77, 041101, Apr. 2006, Optical Imaging Laboratory, 22 pps.

Nelson, T. R., et al., "Three-Dimensional Ultrasound Imaging", Ultrasound in Med. Biol. 1998, vol. 24, No. 9. pp. 1243-1270.

I Turchin, et al., "Novel Algorithm of processing optical coherence tomography images for differentiation of biological tissue pathologies", Journal of Biomedical Optics , 10(6), 06024 (Nov./Dec. 2005), 11 pps.

* cited by examiner

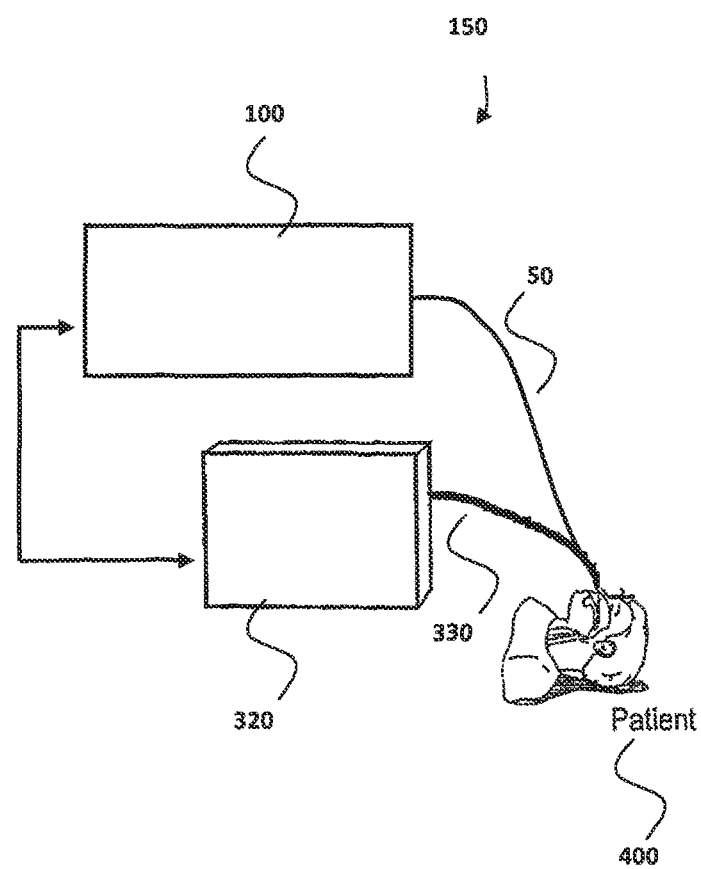

Prior Art

Prior Art

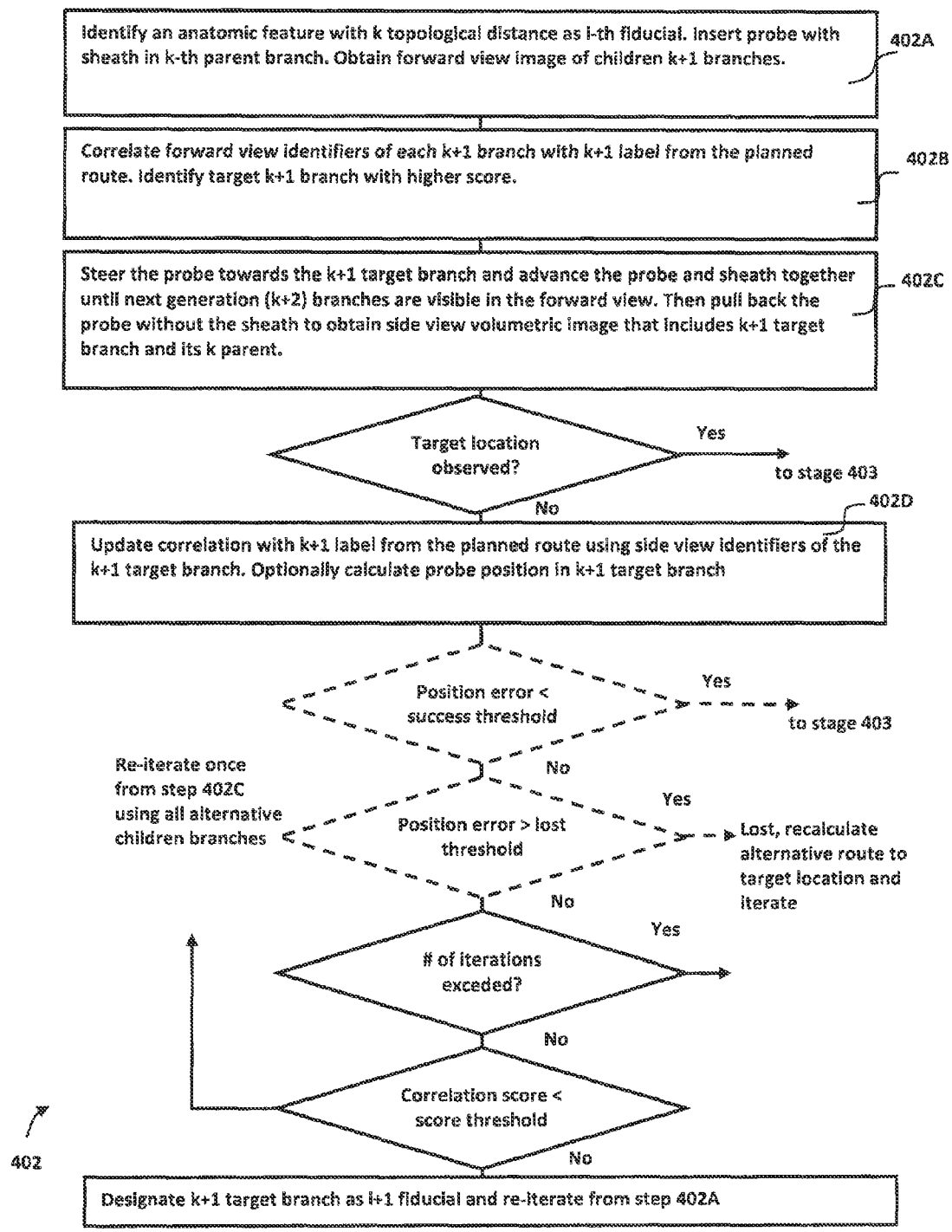

Start acquisition of side view A lines $S_n[m]$ and forward view A-lines $F_n[m]$. Start steering

---

For each $S_n[m]$, calculate maximal cross-correlations $P_n[p]$ of adjacent A-lines $S_{n+p}[m]$ along $m$ and the depth index offsets $l_n^{max}[p]$ at which the maxima are reached. Calculate the A-line number offset $p_n^{width}$ at which the maximum cross-correlation drop below threshold $r$ $$P_n[p] = \max_{l=-L...L} \left\{ \frac{\sum_{m=1}^{M} S_n[m] S_{n+p}[m+l]}{\sum_{m=1}^{M} S_n^2[m] + \sum_{m=1}^{M} S_{n+p}^2[m]} \right\}$$

$$P_n[p] < r \ (p > p_n^{width})$$

---

Calculate instant polar angle $\Theta_n$ and azimuth angle $\phi_n$ of observed scene according to pre-determined geometrical parameters of the probe distal end $$\Theta_n = \sum_{i=1}^{n} l_i^{max}[p=1] \cdot \frac{\partial \Theta}{\partial l}$$

$$\phi_n = \sum_{i=1}^{n} p_i^{width} \cdot \frac{\partial \phi}{\partial p}$$

---

Re-map forward view A-lines $F_n[m]$ to $F[x[n,m], y[n,m], z[n,m]]$ using $$z = m \cdot \delta\rho \cdot \cos\Theta_n$$

$$x = m \cdot \delta\rho \cdot \sin\Theta_n \cdot \cos\phi_n$$

$$y = m \cdot \delta\rho \cdot \sin\Theta_n \cdot \sin\phi_n$$

FIGURE 11H

Start acquisition of side view A lines $S_n[m]$ and forward view A-lines $F_n[m]$. Start steering For each $S_n[m]$, calculate maximal cross-correlations $P_n[p]$ of adjacent A-lines $S_{n+p}[m]$ along $m$ and the depth index offsets $l_n^{max}[p]$ at which the maxima are reached. Calculate the A-line number offset $p_n^{width}$ at which the maximum cross-correlation drop below threshold $r$ $$P_n[p] = \underset{l=-L...L}{Max}\left\{\frac{\sum_{m=1}^{M}S_n[m]S_{n+p}[m+l]}{\sum_{m=1}^{M}S_n^2[m]+\sum_{m=1}^{M}S_{n+p}^2[m]}\right\}$$

$$P_n[p] < r \; (p > p_n^{width})$$

Calculate instant polar angle $\Theta_n$ and azimuth angle $\phi_n$ of observed scene according to pre-determined geometrical parameters of the probe distal end $$\Theta_n = \sum_{i=1}^{n} l_i^{max}[p=1] \cdot \frac{\partial \Theta}{\partial l}$$

$$\phi_n = \sum_{i=1}^{n} p_i^{width} \cdot \frac{\partial \phi}{\partial p}$$

Re-map forward view A-lines $F_n[m]$ to $F[x[n,m], y[n,m], z[n,m]]$ using $$z = m \cdot \delta p \cdot \cos(\Theta_n + \Theta_{def})$$

$$x = m \cdot \delta p \cdot (\sin \Theta_n \cdot \cos \phi_n + \sin \Theta_{def} \cdot \cos \varphi_n)$$

$$y = m \cdot \delta p \cdot (\sin \Theta_n \cdot \sin \phi_n + \sin g\Theta_{def} \cdot \sin \varphi_n)$$

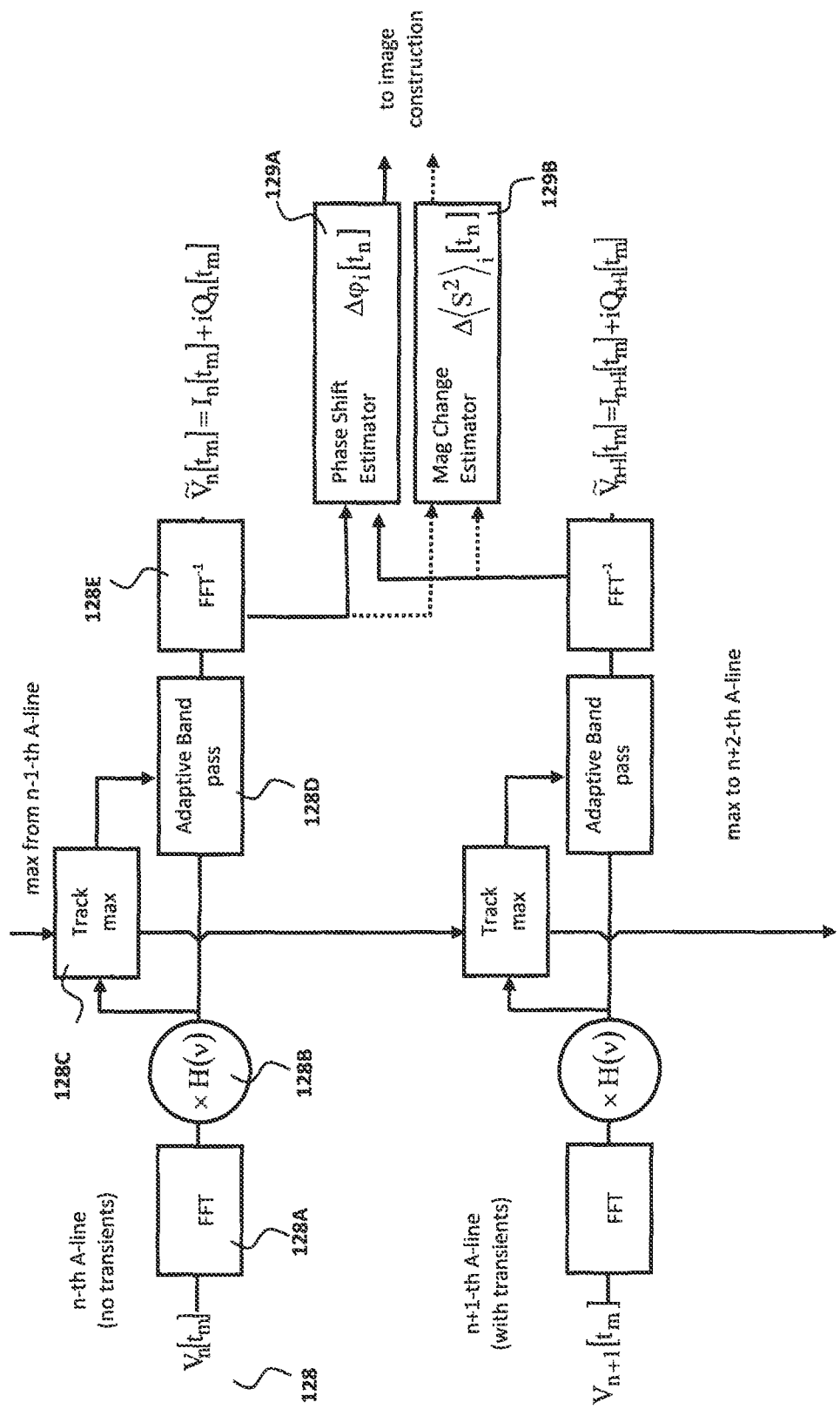

TISSUE IMAGING AND IMAGE GUIDANCE IN LUMINAL ANATOMIC STRUCTURES AND BODY CAVITIES

CROSS-REFERENCE TO RELATED APPLICATIONS

The present application is a continuation-in-part of the U.S. patent application Ser. No. 13/832,868 filed on Mar. 15, 2013 and titled "Tissue Imaging and Image Guidance in Luminal Anatomic Structures and Body Cavities". The disclosure of the above-identified patent application is incorporated by reference herein in its entirety.

TECHNICAL FIELD

The present invention relates to the field of diagnostic medical imaging and image guidance for medical procedures and, more specifically, to minimally invasive volumetric and cross-sectional tissue imaging in luminal anatomic structures and body cavities for medical procedures.

BACKGROUND

The need for sub-surface tissue imaging for medical diagnostics and image guidance and control of therapeutic and surgical procedures is well recognized. Often such imaging has to be performed in a complex, branching network of narrow and difficult-to-reach body lumens (such as, for example, blood vessels of cardiovascular and neurovascular systems, airway tree of lungs, gastrointestinal, bile and urinary tracts) or in tight spaces of natural or surgically created body cavities. There exist endoscopic ultrasound imaging devices, for example intravascular ultrasound (IVUS) or endobronchial ultrasound (EBUS) that address such need.

A higher spatial resolution imaging modality referred to as optical coherence tomography (OCT) has been recently developed and applied for endoscopic imaging in body lumens as well. The OCT systems are numerous and utilize short coherence length light sources for time-domain (TD-OCT) and spectral domain (SD-OCT) incarnations of the OCT, frequency tunable light sources for frequency domain (FD-OCT) version of OCT (see, for example, U.S. Pat. Nos. 5,321,501; 6,134,003).

OCT systems have been described that employ small diameter forward-looking probes with a push-pull actuation scheme (U.S. Pat. Nos. 6,445,939; 7,848,791); and that utilize catheters directed to location of interest thought the use of a guide wire under fluoroscopic guidance with C-arm fluoroscopic equipment (U.S. Pat. Nos. 5,321,501, 6,134,003 and 6,445,939). Fluoroscopic guidance, however, becomes cumbersome and unpractical to use in a branching, three-dimensional (3D) network of body lumens as the C-arm needs to be constantly re-adjusted. Additionally, the fluoroscopic guidance approach lacks sufficient resolution and contrast needed for navigation in small lumens, and exposes patients to harmful ionizing radiation. Even in relatively larger lumens of a cardiovascular system with simple branching, the fluoroscopic guidance is known to have problems with differentiating between main and collateral vessels during placement of catheters, especially in the case of total or partial vessel occlusion.

The use of an endoscopic image guidance and navigation and advancement of imaging probes through the endoscope working channel (described for example in U.S. Pat. Nos. 6,069,698 and 6,564,089) employs typical endoscope system for imaging and a working channel for suction and/or tools the overall diameter of which is about 5 or 6 mm, which limits the practical application of such system to large lumens. Indeed, only about one third or one fourth of bifurcation level of an airway tree in the lungs can be reached with commercially available bronchoscopes.

Imaging probes can be delivered to target locations in reliance on position sensors integrated into distal ends of separate navigating probes (U.S. Pat. No. 7,233,820) or of the imaging probe itself and using virtual images reconstructed from prior-obtained data from computer tomography, CT, or other imaging modalities. However, such a priori CT data is simply unavailable in many clinical situations, for example, in emergency care. Furthermore, the accuracy of so-defined navigation (according to U.S. Pat. No. 7,233,820 itself) depends on accuracy of the position sensors, accuracy of registering the CT data with the tree-dimensional reference of frame, and accuracy of registering the CT data with moving body of patient. These accuracy parameters are typically insufficient for small and peripheral lumens. The additional use of CCD or CMOS image sensors to obtain three camera views from different positions to improve registration of CT data with a 3D reference frame (also disclosed in U.S. Pat. No. 7,233,820) is based on triangulation of two-dimensional (2D) camera images and, therefore, has limited accuracy. In addition, integration of a camera and a position sensor does not allow achieving further miniaturization of the distal portion of the probes.

These deficiencies of fluoroscopy-based guidance and/or guidance relying on auxiliary endoscopes would be at least partially reduced if the imaging probes had their own integrated means for 3D steering and used built-in imaging capabilities for guidance and navigation. These imaging capabilities should include either capability for sufficiently long range (larger field and depth of view) imaging to image sufficient anatomic structure for reliable navigation or capability to constantly register images of local anatomic structure obtained at the distal end with global position referenced to gross anatomy of the imaged organ and/or patient body.

Sub-surface endoscopic imaging modalities referred to in related art possess certain shortcomings including a trade-off between imaging resolution and imaging depth and a trade-off between imaging resolution and probe's insertion widths. Probes having small insertion widths are, additionally, deficient with respect to directions in which such small-width probes are enabled to view the ambient medium. The deficiency stems from common implementation of side-view radial or spiral scanning, which naturally lends itself in enhancing the side looking capability of such probes but not the forward looking capability. The application of the rotational motion to enhance the forward looking capability remains a desirable goal.

One trade-off is imposed by limitations of penetration depth. While ultrasound imaging (US) has resolution on the order of 100 um, which is inferior to that of OCT (about 2 to about 10 um), the penetration depth of the ultrasound is about 10 mm, which is superior to that of about 1 to about 2 mm typical for OCT. The combination of endoscopic OCT and U.S., has been discussed, for example, in U.S. Pat. No. 7,935,060. The combination, in one imaging probe, of optical-image-forming components with ultrasound transducers and wires to produce co-registered OCT and US images increases the size of the probe and effectively prevents further miniaturization of the probe's distal end. In addition, ultrasound imaging cannot be effectively used with imaging through air-gaps, thereby requiring physical contact between probe and the tissue and/or use of liquid-filled balloons. Finally, the need for fluoroscopic and/or endoscopic guidance of a probe serves to disadvantage of the combination probes disclosed in U.S. Pat. No. 7,935,060 and US 2011/0098572.

Another trade-off between the resolution and imaging depth for the probes, that use scanning of focused optical beams, is imposed by limitations of Gaussian optics. Specifically, while the axial (depth) resolution of OCT imaging can be as small as few microns and is determined by properties of light sources, the lateral resolution, i.e., spot size, is typically few tens of microns and is determined by requirement to have sufficient depth of focus (about 2-3 mm) This limitation is especially detrimental for endoscopic imaging of lumen structures that can have wide range of sizes and irregular lumen shapes. Methods of synthetic aperture radars (SAR) and sonars (SAS) imaging have been proposed for use in OCT to overcome limited depth of focus. Another example is given in U.S. Pat. No. 7,602,501 that discloses algorithms for three-dimensional inverse signal processing for full field optical coherence microscopy and for scanned-beam optical coherence microscopy (OCM). The use of teachings of U.S. Pat. No. 7,602,501 in endoscopic OCT imaging is impractical for several reasons. First, while phase stability of imaging in OCM can be recovered by re-processing signals using reflection from high-quality optical interface of a cover glass (as disclosed in U.S. Pat. No. 7,602,501), it is unpractical to fabricate high-quality reference surface in miniature endoscopic probes. Also image distortion caused by non-uniformity of rotation and especially pull-back makes algorithms of U.S. Pat. No. 7,602,501 not applicable for endoscopic OCT imaging. Second disadvantage of the method of U.S. Pat. No. 7,602,501 is that defocusing of optical energy in all directions results in significant loss of signal strength degrading image quality even if SAR signal processing is done with correct phases. Third, implementation of orthogonal scanning such as rotation and translation may be complicated for forward-looking imaging geometries in luminal structures. Therefore, it would be advantageous to apply methods of SAR signal processing to endoscopic imaging to mitigate limitations and trade-offs of Gaussian optics without above mentioned disadvantages of methods described in U.S. Pat. No. 7,602,501 as well as without need for fluoroscopic guidance and/or additional endoscopic guidance.

The Gaussian optics also imposes the trade-off between the spot size and the size of the probes. Namely, the smaller spot size and the larger working distance of a probe, the larger aperture and therefore the larger diameter of the probe should be. To overcome this limitation, as well as limitations of mechanical scanning, US2007/0188855 proposed methods of spectral encoding of spatial locations in tissue. The disadvantages of spectral encoding include decreased depth resolution of OCT imaging and increased complexity of the probes. Another imaging method, described in U.S. Pat. No. 7,474,407, was aimed at providing non-mechanical scanning and further miniaturization of probes and discloses an OCT apparatus having at least two fibers with adjustable phase delay between the fibers that claims advantages of non-mechanical scanning. However, U.S. Pat. No. 7,474,407 fails to disclose how exactly images are formed when phase delays are changed between the fibers. The method described in U.S. Pat. No. 7,474,407 B2 is based on use of TD-OCT and does not describe how it can be implemented with faster SD-OCT or FD-OCT that are more suitable for endoscopic imaging. The same patent document does not disclose any means to ensure stable interference between optical output from different fibers in endoscopic applications, when the states of polarization in different fibers will be arbitrary and sufficiently unstable due to temperature changes and twisting-and-bending of the probes. Finally, the use of two or more optical fibers prevents further miniaturization of probes distal ends. Thus it would be advantageous to provide probes that employ methods (of information encoding and/or non-mechanical scanning) that are without above mentioned limitations of US2007/0188855 A1 and U.S. Pat. No. 7,474,407 and that are devoid of fluoroscopic guidance and/or additional endoscopic guidance.

Another clinical aspect of using imaging probes in difficult-to-reach body lumens or body cavities is the need to deliver suction, irrigation, medication, or surgical tools to the region of interest during imaging procedures. The probes of related art appear to be not concerned with working channels to address this need. When used in working channel of endoscopes, imaging probes of related art have to be temporally removed in order to clear access to the region of interest via endoscopes working channel, thereby increasing the duration of the procedure and patient discomfort. In addition, the probes of related art have to be interchanged when imaging view has to be changed from side-view (associated with imaging of lumen's sub-surface wall tissue) to forward view (needed for image guidance and occlusion imaging), or when lumens of different sizes are being imaged. U.S. Pat. No. 7,706,646 discloses a multi-view probe head, the arrangement of which falls short of producing volumetric or easy-to-interpret cross-sectional images in the forward direction because the scanning pattern of this probe head is limited to conical regions in the forward direction. Additionally, the teachings of U.S. Pat. No. 7,706,646 rely on the use of polarization-maintaining fibers, which imposes a practical limit on miniaturization of the probes. Therefore what is needed is a probe or a set of probes with built in working channels (and method for the use of such probes) and means either to avoid changing probes or, at least, to facilitate such inevitable change.

Advantages of the OCT over ultrasound modalities are not limited to increased resolution in morphological structural images. The OCT also provides functional information of tissue physiology such as absorption, blood flow, and birefringence. The functional information about light absorption in tissue is important for concentration determination of various tissue chromophores. Light absorption can also be used advantageously to delineate lumen anatomy by exploiting differences in absorption characteristics between the lumen wall tissue and media filling the lumen. Examples of using the OCT to obtain functional information about light absorption in the tissue include the applications with oxygenated or de-oxygenated hemoglobin (as described, for example, in U.S. Pat. No. 6,015,969), or water content (as described in U.S. Pat. No. 6,134,003). However, U.S. Pat. No. 6,015,969 fails to describe whether its method can be applied to body lumens (as the method is based on TD-OCT and is not suitable for endoscopic applications), while U.S. Pat. No. 6,134,003 fails to disclose algorithms of determining the chromophores' concentrations from the OCT data. An imaging probe described in US 2011/0098572, which combines optical components with ultrasound transducers and cables with capability to map absorption features in tissue by using photoacoustic effects, is disadvantageous a far as lumen applications are concerned because of its increased complexity, as well as the size of a distal end that does not allow further miniaturization of the probe. Yet another disadvantage, already alluded to above, is a need for physical contact between probes and tissue and/or use of liquid-filled balloons as ultrasound imaging cannot be effective with air gaps between the probe and imaged tissue. Therefore it would be advantageous to have an imaging probe and an associated imaging console and algorithms capable of absorptive features imaging without deficiencies mentioned above as well as without need for fluoroscopic guidance and/or additional endoscopic guidance.

SUMMARY

Embodiments of the present invention provide a multi-view imaging probe having an axis, a side surface, proximal and distal ends, and a transparent cap disposed across the axis at the distal end. Such multi-view imaging probe includes (i) an optical channel element extended inside the probe along the axis to support optical communication between the proximal and distal ends; (ii) a beamsplitting element appended to the optical channel element at the distal end to redirect light delivered along the optical channel element to the distal end transversely with respect to the axis towards the side surface to form a side field-of-view of the imaging probe; and (iii) a light redirecting system immovably disposed with respect to the distal end inside the imaging probe and including one or more optical elements spatially juxtaposed to one another. The one or more optical elements are juxtaposed to one another such as to transmit light redirected by the beamsplitting element through at least one of (a) the transparent cap along a pre-determined forward direction, to define a forward field of view of said imaging probe, and (b) the side surface. The one or more optical element are juxtaposed to one another such as, in addition, when the beamsplitting element transmits a portion of light delivered along the optical channel element to the distal end, to intersect and forward said portion through the transparent cap along a pre-determined direction with respect to the axis to define a forward field-of-view of the imaging probe. The imaging probe delivers light, received in reflection within at least one of the side and forward fields of view from an imaging target, from the distal end to the proximal end. The imaging probe may optionally include a probe-moving mechanism juxtaposed with the probe and operable to articulate the distal end with respect to the imaging target. In a specific case, the beamsplitting element is rotatable about the axis and that is structured to redirect substantially all light, delivered along the optical channel element to the distal end, transversely with respect to the axis through the side surface.

Embodiments of the invention additionally provide a multi-view image forming system that includes the above-described multi-view imaging probe as well as data-processing electronic circuitry programmed to form an image of the imaging target based on data representing light, that have been received in reflection from the imaging target within the side and forward fields-of-view, based on a known relationship between the forward direction and a rotational position of the beamsplitting element with respect to the axis.

Embodiments of the invention additionally provide a multi-view imaging probe having an axis, a side surface, proximal and distal ends, and a transparent cap disposed across the axis at the distal end. Such multi-view imaging probe includes (i) an optical channel element inside the probe supporting optical communication between the proximal and distal ends; (ii) a beamsplitting element appended to the optical channel element at the distal end to redirect a first portion of light delivered along the optical channel to the distal end transversely with respect to the axis through the side surface while transmitting a second portion of said light along the axis, the beamsplitting element being rotatable about the axis; and (iii) a light redirecting system immovably disposed with respect to the distal end inside the imaging probe and including one or more optical elements juxtaposed to one another. The juxtaposition of these optical elements is structured such as to allow the juxtaposed elements to transmit the second portion through the transparent cap along a direction inclined with respect to the axis such as to reduce the spatial angle associated with the second portion in a first direction and in a second direction that is transverse to the first direction, wherein the reduction of said spatial angle in the second direction is larger than the reduction of said spatial angle in the first direction. The imaging probe is operable to deliver light, received in reflection of at least one of the first and second portions of light from an imaging target, from the distal end to the proximal end. The light redirecting system may include a focusing element having a focusing element optical axis that is laterally offset with respect to the axis and/or a one-dimensionally-focusing lens and/or at least one optical prism defining a reduction of the spatial angle associated with the second portion. Optionally, the first and second portions of light may be different in either spectral content or polarization. Alternatively or in addition, when the beamsplitting element is rotated about the axis, the light redirecting system causes the redirected second portion to be scanned in a spatial pattern defining a conical surface. A specific embodiment of the probe may comprise a probe-moving mechanism juxtaposed with the probe and operable to articulate the distal end with respect to the imaging target.

Embodiments of the invention also provide a method for collecting optical information with the use of a multi-view imaging probe having an axis, a side surface, proximal and distal ends, and a transparent cap disposed across the axis at the distal end. The method includes redirecting a first portion of light, delivered by an optical channel element inside the probe from the proximal end to a beamsplitting element located at the distal end, along a first direction transversely with respect to the axis through the side surface while transmitting a second portion of said light along the axis, to form a redirected first portion of light. The method also includes transmitting the second portion of light through a light redirecting system that is immovably disposed with respect to the distal end inside the imaging probe and further through the transparent cap along a second direction inclined with respect to the axis, to form a transmitted second portion of light. The method additionally includes repositioning the distal end with respect to a target to receive, by the optical channel element, (i) first portion of reflected light returned to the probe by the target in response to the redirected first portion of light; and (ii) second portion of reflected light returned to the probe by the target in response to the transmitted second portion of light. The method further includes determining a position of the distal end with respect to the target based at least on cross-correlation between first data corresponding to the first portion of reflected light and second data corresponding to the second portion of reflected light.

In one embodiment, the repositioning includes bending the distal end in a plane. The determining may include correcting errors in the second data that are caused by non-uniformities of the bending respect to the target by remapping said second data based on said cross-correlation and known spatial relationships between the first direction, second direction, and said plane. The redirecting may include redirecting the first portion of light in the first direction along said plane.

In a specific implementation, the a method may additionally include rotating the beamsplitting element about the axis to scan the first portion of light with respect to the target such that the first data correspond to the first portion of reflected light reflected by the target scanned, with the redirected first portion of light, in a pre-determined circular pattern. In this case, optionally, the repositioning includes rotation of the distal and about the axis. The specific implementation of the method may further contain step(s) of remapping irregular scanning pattern defined by scanning of the second portion of light with respect to the target to a circular pattern based on an estimated instant angular velocity of the probe; and/or forming a volumetric image of the target based on remapping of the first data and the second data to Cartesian coordinates.

BRIEF DESCRIPTION OF THE DRAWINGS

The invention will be more fully understood by referring to the following Detailed Description in conjunction with the Drawings, of which:

FIG. 1 is a diagram of a minimally-invasive high-resolution imaging apparatus according to an embodiment of the invention;

FIGS. 6A, 6B, and 6C are flow-charts depicting a navigational procedure using image guidance according to an embodiment of the invention;

FIG. 11F is a flow-chart representing an algorithm for correction of errors in the forward imaging effectuated by an embodiment of FIG. 11B and cased by the bending of the distal end of the probe of the embodiment;

FIG. 11H is a flow-chart illustrating an algorithm for re-mapping of data received as a result of imaging according to the pattern of FIG. 11G into the Cartesian coordinates;

FIG. 22 is a flowchart of signal processing procedure for use in operation of the embodiment of FIGS. 21A-21C.

DETAILED DESCRIPTION

Figure 2A:
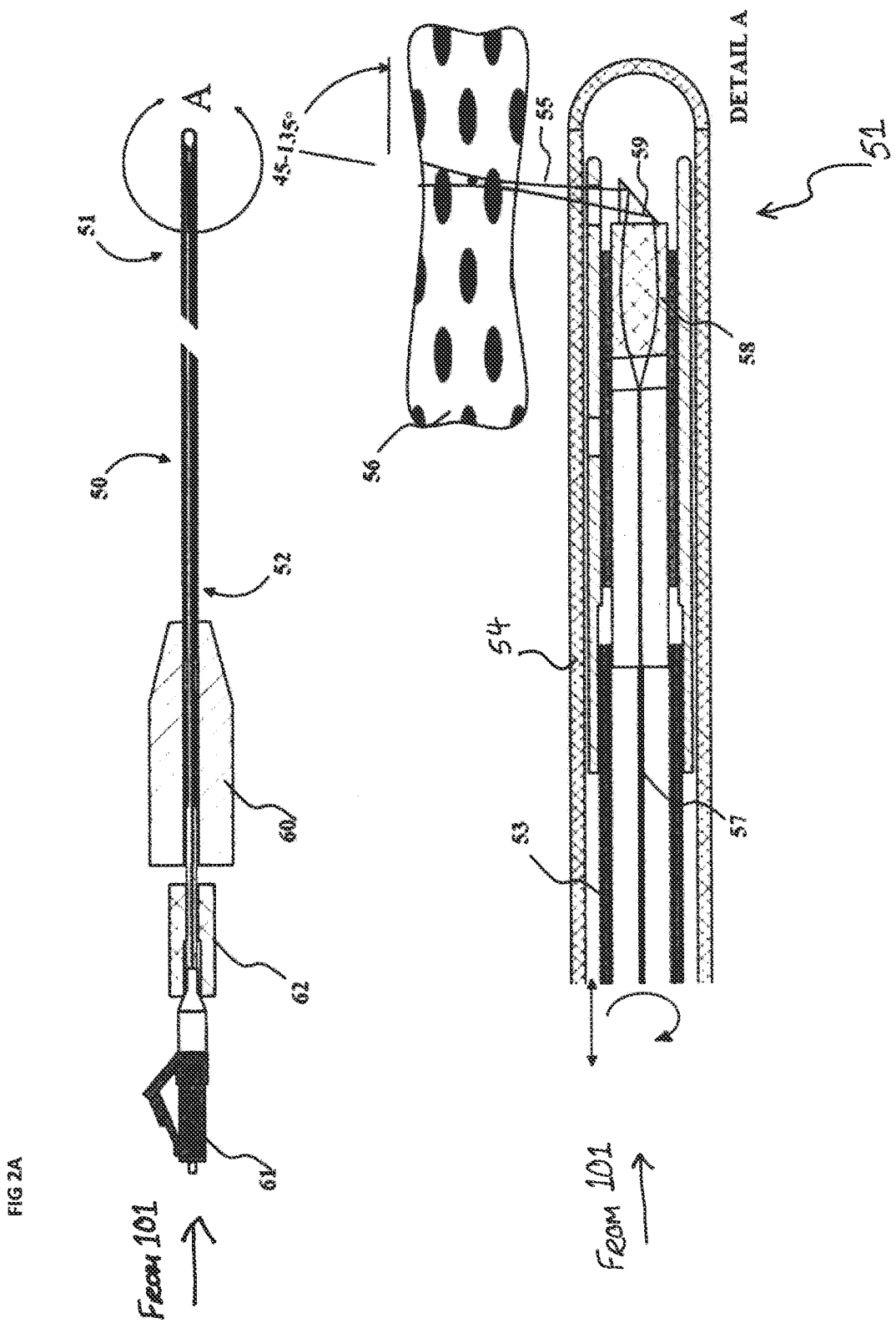
FIGS. 2A and 2B illustrate an imaging probe and an imaging console, respectively, or use with the embodiment of FIG. 1.

For clarity of the presentation, the following disclosure is structured subdivided as follows. The description associated with FIGS. 1 through 4 is the general description of imaging apparatus and methods of the invention. The description associated with FIGS. 5 and 6 related to navigational aspects of the embodiments of the present invention. Embodiments of probes characterized by improved resolution, combined side and forward-directed imaging, extended depth of focus, and improved scanning methods are described in relation with associated imaging console components and signal processing algorithms, in reference to FIGS. 7-17. In reference to FIGS. 18-21, several embodiments of apparatus and methods providing improved absorptive features mapping of the present invention are described.

Embodiments of the Overall System.

FIG. 1 shows a patient 400, whose vital conditions (such as blood gases or heart rate) monitored with monitoring equipment 320. A high-resolution imaging probe 50 with a substantially small insertion width is inserted into the patient's natural body opening or subcutaneously (via a hypodermic needle) to a bodily lumen. The probe 50 is then advanced to a target region or location where the lumen tissue is being imaged. During the imaging procedure, the probe 50 remains in operable communication with an imaging console 100 that controls the probe 50 and processes data received from the probe 50 to form sub-surface cross-sectional and/or volumetric images of the tissue. Aggregately, the probe 50 and the imaging console 100 are referred to as a medical imaging apparatus 150.

The term "substantially small insertion width" implies, in the context of the present disclosure, that the probe 50 is dimensioned to be (i) insertable into body lumens (such as, for example, airways or blood vessels.) and, on the other hand, (ii) compatible with a commercially available endoscope having a working channels of about 2.8 mm in diameter or narrower. The probe insertion width, therefore, are chosen to be less than 2.5 mm and preferably less than 0.5 mm. While the preferred insertion width is in a range between about 0.2 to about 2.5 mm, the scope of the present invention is not limited to such range and is applicable to all probes designed for insertion in body lumens. The term "high-resolution imaging" refers to imaging with ability to resolve at least one type of typical sub-surface tissue structure of a lumen wall and, preferably all features of such structure. The imaging resolution of a system of the invention is at least 0.2 mm and preferably better than 0.02 mm. Embodiments of the invention are configured to carry out imaging with the high-resolution in real time in order to (i) not be affected by the motion of the tissue during the process of imaging and tissue motion (ii) be able to detect a motion of the probe relative to a lumen wall during navigation through the lumen. Accordingly, in the context of the present invention "real-time imaging" implies imaging at a rate substantially faster than respiratory or hear rate (for example, faster than 1 frame per second (fps) and preferably faster than 10 fps).

Figure 2B:
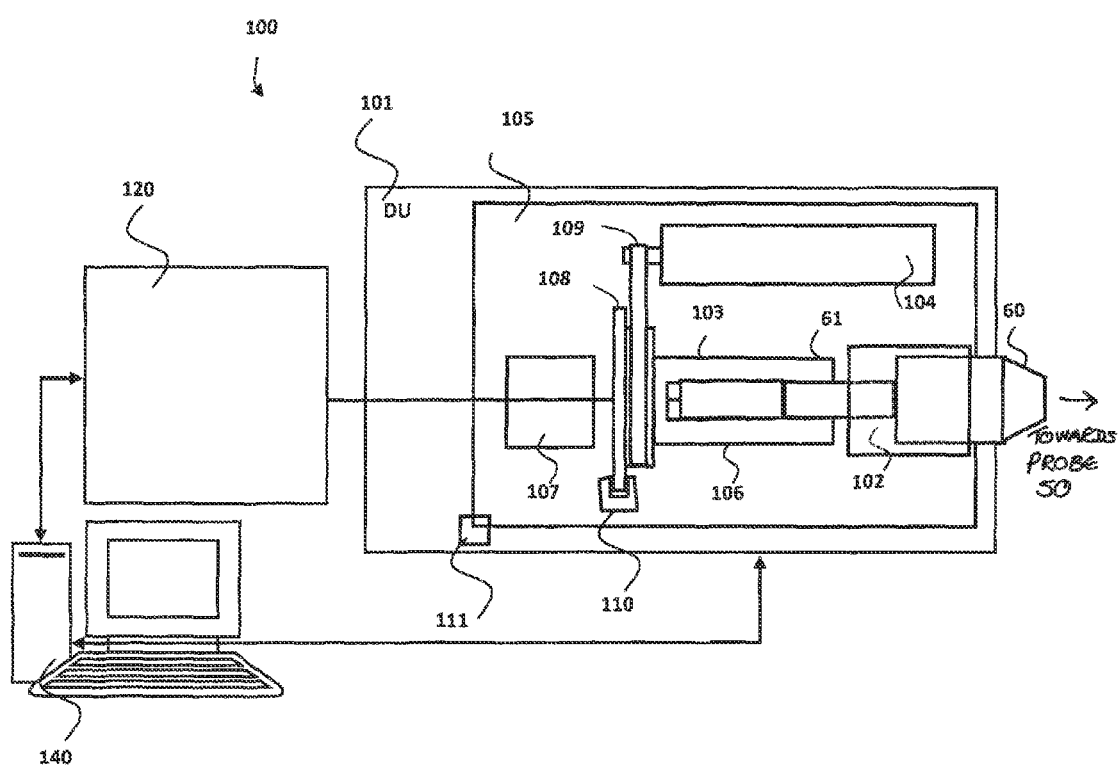

FIG. 2B provides an example of the console 100 of FIG. 1. The console 100 contains a drive unit (DU) 101, an energy-processing (electronic and/or electro-optical) module 120, and a computer or computer-processing unit (CPU) 140 with a user interface. The DU 101 secures a portion of the probe 50 (as shown, the probe hub 60 with a hub holder 102, which can be a metal tube with a clamping setscrew). The DU 101 also has a connector 103 mating with the probe connector 61 to couple the non-ionizing imaging energy between the module 120 and an embodiment of a high resolution imaging probe 50. As discussed below, to enable the rotation and/or translation of the shaft of the probe 50 relative to its outer sheath, the DU 101 is equipped with a rotational motor 104 mounted on a translation stage 105 together with a DU mechanical coupler 106 that coordinates with the mechanical coupler and a rotary joint 107. The rotary joint 107 facilitates the movements of the shaft of the probe 50 without affecting the energy transfer passage therethrough. In some embodiments DU 101 facilitates the translation of the probe's outer sheath and the probe's shaft together. In this case, the DU 101 may be equipped with a translational motion coupler configured, for example, as the hub holder 102 mounted on the translational stage 105. The translational stage 105 can be for example any rotational DC motor equipped with a screw drive mechanism. The mechanical coupler 106 can be a hollow slotted metal tube inserted in a rotary bearings 108 and clamped to the body of the connector 61 for example with a setscrew. The rotary bearing 108 is secured to the translation stage 105 together with rotational motor 104 and is coupled to the shaft of the motor 104 for example with a belt 109. The DU 101 is preferably equipped with synchronization sensors 110, 111 that generate pulses synchronized with rotation and/or translation of the DU-stages. Both the DU 101 and the energy-processing module 120 are in communication with the CPU 140 that governs the operation of the DU 101 motors and processes DU synchronization pulses and processes data representing the energy handled by the module 120 to construct to construct high-resolution images.

A general diagram of the high-resolution imaging probe 50 of the imaging apparatus 150 of FIG. 1 is shown in FIG. 2A to include an axially elongated, flexible body having substantially small insertion width, a distal end 51 (to be inserted in a lumen), and a proximal end 52 (cooperated with the imaging console 100). Generally, the probe 50 has a flexible core or shaft 53 enclosed in an outer sheath 54. The sheath 54 includes a single- or multi-lumen preferably sealingly closed with a smooth rounded tip at the distal end 51. However, in some embodiments of the probe 50, as discussed below, at least one lumen of the sheath 54 is open to the ambient at the distal end 51 to act as a working channel. Such single-lumen or multi-lumen catheter can be fabricated, for example, by extrusion process from variety of suitable polymers (such as PTFE, FEP, nylon) with suitable dimensions (for example, inner diameters and wall thicknesses as small as 50 μm). As coordinated by the DU 101 of FIG. 2B, the shaft 53 of the probe 50 is freely rotatable and/or translatable relative to the sheath 54 at least in some embodiments. During the operation, the probe 50, driven by the module 120 of FIG. 2B, projects a non-ionizing interrogating energy 55 (such as ultrasound energy and/or optical energy) toward the ambient medium that may include lumen tissue 56. The probe 50 also receives the return energy originated at the tissue in response to the interrogating energy and encoded by the tissue response.

Referring again to FIG. 2A and in further reference to FIG. 2B, a proximal end 52 of the probe 50 has the hub 60 is affiliated with the sheath 54 and a connector 61 at a proximal end 52 of the probe 50, and a mechanical coupler 62 attached to the shaft 53 in an intermediate position between the hub 60 and the connector 61. The hub 60 secures the probe 50 to the console 100 of FIG. 1 and can be a metal or plastic tube bonded to the sheath 54 with adhesive(s). The connector 61 facilitates the coupling of energy between the console 100 and the probe 50 and will be described in more detail below. The mechanical coupler 62 allows the transfer of rotational and/or translational motion from the console 100 to the probe 50 in at least some embodiments, and, in its simplest form, can include a plastic or metal tube bonded to the shaft 53.

In the specific embodiment shown in an insert of FIG. 2A and labeled "Detail A", the interrogating energy 55 is generated in the console 100 of FIG. 1 and delivered through a means for delivery of energy (such as an energy guide 57 in the shaft 53) to the distal end 51 probe 50 to be projected to the ambient medium. In alternative embodiments, the interrogating energy 55 can be generated from electrical signals and converted to electrical signals by a transducer located at the distal end 51. An embodiment of the probe 50 additionally includes a means for coupling of energy between the module 120 and the ambient medium 56 around the probe within a predetermined angle range. Such means for coupling is cooperated with the energy guide 57 at the distal end. In a specific case shown in FIG. 2A, the means for coupling includes an energy focusing element 58 and an energy redirecting element 59.

In different embodiments, the means for coupling the energy between the probe 50 and the ambient medium can be structured as side-looking means (configured to operate within the first angle range defined between about 45 degrees and about 135 degrees, and preferably close to about 90 degrees, with respect to the axis of the probe 50) and/or as forward-looking means (defined to operate within the second angle range defined between about −45 degrees and about 45 degrees with respect to the axis). The specific implementation of the probe 50 shown in FIG. 2A illustrates the probe with side-looking means for coupling energy. While a side-looking probe may prove to be more suitable for imaging lumen walls and tissue behind the walls in small lumens, a forward-looking probe may have advantages during the navigation in the branching tree of lumens and for imaging of lumen obstructions. The imaging apparatus 150 of FIG. 1 is optionally equipped, as discussed below, to facilitate exchange or switch between the forward-looking and the side-looking interrogating capabilities, for example by employing separate guide sheaths kept in lumens while individual probes guided by such sheaths are interchanged. As discussed below in more detail, a related embodiment of the probe 50 can be configured to possess dual-view capabilities when both forward-looking and side-looking images are obtained either simultaneously or sequentially, by switching between the views without changing the probes.

In operation of some embodiments of the system of the invention, the direction of delivery of the focused interrogating energy from the means for coupling energy of the probe 50 to the ambient can be changed in time (for example, scanned) to form an image of the ambient directly by establishing a one-to-one correspondence between the image pixels (or voxels, for a volumetric imaging) and the locations at which the interrogating energy is concentrated in the tissue. Scanning patterns to change the focusing direction can vary (as long as there is sufficient irradiation of the imaged tissue region) including but not limited to raster scan, rotary-radial scan, rotary-liner scan, and rotary pullback, or spiral scan, for example. In alternative embodiments, the high-resolution images can be further synthesized or reconstructed not only in a direction corresponding to the depth of the tissue but in other directions as well, and without one-to-one correspondence between the image pixels (or voxels) and the direction of the projected interrogating energy. The present invention applies various methods for reconstruction of images from imaging data, received from the object in a plurality of directions, to the construction of high-resolution images of lumen walls and subsurface tissue. The advantage of such "synthetic" imaging—at least with respect to optical imaging—is that the trade-offs between lateral resolution and depth of focus imposed by the Gaussian optics and trade-offs between resolution and probe size can be lifted.

Additional Considerations.

In addition to the already described requirements for small insertion widths, the probe 50 of FIG. 1, to be properly delivered to small and peripheral branches of a lumen tree, should be property structured to possess 1) steerability, i.e., ability to aim the probe distal end in the lumen direction where the probe 50 needs to be inserted; and 2) navigation capability, i.e., ability to visualize lumen and identify the imaged luminal branches so that the probe 50 can be reproducibly delivered to target regions. Referring first to general issues of steerability and navigation, FIGS. 3A, 3B, 3C, and 3D illustrate several embodiments configured for delivery of high-resolution imaging probes of the present invention to the target region of a luminal tree.

Figure 3A:
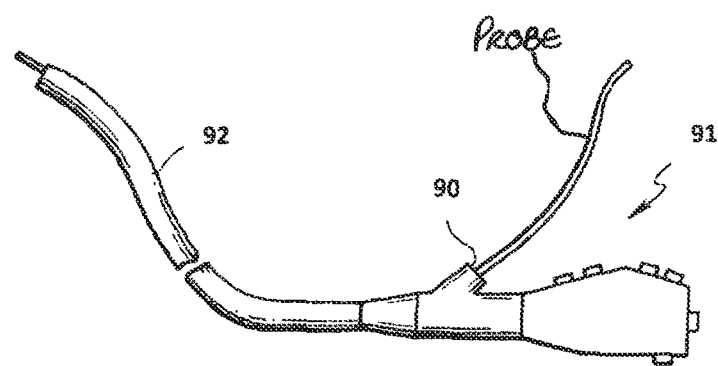
FIGS. 3A, 3B, 3C, and 3D are diagrams illustrating methods for delivery of the imaging probe of FIG. 2A to the target region.
Figure 3B:
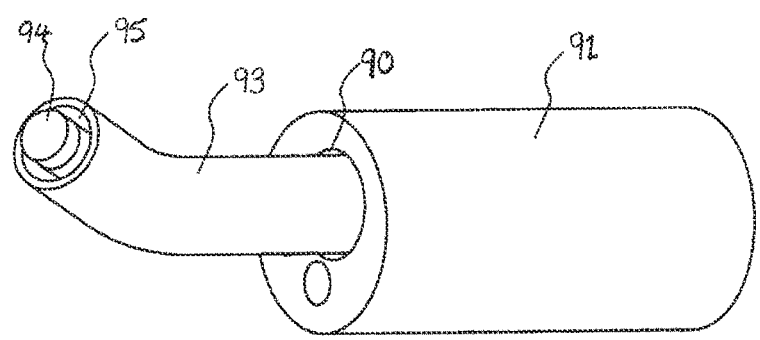
Figure 3C:
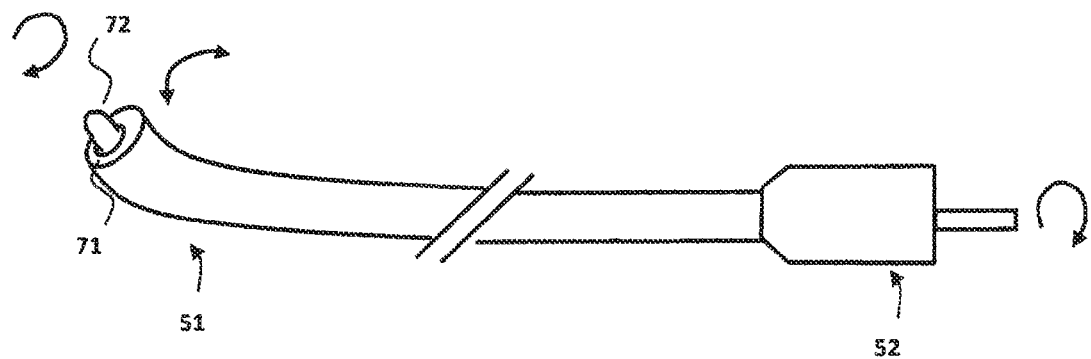
Figure 3D:
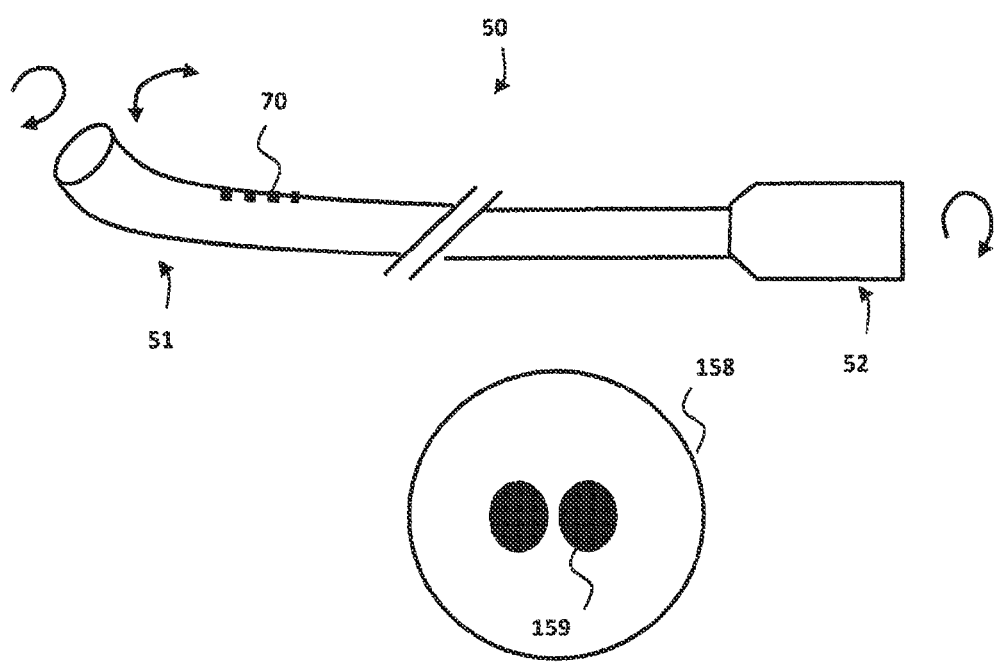

In one embodiment, the probe such as the probe 50 can be delivered to the target region under endoscopic guidance via a working channel 90 of a commercially available endoscope 91, as shown in FIG. 3A. Manual observation and/or automatic registration of the branching points of the luminal tree allow tracking of the probe position in a luminal branch, while endoscope steering mechanisms 92 allow aiming the probe 50 into the target lumen for further insertion. In another embodiment shown in FIG. 3B, a guide sheath 93 is inserted first through the working channel 90 of the endoscope 91 and navigated to the lumen of interest by means of a navigational steerable catheter 95 with an integrated electro-magnetic (EM) position sensor 94. The EM sensor 94 allows using EM navigation and/or virtual endoscopy to deliver the edge of the guide sheath 93 to the region of interest. Then the navigational catheter 95 is removed, and the probe 50 is inserted in the guide sheath 93. Such guide sheaths with steerable EM or fluoroscopically navigated catheters are exemplified by commercially available products from superDimension of Minneapolis named InReach™ navigational system. Yet another embodiment for use in cardiovascular applications is shown in FIG. 3C, where a guidewire 72 is first delivered to the target region under fluoroscopic guidance and then the imaging probe is 50 delivered to the target region over the guidewire using a lumen 71.

The use of endoscopic guidance and/or commercially available EM navigated guide sheaths limit the accessible range of lumens, while the use of fluoroscopic guidance is complicated in branching network of lumens. Therefore, using the high-resolution imaging capability of the probe 50 of FIG. 1 for navigational guidance, and combining such imaging capability with the probe's own, internally contained steerable means are advantageous in reaching smaller and more peripheral lumens. Moreover, endoscopic guidance, EM navigated guidance and imaging probe's own guidance means can be advantageously combined, whether concurrently or sequentially, to reach small peripheral lumens. Accordingly, in a preferred embodiment of the high-resolution imaging probe 50, shown in FIG. 3D and used for image guidance and navigation, the distal end 51 is equipped with steering and/or bending means 70 (shown schematically) that allow bending of the distal end 51 in at least one direction. While being sufficiently flexible to facilitate such bending, the outer sheath of the probe 50 has at the same time sufficient rotational rigidity to facilitate the ability of the probe 50 to rotate the distal end 51 by having the proximal end 52 rotated (referred to herein as torqueability). Furthermore, if the torqueability is sufficiently high and the lumen structure includes branches with small branching angles, it might be sufficient to have pre-determined fixed bending angle at distal end of the probe for steering functionality. Plastic materials such nylon, PTFE, Pebax can be used to make the probe's outer sheath with such property of high torqueability combined with high flexibility of distal end. In addition, braids of metal wires can be incorporated and/or embedded in the probe 50 outer sheaths to further improve torqueability without increasing flexural stiffness. During the navigation of the probe 50 along a lumen, a high-resolution image 158 of a lumen is obtained from the forward movement of the probe directions so that lumens 159 in front of the probe are seen. By bending the distal end 51 with the steering means 70 and rotating the probe 50 along its axis (by rotating the proximal end 52), the probe 50 can be aimed in a chosen forward-looking direction until the target lumen is in the center of the forward-looking image 158. The probe 50 can then be safely inserted in the target lumen. Three or more steering means 70 discussed below, when places circumferentially around the body of the probe enable aiming of the probe in substantially any forward-looking direction without the rotation of the probe. Several steering means 70 can be also distributed along the length of the probe 50 to further facilitate bending. The steering means can be also a separate steerable element, such as commercially available steerable guidewire inserted into a lumen of a probe 50. The advantage of such arrangement is that the separate steerable element can be removed from the probe lumen so that the probe lumen can be also used as a working channel. The steering can also be effectuated by permanently bending the distal end of the probe and using the rotation of the probe about its axis so that the probe conforms to the branching geometry and utilizes the lumen branching angle to deflect its distal end.

Embodiments of the Steering Means

Figure 4A:
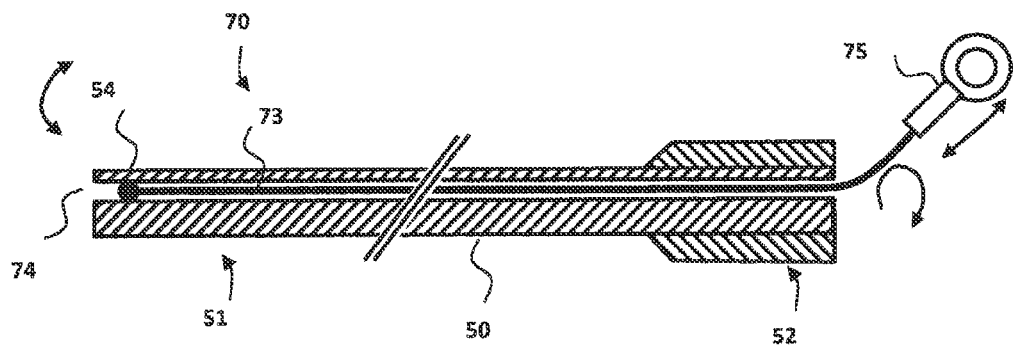
FIGS. 4A, 4B, 4C, 4D, 4E, 4G show several embodiments of steering means for delivery of the imaging probe using the method corresponding to FIG. 3D.
Figure 4B:
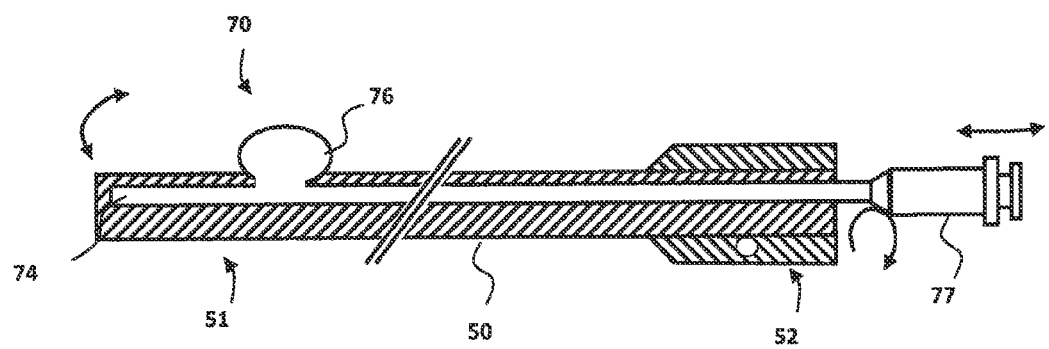

With reference to FIGS. 4A-4G, description of steering means for the high-resolution imaging probes is provided. FIG. 4A shows cross-sectionally one embodiment of the steering means 70, with the use of which the bending of the distal end 51 of the probe 50 can be effectuated by pulling a wire 73 inserted into a lumen 74 of the probe 50 and attached to the outer sheath 54 at the distal end 51 and to a pulling handle 75 at the proximal end 52. Adding more lumens with more wires in them increases the number of direction of bending the probe, thereby simplifying steerability. The pulling wire 73 can be made from a variety of materials, for example from stainless steel preferably coated with PTFE to minimize friction during actuation. The distal end of the wire 73 can be attached to the sheath during sealing of the distal end by heating the sheath in a metal die. Another embodiment of the steering means 70 is shown cross-sectionally in FIG. 4B and is equipped with a balloon or plurality of balloons 76 disposed in at least one location along circumference of the probe 50. The at least one balloon is deployed thus displacing the probe asymmetrically with respect to the probe's axis. The balloon 76 can be deployed by air or liquid that fills the probe lumen 74 sealed at the distal end 51, for example by epoxy. The balloon can be made from variety of plastics such PVC, PET, and nylon and can be attached to the outer sheath 53 with adhesives. The deploying pressure of air or liquid inside the lumen 74 can be controlled by a syringe 77 at the proximal end 52.

Figure 4C:
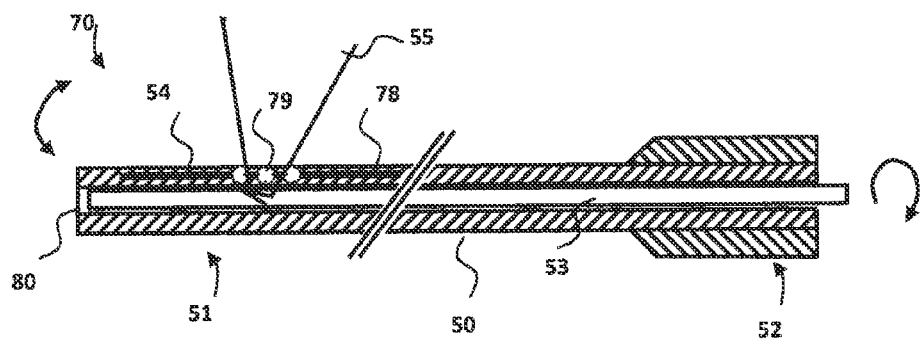

Yet another embodiment of the steering means 70, shown cross-sectionally in FIG. 4C, utilizes at least one shape changing element 78 made of a shape memory alloy (SMA) or shape memory polymers (SMP) that bend or otherwise change shape, thereby causing the bending or twisting of the distal end 51 in at least one direction. SMA materials such as nithonol are used in the medical devices and can be used in this embodiment. The SMA shape changing element 78 may be in the shape of a wire that recover bended state with temperature change, the shape changing element 78 being embedded in the outer sheath 54 at the distal end 51. Alternatively, SMA shape changing element 78 elements can be deposited on the outer surface or inner surface of the outer sheath 54 at the distal end 51, in the form of meandering stripes thus causing bending of the probe with temperature changes. A section of the outer sheath 54 at the distal end 51 can be made of SMP such as a commercially available thermoplastic MM5520, DiAPLEX Company, Ltd that recovers (changes) primary, bended shape from secondary, straight shape when temperature is above soft phase glass transition $T_{gs}$~55 deg. The SMP section can be fused or bonded with adhesive to the rest of the outer sheath 54. It is possible to activate shape changes in SMA or SMP element 78 by passing electrical current through them and changing their temperature by Joule heating. It is also possible to change element 78 temperature be changing temperature of the liquid or air that fill internal lumens of the probe 50 thus controlling the element 78 shapes from the probe proximal end 52. Yet preferred embodiment to activate shape changes is to dispose energy absorbing elements 79 in the distal end 51 in the thermal contact with the shape changing element 78. The example of the energy absorbing element 79 for the case of optical energy is indocyanin green (ICG) dye that can dope the outer sheath 54 or the shape changing element 78 itself in case of using SMP. By directing portion of the imaging energy 55 from the probe shaft 53 disposed in a lumen 80 towards the energy absorbing element 79 the shape changing element 78 can be heated and the shape changes can be activated. One advantage of using SMP in the shape changing element 78 is that shape changes can be activated by non-thermal mechanisms. For example, light can be delivered by the probe to its distal end towards the SMP element 78 and the light of one wavelength can activate shape changes while the said light of different wavelength can deactivate them. Another alternative is to activate shape change by delivering activation chemical agents via lumens of the probe 50.

Figure 4D:
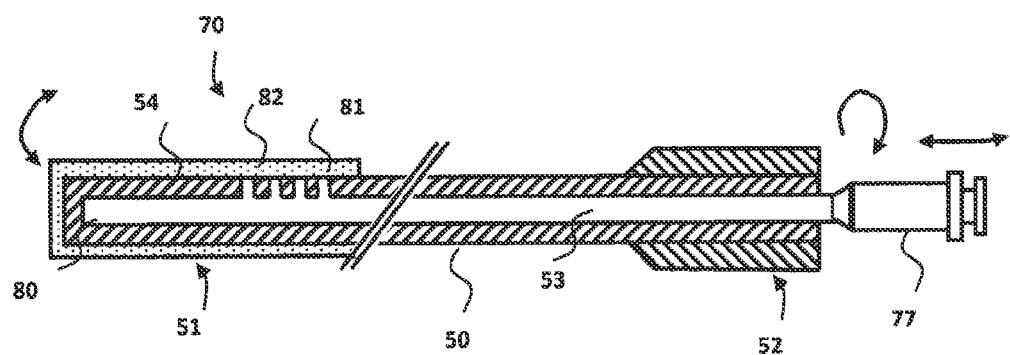

A related embodiment of steering arrangements is shown cross-sectionally in FIG. 4D. Here, bending of the probe distal end 51 in at least one direction is actuated by changing a pressure of liquid or air in the sealed lumen 80 that holds the probe shaft 53 (not shown for clarity of illustration). In this embodiment, the distal end 51 of the probe 50 is asymmetrically modified to change its flexural stiffness in one direction in at least one segment of the probe circumference. When pressure in the lumen 79 is increased, the distal end 51 bends. One practical way for such asymmetrical modification of flexural stiffness is to fabricate at least one slot or array of slots 81 perpendicular to the axis of the probe 50 in the walls of the outer sheath 54. The slots 81 may have width and spacing between then substantially equal to the thickness of the outer sheath 54 and the depth substantially equal to half of the outer sheath 54 diameter. The slots 80 can be fabricated for example by laser machining or other precision methods and then can be covered by a more flexible secondary sheath 82 to seal the lumen 80. The secondary sheath 82 can be made from the same material as the prime sheath 54 and have significantly thinner walls to have higher flexibility. The secondary sheath 82 and the primary sheath 54 can be bonded at least at some locations with heat fusion or adhesive bonding to improve sealing of the lumen 80. Alternatively, more complicated structures machined on the sheath walls and/or asymmetrical braiding of the sheath 54 can create asymmetrical reduction in flexural stiffness of the distal end 51 and can be used for bending the probe 50 by increasing pressure in the sealed lumen 80. The pressure of the lumen 80 can be controlled by the syringe 77. Alternative implementation of pressure actuating bending is to have asymmetrically disposed occluded lumens similar to arrangements of FIG. 4A but without wires in them and distend these lumens longitudinally by increasing the lumen pressure thus bending the distal end 51.

Figure 4E:
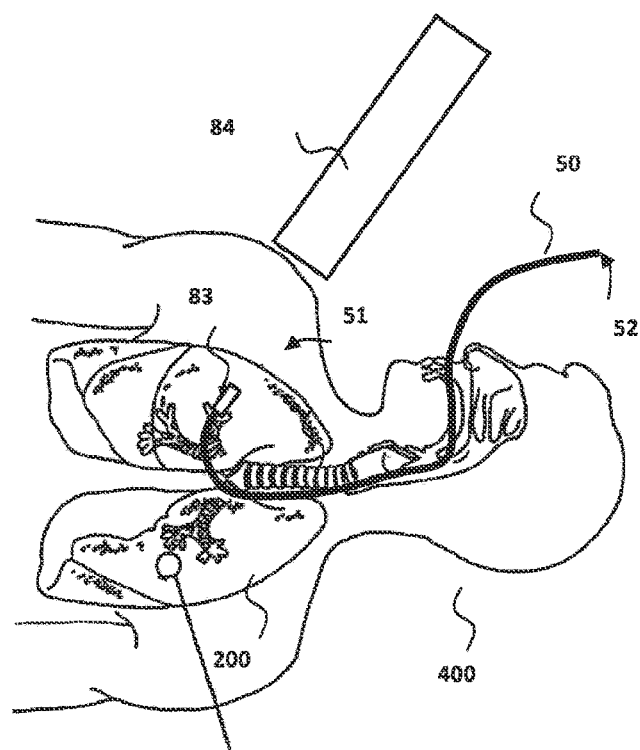

In another embodiment, illustrated in FIG. 4E, the external magnetic field is used to steer the probe distal end 51. Here, the distal end 51 contains a magnetic element 83, for example a small tube made from magnetic alloys such as NiFe. A plurality of DC or electromagnetic magnets 84 disposed externally to the patient 400 align magnetic field in the patient body 200 in the required direction to spatially align the distal end 51 until the body lumen is centered in the probe forward imaging field of view. After, the probe 50 can be inserted into the body lumen by pushing the probe from the proximal end 52 or by moving the magnets 84 and or changing the magnetic field. Such magnetic steering, well known for cardiovascular applications and commercialized by Stereotaxis of St. Louis, Mo., is combined with the image guidance and is applied for probe navigation for high-resolution imaging of lumen tissue in the present invention.

Figure 4G:
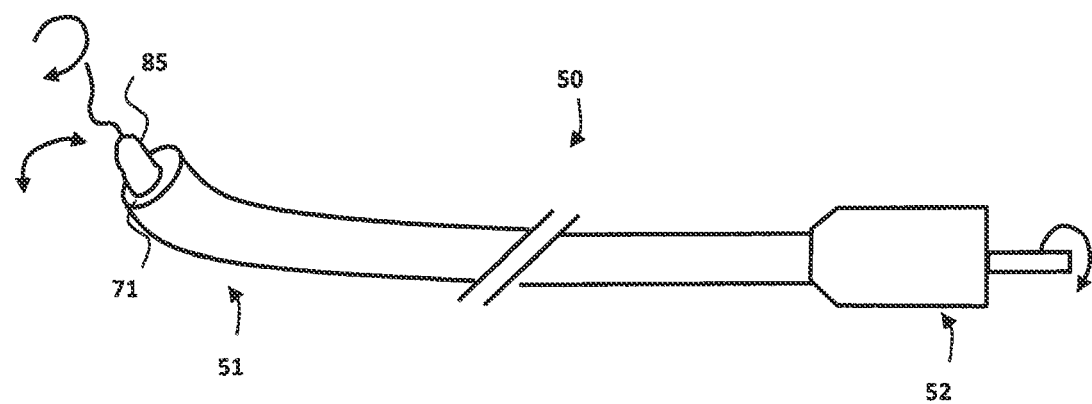

In one more alternative embodiment shown in FIG. 4G a separate steering element 85, such as a steerable guidewire, is inserted into the working channel 71 of the probe 50 to steer the probe distal end. All steering arrangements shown in FIGS. 4A-4D can be used in the removable steering element 85. However, there is tradeoff between steering capabilities and cross-sectional dimensions of the steering means. The steering force supplied by steering elements compatible with small working channels may not be sufficient to effectively bend the distal end of the probe. In such cases, it might be more advantageous to use a guidewire approach commonly used in the cardiovascular applications of the catheters. In this approach the guidewire 85 is protruding from the probe working channel 71. The guidewire 85 is inserted first into the lumen of interest under the probe 50 imaging guidance. The probe 50 slides over the guidewire 85 into the airway once the guidewire is securely placed in the airway lumen. The guidewire 85 can be any commercially available guidewire, e.g. Fathom™ Steerable Guidewire by Boston Scientific and may have its own steering means that typically consist of outer coil and inner wire, the inner wire can move inside the coil or can be welded asymmetrically to the coil to steer the distal end. The distal ends of commercially available guidewires are several hundreds of micrometers in diameter. Alternatively, said guidewire can be passive without steering means with incorporated bend into in its distal end. By controlling the protrusion distance, by rotating guidewire in the working channel, and rotating probe it is possible to insert the guide wire into the airway of interest located in the forward hemisphere. The separate steering element can be also implemented in the form of an outer sheath in which the probe 60 can be inserted. Such separate steering sheath may have active steering capability or have pre-formed bend so that rotating the sheath distal end from the proximal end results in steering the distal end of the sheath with the probe 50 inserted in it.

Examples of Embodiments of the Imaging Probe System and Method of Navigation of Same.

Figure 5:
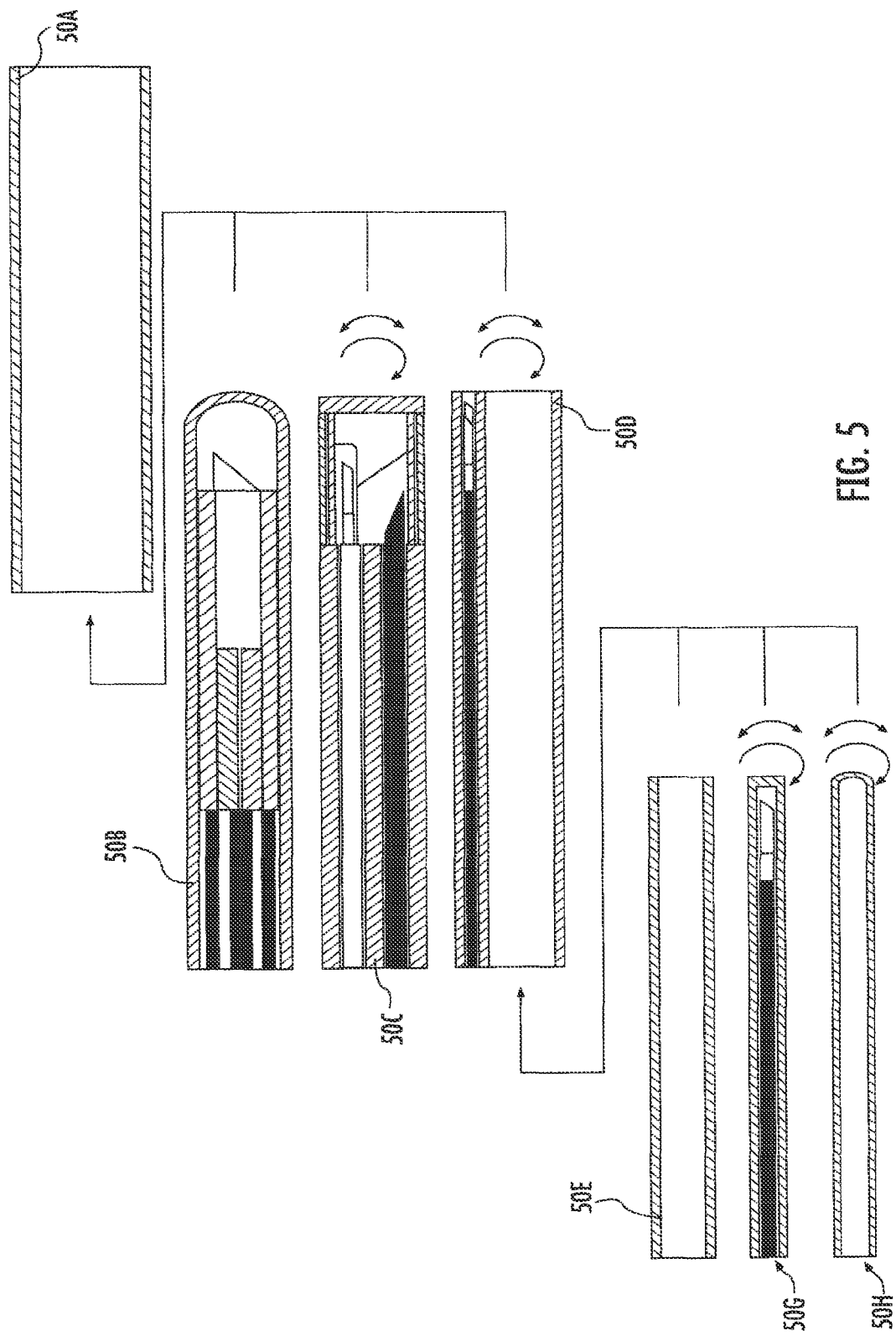
FIG. 5 shows an example of a set of substantially co-axially nested probes, guide sheaths and guidewires.

According to one aspect of the invention, the imaging probe system is used, as part of the apparatus 100 of FIG. 1, to navigate a target luminal tree. Navigational aspect of the present invention can be better understood if general relationship among imaging probes, guide sheaths, guidewires and medical devices that can be guided with the imaging probes in practicing this invention is described first. With reference to FIG. 5, embodiments of the probes used in the apparatus of the invention are characterized by working channels facilitating the processes of medication, ventilation, aspiration and delivery of medical devices to the small and peripheral branching lumens of the target luminal tree. Another aspect is minimization of probes removals and reinsertion during procedures. It is preferred that a single probe component have both forward and side-looking imaging means, be steerable, and include a working channel. Since there is a tradeoff between the insertion width of the probe and a size of the working channel, an embodiment of the imaging probe system of the invention may include a set of probes with different insertion widths and different dimensions of working channels. Some of the probes in such set or some combinations of probes, guide sheaths, and guidewires in this set should combine at least two of the above-mentioned required capabilities to minimize procedures duration and patient discomfort. For the purpose of illustration and not limitation, FIG. 5 depicts an example of one possible set defining a probe system. The set include of a guide sheath 50A (of approximately 2 mm OD and 1.8 mm ID); a 1.5 mm OD side imaging probe 50B; a 1.5 mm OD navigational probe 50C characterized by forward-looking imaging means and ability to be spatially steered, and preferably a side imaging capability. The set additionally include a 1.5 mm OD forward-looking imaging probe (with a 1 mm ID working channel 50D); a smaller guide sheath 50E (with approximately 1 mm OD and 0.75 mm ID); a 0.5 mm OD steerable side imaging probe 50G; and a 0.5 mm steerable guidewire 50H.

An embodiment of the preferred method of using the set of probe components of FIG. 5 includes steering the navigational probe 50C along a lumen of choice to the region of interest (ROI) together with and inside the guide sheath 50A, using the steering means and image guidance elements of the navigational probe 50C. Then the navigational probe 50C is removed from the guide sheath 50A so that medication, ventilation, aspiration, and interventional devices can be delivered via the guide sheath 50A. The side-looking imaging probe component 50B can be then inserted in the guide sheath 50A to enable the high-resolution imaging of the lumen tissue. To reach lumens that are peripheral to the lumen of choice or those with smaller dimensions, the probe 50D having the working channel can be inserted via the guide sheath 50A and then navigated to a target region using its own forward-looking imaging means and the available steering means (for example, a guidewire 50H or the steerable probe component 50G that has been inserted in the working channel of the probe component 50D). Once the target region is reached, a volumetric imaging is performed with the probe 50G, and the smaller guide sheath 50E can be used to facilitate pull-back of the probe component 50G from the working channel of the probe component 50D. Aspiration, ventilation, irrigations and medical devices can be delivered at this point to the target region via the working channel of the probe component 50D, while forward-looking imaging means of the probe 50D allows for guidance of diagnostic or therapeutic procedures in the target region.

In reference to branching luminal structures, it is instructive to distinguish between the exact anatomic model of a luminal structure and its topological model characterized by branching-point hierarchy and unique identifiers of each branch. It should be understood that the term branching point is used in this disclosure to represent both topological relationships in the luminal structure and corresponding branching region in the branching luminal structure anatomy. Unlike the navigation with the use of position sensors relied on in related art, navigation with image guidance does not necessarily require the knowledge of the exact anatomy of the lumen tree, provided that identifiers of each branch in the topological model are determined Neither there is a need in the image-guided navigation to achieve exact registration of the luminal structure model with respect to the 3D reference frame (in practice, such exact registration typically requires tracking and compensation for the motion of the patient). These are significant advantages of the navigational methods of present invention over the systems and methods of the related art (such as that discussed in U.S. Pat. No. 7,233,820, for example). On the other hand, in contradistinction with the endoscopic image guided navigation of the prior art, the probes of the present disclosure are structured and enabled to provide volumetric images of the branching luminal structure, which volumetric images contain ranging information. This means that i) the data contained in these volumetric images can be used to construct identifiers of each branch in the topological model of the luminal network, thereby significantly improving efficiency and reliability of navigation, and ii) exact position of the distal tip relative to the local structure of branches visible in the volumetric images can be obtained providing feedback for the distal tip manipulation from the proximal end. In addition, as will be described below, absolute, or global position of the distal end relative to the 3D reference frame of the gross anatomy of the patient body is enabled beyond the reach of the imaging depth of the probe. Tracking the absolute (or global) position of the distal end of the probe (in a luminal tree and relative to the 3D reference frame associated with gross anatomy of the luminal branching structure and the patient body) with the image-guided navigation still remains advantageous in that it may facilitate the detection and correction of gross navigational errors. It also improves efficiency and reliability of the navigation. Accuracy requirements for such image-guided tracking can be significantly reduced, as compared to those of the related art. While the following description focuses on navigational systems and methods that rely on imaging only, the use of the discussed elements and methods in combination with fluoroscopic and/or electromagnetic (EM) position sensors for gross identification of the absolute position of the distal end of the probe system remains within the scope of the present invention.

Figure 7:
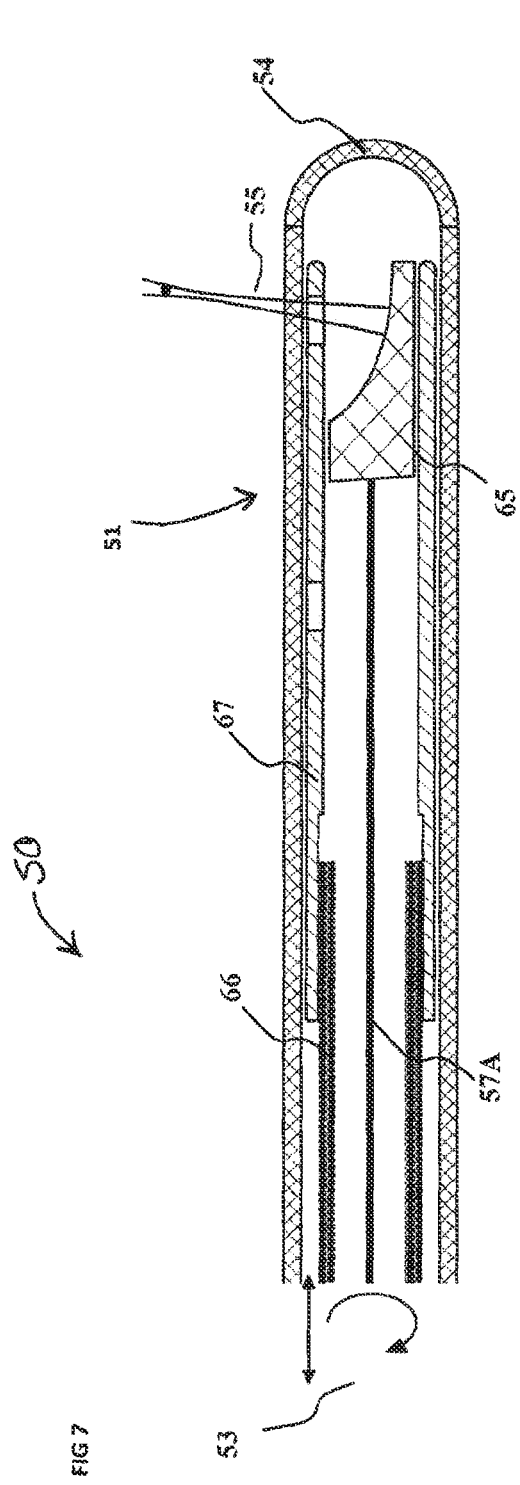
FIG. 7 is a diagram of the embodiment of an imaging probe of FIG. 2A having capability of transmitting ultrasound energy.

Ultrasound-Based Probe Component. FIG. 7 shows details of an embodiment of the distal end 51 of the probe 50 of an apparatus utilizing ultrasound energy (for example, at frequencies of 15 MHz and higher) for imaging of the ambient medium. At least a portion of the sheath 54 at the distal end 51 is sonolucent (translucent for an acoustic signal) and substantially matched in acoustic impedance with liquid that fills the lumen containing the shaft 53. There is variety of plastic materials that satisfy the above requirements with one example being polyethylene and the filling liquid can be water or mineral oil. The outer sheath 54 may optionally include marks or tags at the proximal end 52 facilitating the accurate determination of a length at which the probe 50 is inserted into a lumen in operation, as well as radio-opaque marks at the distal end 53 to facilitate fluoroscopic guidance.

In an embodiment using the ultrasound, the means for coupling energy contained in the shaft 53 includes at least one ultrasound transducer 65 that emits and receives the ultrasound energy 55. As long as sufficient efficiency of conversion is provided, piezoelectric materials such as barium titanate, lead zirconate titanate, lead metaniobate, and PVDT can be used for fubriation of the transducer 65. As shown, the focusing element and the directing element are combined by appropriately shaping the surface of the transducer 65. Alternative arrangements of structuring the means for delivery of energy can also be employed. For example, the use of a separate acoustic lens (made from material that is acoustically matched with the material of the transducer) and/or the use of the separate directing element (for example, in the form of an acoustic mirror made from material with large acoustic mismatch with respect to the ambient medium such as liquid associated with the target lumen). The electrical signal from the transducer 65 is delivered to the imaging console 100 of FIG. 1 via the energy guide 57. The energy guide 57 includes a standard coaxial cable 57A containing a core wire, insulation layers, and braided shield. Alternatively or in addition, the energy guide 57 may include plurality of electrical wires to connect with more than one transducer and/or bending actuators described below.

The coaxial cable 57A is shown to pass through a torque coil 66 that includes at least two layers of stainless steel wires wound in the opposite directions, to improve rotational properties of the shaft 53 and provide further shielding for electrical signals passing along the coaxial cable 57A.

The torque coil 66 is attached to a protective tube or body 67 (which secures the transducer 65 at the distal end 51 of the shaft 53) and to the mechanical coupler 62 at the proximal end (see FIG. 2A). The torque coil 66 may be optionally equipped with a stopper (made, for example, of a short piece of rigid metal tubing) at the proximal end to interface with rotational seals and translational seals. Such seals preferably include commercially available o-rings or commercially available leap seals or their combination and serve to prevent leaks of the liquid disposed inside the probe 50. Optional journal bearing, ball bearing, roller bearing secured to the hub 60 of FIG. 2A may be used at the proximal end 52 of the probe 50 to stabilize the stopper of the shaft 53 relative to the hub 60 to improve sealing.

The imaging console 100 for use with an embodiment of the imaging apparatus employing an ultrasound-based probe 50 is substantially similar to that of FIG. 2B. Here, the rotary joint 107 may include a commercially available electrical rotary joint such as, for example, an MI-10 series coaxial rotary joint supplied by MI Technologies of Suwanee, Ga. Information about the depth of the interrogated medium may be encoded by different time-of flight of the returned acoustic signal from different tissue depths and can be decoded (range compressed), for example, with the use of a matched-filtering algorithm (similar to that used in radars and/or sonars) or another method used in a field of medical imaging.

Alternatively or in addition, an embodiment of the ultrasound-based version of the probe 50 of FIG. 7 can employ a non-mechanical scanning method by, for example, utilizing a plurality of stationary ultrasound transducers (or a multi array transducer) at the distal end of the probe. In one incarnation, such transducer-placement can be effectuated on the side of the probe or in front of the probe. Then, by supplying specific sequence of signals to transducer(s), the focal region of the focused beam of energy can be scanned without rotating the shaft, according to a so-called synthetic aperture focusing approach. The advantage of using arrays of transducers is higher scanning speed and the possibility of switching remotely between difference views. The combination of rotational transducer and stationary multi-array transducer can be used to switch between radial (side-looking) imaging mode and linear, more forward looking mode.

Both the imaging based on magnitude analysis of acoustic return (that interrogates the echogenicity of the target tissue) and the imaging based on acoustic Doppler contrast (that interrogates the motion of the tissue) can be used for the purpose of this invention, whether or not complemented with the use of exogenous contrast agents as known in the art. The contrast agents enhance the magnitude of acoustic echoes, thereby improving sensitivity for echogenicity and Doppler contrasts. Tissue-specific ultrasound contrast agents (which may advance the assessment of certain organs by improving the image contrast resolution through differential uptake) include but are not limited to Albunex and Optison (provided by Molecular Biosystems in the U.S.), and Echovist and Levovist (by Schering, in a number of European countries).

The spatial resolution of imaging with the use of ultrasound is limited by the shortest available acoustic wavelength, which in turn is limited by the transducer's bandwidth and ultrasonic attenuation of high frequency ultrasound in the target tissue. Practical ultrasound imaging in a biological tissue has resolution on the order of 100 microns, which sometimes may not be sufficient to resolve details of tissue structure. In addition, the ultrasound is deficient in that it does not penetrate air-filled spaces; to compensate for such short coming, a physical contact between the probe and the tissue or use of liquid-filled balloons may be required.

Optical Probe Component. The optical energy (understood to be UV, visible or NIR optical radiation with wavelengths in the range 0.4-2 um) is more than two orders of magnitude shorter than the acoustic wavelengths. As a result, the spatial resolution of optical imaging is much higher than that of the ultrasound imaging system. Additional advantage of optical imaging is availability of more types of contrast such as spectral or polarization contrast. Yet another advantage of optical imaging is the ability of optical energy to propagate without attenuation through the air.

Figure 8:
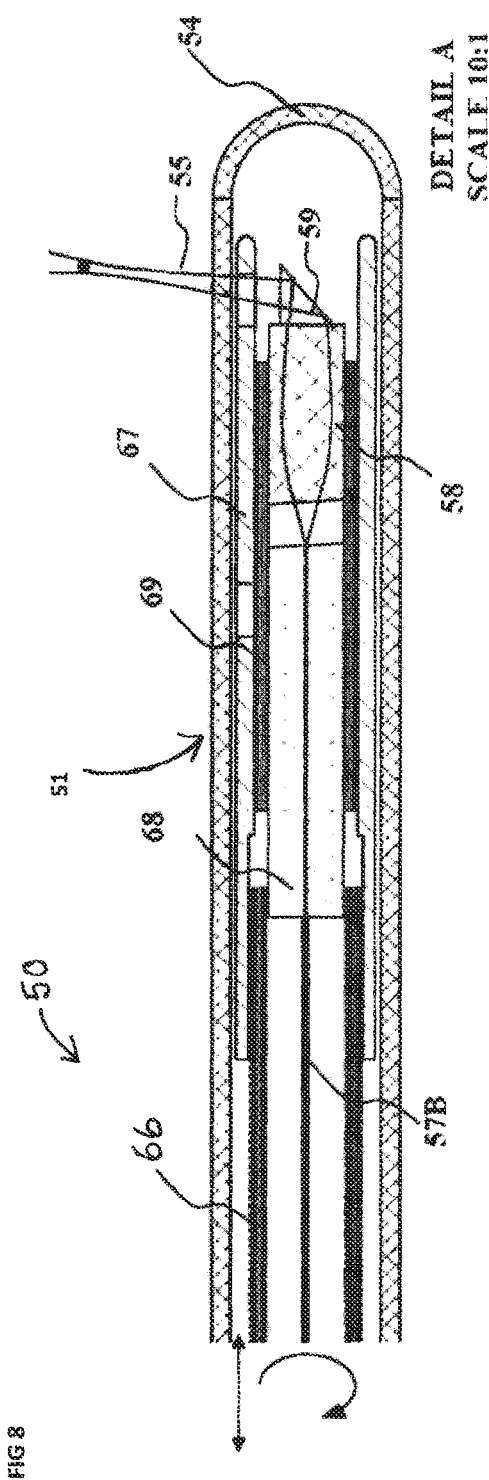
FIG. 8 is a diagram of the embodiment of FIG. 2A having capability of transmitting optical energy.

FIG. 8 illustrates an example of a distal end 51 of the optical version of the high-resolution probe 50. At least one portion of the probe's outer sheath 54 sealed at the distal end 51 is substantially optically transparent in at least one portion of the optical spectrum to minimize attenuation of the optical energy transmitted through the sheath. Biocompatible transparent plastic materials for fabrication of the outer sheath 54 of the optical probe include nylon, pebax, and fluoroplastics that can be used for fabrication of the outer sheath 54 in this embodiment. Sealed lumens in the body of the optical probe of FIG. 8 can be filled with air or other transparent gases, or transparent liquids such as water or transparent mineral oil. The outer sheath 54 may further include marks at the proximal end 52 for accurate determination of insertion lengths and radio-opaque marks at the distal end to facilitate the fluoroscopic guidance of the probe.

The embodiment of FIG. 8, when operably appended to the console 100 of FIG. 2A, channels light between the probe distal end 51 and the module 120 through the energy guide 57B (such as any of wide variety of optical waveguides or optical fibers) towards the focusing element 58 that is configured as part of a transceiver and terminates the energy guide 57B. Examples of the optical energy guide 57B include a single-mode optical (SM) fiber, an elliptical core fiber, a polarization preserving (PM) fiber, a multimode-mode (MM) fiber, a micro-structured or photonic crystal fiber (PCF), a multi-core fiber, fiber bundles or a plurality of separate fibers fabricated by any standard fiber-optic processes. The combination of the above optical waveguides or their splicing in one waveguide can be used. The focusing element 58 concentrates the optical energy 55 to spatial dimensions required for the high-resolution imaging (for example, down to less than 200 um and preferably less than 20 um). As shown, the focusing element 58 is attached to a ferrule 68 that holds the optical fiber 57B with an auxiliary mounting element 69 (such as a metal or glass tube), which in turn is mounted inside the protective body 67.

FIGS. 9A, 9B, 9C, 9D, and 9E illustrate several embodiments of the focusing element 58 in cooperation with the related elements of the optical probe 50 of FIG. 8. The focusing element 58 can be an optical lens directly attached to the fiber 57B by fusion splicing or adhesive bonding or, alternatively, it can be attached to the guide 57B via an intermediate mounting element 68, as shown in FIGS. 9A-9D. In particular, the optical lens can be a GRIN lens 58A (shown in FIG. 9A); or a refractive micro-lens 58B (fabricated by polishing, tip melting, selective etching and then secured to the fiber, or formed directly on the fiber by jet printing, by tip melting, by polishing the fiber end or by selective etching; shown in FIG. 9B); or a diffractive lens 58C (in the form of a micro Fresnel lens or chirped grating lens formed by, for example, binary and/or gray-scale lithography; illustrated in FIG. 9C but directly attached to the fiber by fusion splicing or adhesive bonding or attached with the help of the separate mounting element). In reference to FIGS. 9B through 9D, in some embodiments of the probe 50 a glass cylinders 68A can be disposed between the optical guide 57B and the focusing element 58A, 58B, 58C to improve the focusing of the optical radiation. In reference to FIG. 9E, the focusing element can also include a reflective lens or a curved mirror 58D polished on the glass cylinder 68A. The hybrid combinations of refractive, GRIN and diffractive lenses and curved mirrors can also be used to improve focusing properties of the optical probe. At least one focusing element described above may be separated from the shaft 53 and disposed in the outer sheath 54.

Figure 10A:
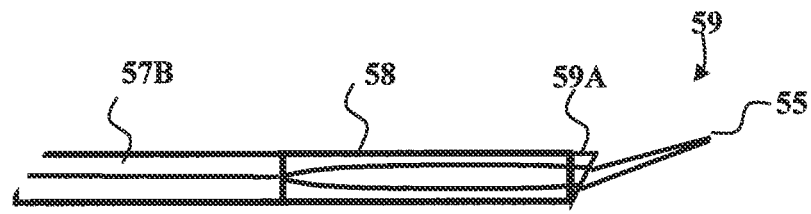
FIGS. 10A-10C show several embodiments of an energy coupling (energy directing) element for use with the probe of FIG. 8.
Figure 10B:
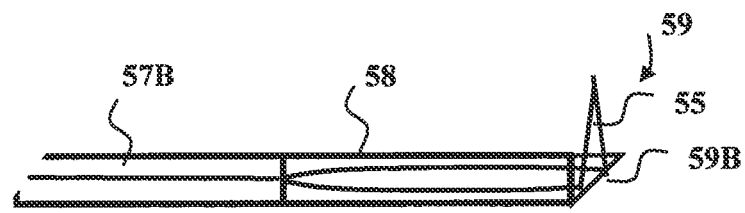
Figure 10C:
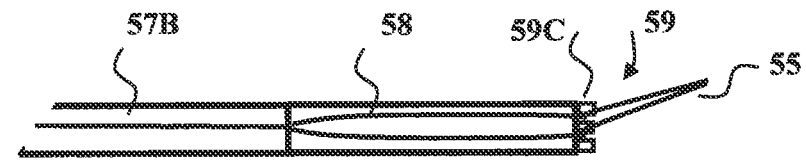

FIGS. 10A through 10C illustrate embodiments of the energy directing element 59 of the optical probe 50 of FIG. 8. The directing element 59 may include an optical refractive micro-prism 59A, or a reflective micro mirror or micro-prism 59B secured directly to the focusing element 58 with fusion splicing or adhesive bonding or with the help of the mounting element (not shown). Focusing elements with at least one substantially flat surface such as GRIN lens, or diffractive lens are particularly suitable for the arrangement with direct attachment of the directing element 59 to them. The energy directing element 59 include a diffractive element 59C such as a simple diffractive grating or more complex binary optic element attached directly or indirectly (through the focusing element 58) to the energy guide 57B with fusion splicing, adhesive bonding, or with the help of an auxiliary mounting element. Alternatively, as shown in FIG. 10C, the diffractive energy directing element such as the element 59C is formed directly on the guide 57B or the focusing element 58 using micro-fabrication methods. Alternatively, combinations of prisms, mirrors and diffractive elements can be used with at least some of the directing elements 59 disposed in the sheath 54 without being connected to the shaft 53. In a related embodiment, the energy directing element 59 and energy focusing element 58 can be combined or integrated into a single element, for example by polishing and then optionally coating tilted, refractive and/or reflective surfaces on the optical lenses; by forming refractive and/or diffractive lenses on tilted surfaces of glass rods by polishing, etching or other known methods; by forming curved tilted surfaced on optical elements, which then can be coated or used in a total internal reflection mode as focusing mirrors. In some embodiments at least one implementation of the optical energy directing element described in reference to FIGS. 10A through 10C is disposed separately from the shaft 53 and in the outer sheath 54. In some embodiments of dual (or multiple) view probes, at least one surface of the directing element 59 splits the energy beam and forwards a portion of it in the forward direction while redirecting the rest in the side view direction. Such beamsplitting can occur on the surfaces of the refractive micro prism 59A naturally via Fresnel reflection, or it can be enhanced and controlled by depositing appropriate optical coatings to effectuate dichroic (spectral) beamsplitting, polarization beamsplitting. Such coatings that split different spectral components (dichroic beampsplitters) or sptail-pattern-type beamsplitting by redirecting chosen portions of a wavefronts (in a fashion of a polka-dot beamsplitter) as known in the art.

Figure 11A:
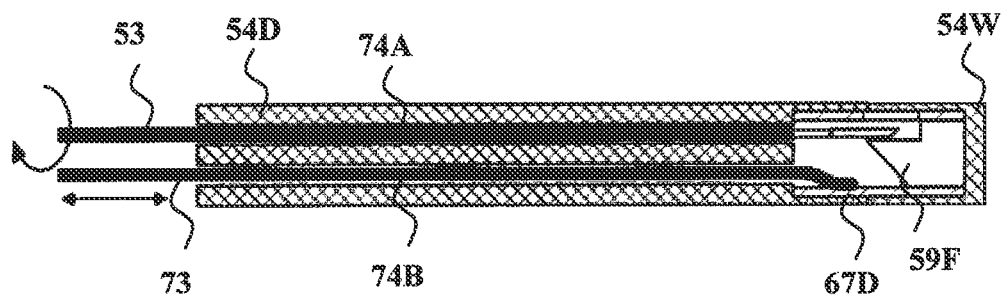
FIGS. 11A, 11B, 11C, 11D, 11E show embodiments of a probe characterized by a combination of side-imaging and forward-imaging capabilities integrated with a probe-steering means.

Referring again to FIG. 8, the embodiment of the optical probe 50 can be used directly as a component of the side-imaging probe 50B from the set of FIG. 5 such that the cross-sectional and/or volumetric images are produced by mechanical scanning of the focused optical energy while rotating and/or translating the shaft 53 in the hollow of the sheath 54. The incorporation of the torque coil 66, juxtaposed with the protective body 67, improves the uniformity of rotation (in a fashion discussed above in reference to FIG. 7), and the means for steering the embodiment of the probe (discussed below) can be optionally incorporated) to make the embodiment angularly steerable. For example, when using the steering means of FIG. 4A with this probe, the sheath 54 of the probe can be a sealed five-lumen catheter with the shaft 53 disposed in the central lumen and the pull wires disposed in the other four lumens. It is also possible to add a forward-looking imaging capability to the probe of FIG. 8 already equipped with the steering means, by disposing energy-directing element(s) in the stationary sheath 54. So modified probe component of FIG. 8 is suitable for use as the probe 50C of FIG. 5 and is exemplified in FIG. 11A. Specifically, FIG. 11A shows, cross-sectionally, a distal end of a dual lumen sheath 54D, with the rotating shaft 53 disposed in first lumen 74A and the pull wire 73 disposed in second lumen 74B. The pull wire 73 is secured by adhesive and/or soldering to a thin protective tube 67D made from glass or stainless steel. The tubing 67D is, in turn, secured to the sheath 54D with the help of a transparent cap 54W, which can be made from the same material as the sheath 54D and bonded to the sheath with adhesive or thermal fusion. To steer the distal end of the probe in the arrangement of FIG. 11A, the pull wire 73 is pulled at the proximal end with a handle (not shown). Secured to the tubing 67D is also a stationary directing element 59F, for example in a form of a glass rod polished at about 45 degrees at one end with additionally polished notch to accommodate the distal end of the rotating shaft 53. During the rotation of the shaft 53, the optical energy emitted from the shaft 53 can impinge on the 45-degree-inclined surface of the energy directing element 59F, to be directed forwardly with respect to the probe to produce a forward scanning pattern. At the same time, when the optical energy impinges on the walls of sheath 54D, the cap 54W or protective tube 67D directly, a side imaging (or radial) scanning pattern is generated. Notably, if the tubing 67D is made from non-transparent material such as stainless steel, a slot can be fabricated to let optical energy pass through to generate the side imaging scanning pattern.

From the above description, other modifications to the arrangements with combination of rotating and stationary directing elements with further improvements can be derived. For example, the sheath 54 can be a five-lumen structure with the rotating shaft 53 disposed in the sheath central lumen with four pull wired disposed in the other four lumens. In this case, the directing element 59F can be a glass tube polished at 45 degrees dimensioned to accept the rotating shaft 53 in its bore. The last surface of the directing element 59F can be also polished to have curvature and/or the directing element 59F can be made from gradient index material so that forward scanning pattern and side scanning pattern can have different working distance.

Figure 11B:
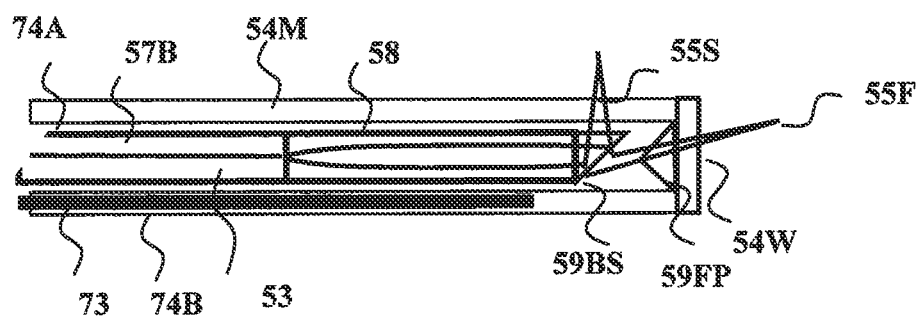

Alternative modifications to the arrangement with combination of rotation and stationary directing elements is shown in FIG. 11B. Specifically, FIG. 11B shows, cross-sectionally, a distal end of a multi-lumen sheath 54M, with the rotating shaft 53 disposed in its central lumen 74A and the pull wire 73 disposed in the second, off-centered with respect to the axis lumen 74B. The pull wire 73 is secured by adhesive and/or thermal fusion to the sheath 54 M distal end, preferably with a re-enforcing stainless steel pull ring (not shown). The sheath 54D has the transparent cap 54W, which can be made from the same material as the sheath 54D and bonded to the sheath with the use of adhesive or via thermal fusion. Secured to the transparent cap 54W is a stationary directing element 59FP, structured for example in a form of a 90 degree glass micro-prism. To steer the distal end of the probe in the arrangement of FIG. 11B, the pull wire 73 is drawn at the proximal end with a handle (not shown) and the whole probe body is rotated. During the rotation of the shaft 53, the optical energy emitted from the shaft 53 can impinge on the 45-degree-inclined surface of the energy-directing element 59BS, which additionally has a beamsplitting surface, so that a first portion of the energy 55F is directed in a forward looking direction to produce a forward scanning pattern, while and a second portion of the energy 55S is directed to the side of the probe to produce a side scanning pattern. In this arrangement side scanning pattern is radial or spiral. At the same time, the forward scanning pattern defines a forwardly directed cone. When the forwardly directed portion 55F of optical energy impinges on the cap 54W with the stationary directing element 59FP, the formed forward scanning pattern can be made more suitable for forward looking imaging. To achieve this, the rotating directing element 59BS and the stationary element 59FP should be structured to have similar or close, in value, deflection angles in the forward direction. The beam-splitting action of the directing element can be based on using different spectral bands of the optical energy or using different polarization.

Figure 11C:
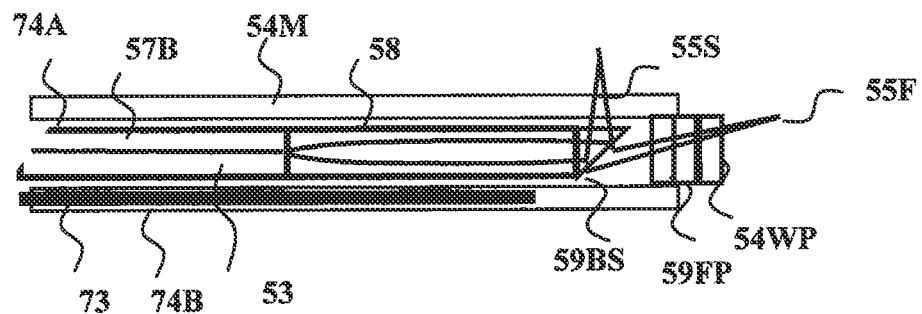
Figure 11D:
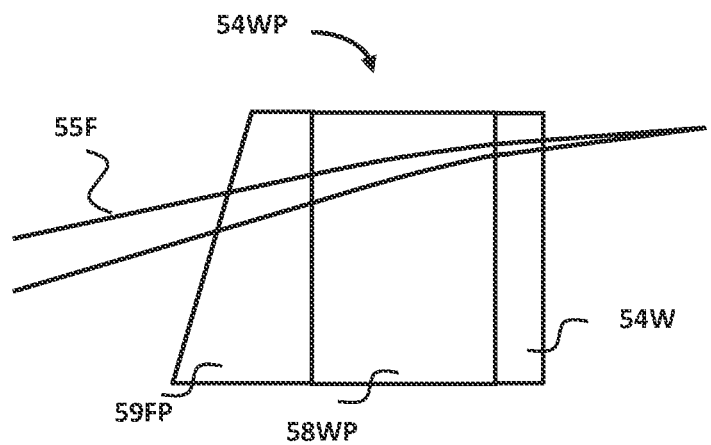
Figure 11E:
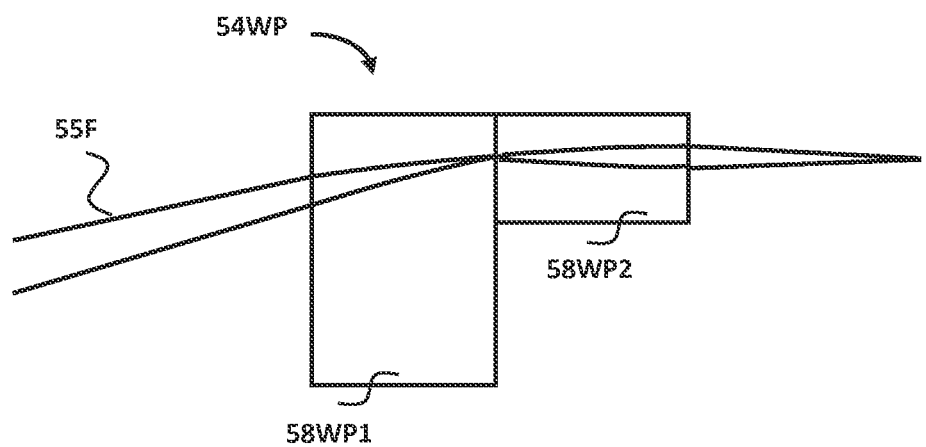

An alternative dual view implementation at the distal end of the probe is illustrated in FIG. 11C, where the outer sheath 54M incorporates a transparent cap 54WP that contains a plurality of stationary focusing elements. One of the focusing elements is a 1D focusing element (such a cylindrical lens or 1D GRIN lens) enabled to operate as a field lens, thereby substantially flattening the cone scanning pattern. Additional flattening of the scanning pattern can be obtained by offsetting the focusing elements that constitute the transparent cap with respect to each other. FIG. 11D shows an example of the transparent cap 54WP that contains a 1D focusing element 58WP in the form of a 1D GRIN lens (or, alternatively, a cylindrical micro lens) bonded to the cap 54W. The optical power and the position of the 1D focusing element 58WP with respect to the optical beam 55F is judiciously selected to substantially modify the scanning angle of the beam 55F in the focusing plane of the element 58WP (which is the plane of FIG. 11D). This "flattens" the scanning pattern making it easier to interpret. The optionally preceding the transparent cap 54WP directing element 59FP redirects the center of the scanning pattern in the chosen direction. An alternative example of the transparent cap 54WP is shown in FIG. 11E that contains the first stationary focusing element 58WP1 followed by the second stationary 58WP2 focusing element that is shifted laterally with respect to the element 58WP1. In this arrangement, the focusing element 58WP1 converts the angular cone pattern of scanning of the beam 55F to a circular scanning pattern of the focal point of the beam 55F. Because of the lateral offset of the second focusing element 58WP2, the focal points are always closer to the center of the focusing element 58WP2 in one plate (e.g. in the plane of FIG. 11E). Thus, the second focusing element 58WP2 relays the focal image of the energy portion 55F onto the tissue with angular scanning pattern that represents a portion of the cone that is significantly spatially flatter (for example, while not rotationally symmetric it has symmetry with respect to two mutually perpendicular planes) and, therefore, easier to interpret.

The use of the dual view arrangements exemplified in FIG. 11A-11C alleviates many practical restrictions imposed on accuracy and reproducibility of mechanical motion of optical elements at the distal end of the probe. Removing such restrictions facilitates the use of the steering means of the probe 50C for scanning as can be better understood by considering a modification of the arrangement of FIG. 11B as an example. Such modification includes fixing the shaft 53 in known relationship with the bending plane of the pull wire 73. Such relationship can vary except when the portion of the optical energy 55S is emitted at exactly 90 degree relative to the bending plane of the wire 73. Preferably, the shaft 53 is fixed to align the portion of the optical energy 55S within the bending plane of the pull wire 73. When the pull wire 73 actuates the bending motion of the probe's 50C distal end, the acquired A-lines in the forward direction have irregular spatial relationship with the tissue due to non-uniformities of the bending motion making the forward view image unusable for practical purposes. This non-uniformity can be corrected by tracking instant velocity and/or position of the probe's distal because the side view and forward view directions are in known spatial relationship with the steering motion directions. An example of such correction or re-mapping for the case of steering mechanisms of FIG. 11B is shown in FIG. 11F where the front view A-lines $F_n[m]$ are remapped using cross-correlation of the adjacent side-view A-lines $S_n[m]$. The exact definition of A-lines that represent reconstructed depth profile of back-scattered optical energy with depth pixels spacing $\delta\rho$ will be clear from the general description of optical coherence tomography and references below. The cross-correlation allows tracking instant position of the observed scene with respect to the probe's distal end and known geometrical relationship between the distal end displacements and its bending, and the rotational angles allow to relate the instant position of the observed scene to the polar and azimuth angles of the probe's distal end. Such known and predetermined geometrical relationship can be approximated by linear relationship as indicated in FIG. 11F. The application of method of performing forward view scanning as described in FIG. 11F for the case of other steering arrangement described in this application should be clear for person skillful in optical coherence tomography.

Figure 11G:
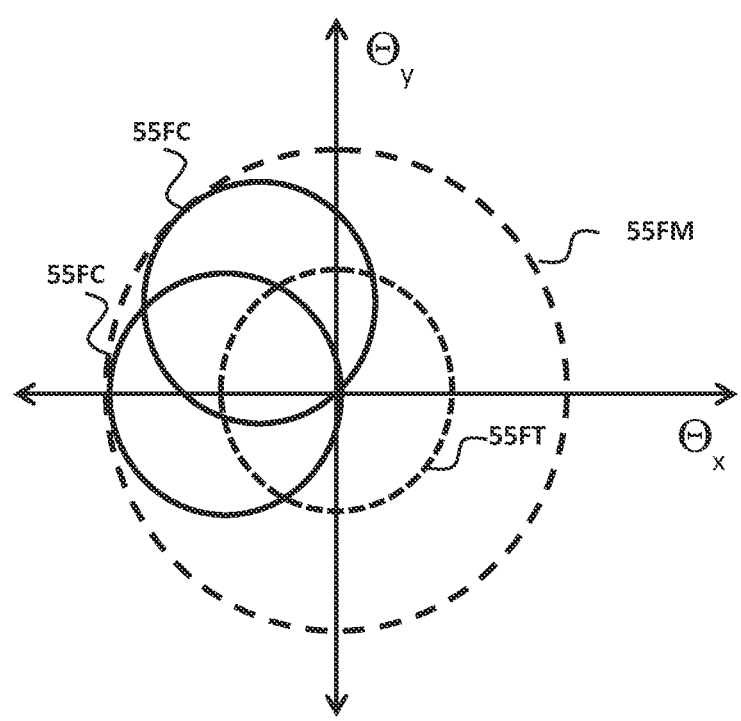
FIG. 11G is a diagram representing an example of a pattern of one-directional scanning and steering motion for generation of volumetric imaging with the embodiment of FIG. 11B.

It might be advantageous to combine a one-directional scanning with the use of the steering means to generate volumetric imaging. As an example, refer now to FIG. 11B where the shaft 53 is again allowed to rotate continuously while the distal end is steered. The scanned pattern in the forward view illustrated in FIG. 11G. This pattern includes a trajectory 55FC, caused by fast rotation of the shaft 53 with the optical energy deflected at angle $\Theta_{defl}$ with respect to the probe's axis. The trajectory 55FC is centered on a trajectory 55FT caused by the probe steering. In addition, the line 55FM illustrating the maximum deflection is shown in FIG. 11G. In absence of steering of the probe's distal end, the trajectory 55FC is a circular trajectory with known relationship between its azimuth angle and A-line number $\phi_n=\delta\phi \cdot n$ Due to non-uniformity of the steering, the trajectories 55FC are not spaced equally on the trajectory 55FT and have substantially irregular shapes making it impossible to remap the acquired image onto a useable representation. Using side-view images, however, it is possible to estimate an instant angular velocity of the steering and to correct this non-uniformity with subsequent re-mapping of the circles 55FC to regular shapes with equal spacing on the trajectory 55FT followed by re-mapping to easier-to-interpret volumetric image in Cartesian XY coordinates. FIG. 11H describes such re-mapping process in more detail algorithmically and the application of such remapping to other dual view and steering arrangements described in this application shall be clear from this example.

Figure 11I:
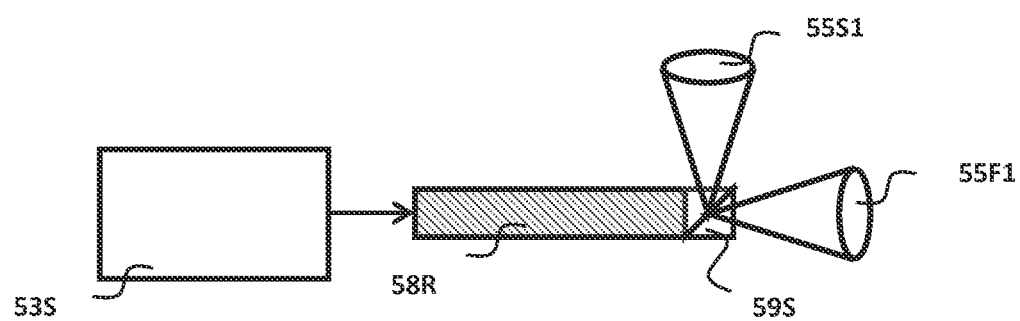
FIG. 11I is a diagram illustrating an embodiment of a probe of the invention.

When regions/scenes of interests are located in the forward directions in the tissue or in natural or surgically created cavities, the range of angles accessible for imaging can be restricted by limited dimensions of such cavities and/or limited dimensions of the entry ways. The viewing range can be effectively increased by using the dual-view arrangements and their combination with the steering means. This can be better understood by considering an example of a probe delivered to the region of interest via a hypodermic needle or similar narrow passages and adapted for dual-view imaging as illustrated in FIG. 11I. The probe of FIG. 11I has a stationary focusing element 58R which relays the optical energy scanned by a scanning unit 53S onto the tissue. This relay element 58R needs to pass via hypodermic needle or other narrow entry passage (not shown) and may be optionally enclosed in a protective sheath made of transparent material (not shown). Because the operation of the probe of FIG. 11I does not depend on its being flexible at the distal end, the focusing element 58R can be made of at least one or combination of GRIN rod lens(es). The scanning unit 53S can be the rotating shaft 53 of FIG. 11B, with the forward view optical energy portion 55F focused onto entrance surface of the stationary focusing element 58R and the side view potion 55S removed or decreased by proper selection of beamsplitting properties of the element 58BS of FIG. 11B. Also because the probe of FIG. 11I is not concerned with its cross-section dimensions outside of the hypodermic needle or other entrance passage, the scanning unit 53S can utilize a free space XY scanner such as, for example, a combination of galvo scanners. Attached to the focusing element 58R at the distal end is the beamsplitting arrangement 59S that further splits the optical beam delivered through 58R into portions 55F1 and 55S1, thereby effectively doubling the angular range available for imaging.

It shall be clear from the above descriptions that the dual view arrangements presented here can be easily modified into multi-view arrangements, for example by using additional beamsplitting surfaces of the directing elements disposed at different angles at the distal end of the probe 50.

It is appreciated, therefore, that embodiments of the present invention provide an advanced probe having an axis and structured to deliver energy in the first angular range or second angular range or both and generate a volumetric image in either forward or side view or in both simultaneously. This probe can be further structured to have a separate tubular body or outer sheath slidable along the main body of the probe to facilitate insertion of the probe and registration of the probe distal end with respect of the gross anatomy of luminal structure and the patient body as will be described below. This probe can be also structured to have at least one dedicated lumen as a working channel for delivery of instruments or for acceptance of separate steering means.

Embodiments of Navigation of a Probe of the Invention.

Figure 6A:
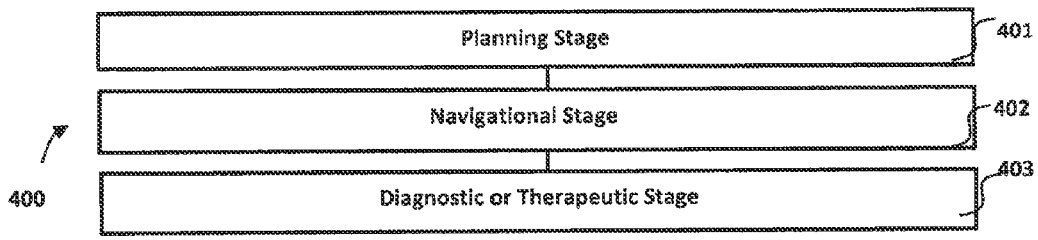
Figure 6B:
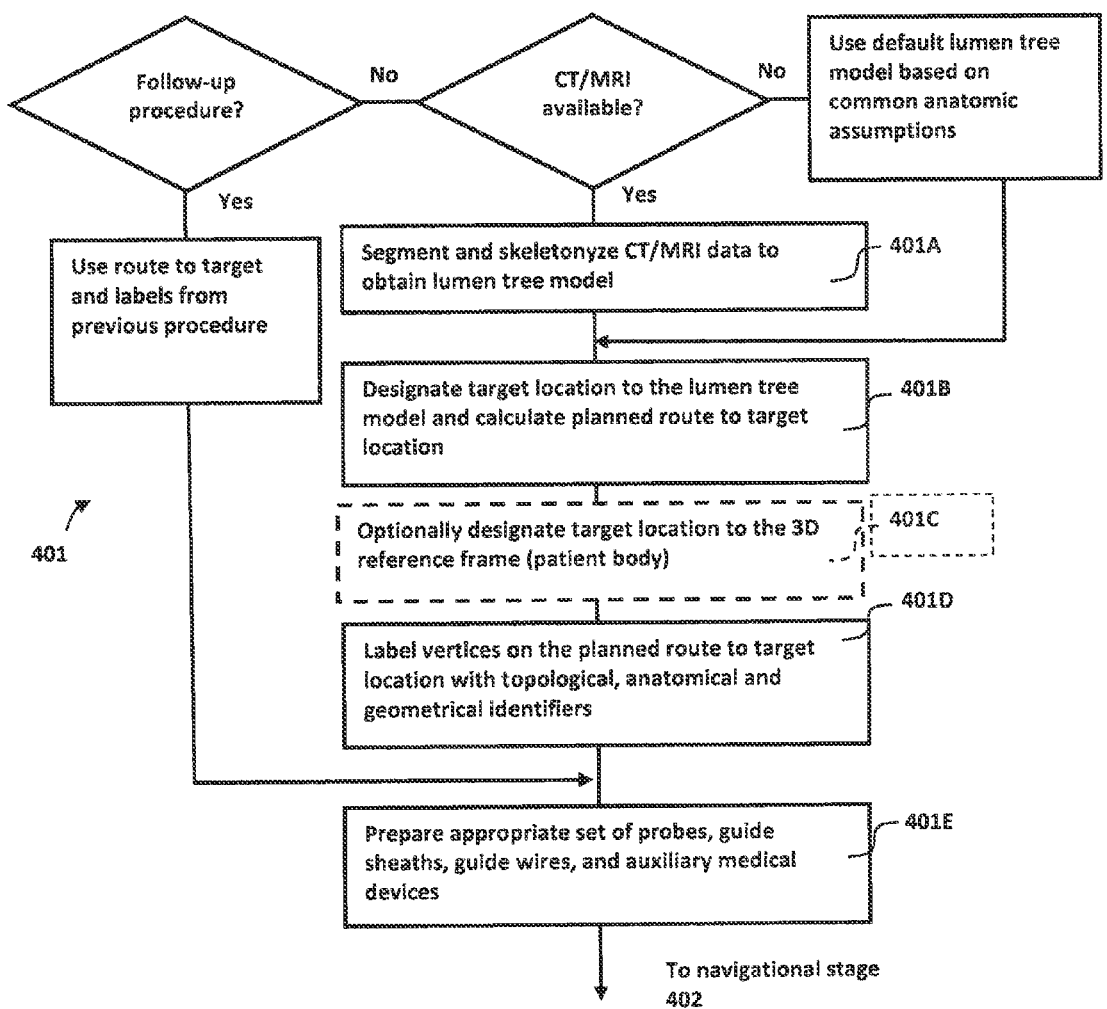

Referring now attention to description of navigational aspects of delivering probes to the target region according to present invention, FIG. 6A illustrates a flowchart of a diagnostic or therapeutic procedure of the present invention 400 that generally involves 1) a planning stage 401, 2) a navigational stage 402 and a diagnostic or therapeutic stage 403. During the planning stage 401 target location is designated relative to topological anatomical model of branching points, a route to the target location is identified, and the complete set, or a sub-set of probes, guide sheaths, guide-wires of FIG. 5 is prepared together with additional medical devices depending on lumen calibers on the identified route and the therapeutic and/or diagnostic needs of the procedure.

The planning stage 401 may also optionally include designation of the target location relative to the 3D reference frame related to gross anatomy of the patient body. Such 3D reference frame is used in the process of generating CT or MRI data and represent coordinates of the target location decoupled from local structure of lumen branches in the vicinity of the target, without specific designation of the target to particular branch or branching point of the luminal structure. More specifically, details of the planning stage 401 are exemplified in FIG. 6B that is referred now. First, previously acquired volumetric CT or MRI data is segmented and then thinned or skeletonized to produce a graph consisting of edges (segments) and vertices (bifurcation points) that represents the lumen tree structure (step 401A). Then, the target location is designated to the closest edge of the graph and the route to the target location is calculated or manually determined, for example, by searching through all the paths on the graph and finding one that connects the target location edge with the root edge of the lumen tree (step 401B), this route generally being represented by N vertices, or branching points. Several alternative routes can be pre-calculated at this step if designation of the target region to a graph edge is ambiguous, e.g., if the target region overlaps several graph edges. Optionally, the target location can be designated to the 3D reference frame of CT or MRI data or default anatomical model, for example by calculating center position $\vec{r}_{target}$ of target location and its spatial extent $\Delta r_{target}$ (step 401C) relative to the gross anatomy of the luminal structure and/or patient body (for example, the reference frame in which CT or MRI data has been acquired).

The next step (401D) is to label each vertex on the identified route using appropriate combinations of topological, anatomical and geometrical identifiers, the vertex label being also the label for the preceding edge of the graph. Many identifiers can be used to label vertices for the purpose of this invention as will be clear from description below that a) are robust with respect to patient body motion and b) can be conveniently determined in forward imaging view, side view imaging or both of the probes of the present invention. One example of useful combination of such identifiers is topological distance $n_{t,j}$ which is a number of edges from the start of the graph to the i-th vertex and the following preferred anatomical and geometrical identifiers. The preferred geometrical identifiers are geodesic distance to parent vertex, i.e. length of the preceding edge or segment and relative direction of the segment with respect to direction of its parent segment, $\Delta \vec{s}_i = \vec{s}_i - \vec{s}_{i-1}$. The preferred geometrical identifiers may further include the diameter of preceding branch $d_{f,i}$ averaged over pre-determined short distance in the vicinity of preceding vertex, the pre-determined short distance being determined by the forward imaging range of probes of the present invention, diameter inheritance factor $INH_{diameter,i} = sign(d_{f,i} - d_{f,sibling})$ indicating branches with largest and smallest diameter from the same parent, bifurcation angle $\Theta_i = a\cos(\vec{s}_i \cdot \vec{s}_{i,sibling})$, angle inheritance factor $INH_{angle,i} = sign(a\cos(\vec{s}_i \cdot \vec{s}_{i,parent}) - a\cos(\vec{s}_{i,sibling} \cdot \vec{s}_{i,parent}))$ indicating branches with largest and smallest deviation angle from their parents. The preferred anatomical identifiers may also include various anatomical landmarks in the lumen walls or their vicinity within the pre-determined short distance from the previous vertex. Such anatomical landmarks can be, for example, blood vessels, glands, or other sub-surface tissue structures and will be symbolically denoted as $\{Landmarks_{f,i}\}$. Preferred geometrical identifiers may further include diameters of preceding branch $d_{s,i}$ averaged over full length of that branch and various anatomical landmarks in the lumen walls or their vicinity along entire length of the branch $\{Landmarks_{s,i}\}$. The complete label for each vertex can be symbolically represented as follows $$\{label_i\} = \{n_{t,i}, \{INH_{dia,i}, INH_{angle,i}, d_{f,i}, \Theta_i, \{Landmarks_{f,i}\}\}, \{l_i, \Delta \vec{s}_i, d_{s,i}, \{Landmarks_{s,i}\}\}\},$$

were the first and the second sub-parenthesis represent forward-view and side view identifiers, respectively, as will be explained in further details during the navigational stage 402 description.

In case when CR or MRI data is not available, a default 3D model of lumen structure based on common anatomic assumptions can be used to generate a "best guess" initial route and to label branching points. In case when the procedure 400 has been already performed on the patient, the previously mapped route and its labels can be used. To summarize, the output of the planning stage 401 is N labels $\{label_i\}$, i=1,N on the graph model of the luminal anatomical structure and optionally target location and its extent $\{\vec{r}_{target}, \Delta r_{target}\}$. Finally, during the planning stage 401 appropriate set of the probes, guide sheaths and guidewires is prepared based on the planned route to the target locations together with required therapeutic or surgical devices (step 402E).

Figure 6D:
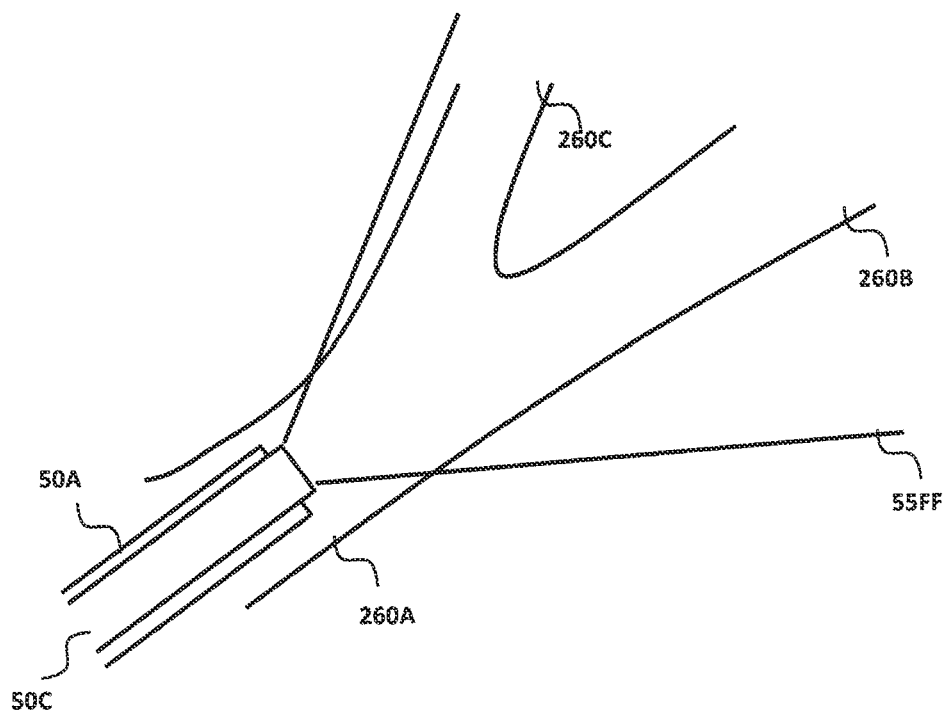
FIGS. 6D, 6E illustrate positioning of the probe in a luminal tree during the navigational procedure.

Referring now to FIG. 6C that shows the navigational steps recursively, the navigational stage 402 first includes a step 402A of identifying an anatomic feature on the planned route to the target location such as a lumen bifurcation and using this anatomic feature as an i-th fiducial. It is should be understood in this description that a known anatomical feature with known registration to patient body is identified as the 1$^{st}$ fiducial and subsequent fiducials are determined by recursions of navigational steps described here. The identification of the i-th fiducial can be symbolically represented by its label, $\{label\}_k$ and the registration of the i-th fiducial with respect to the 3D reference frame or patient body can be symbolically represented by a position vector $\vec{r}_{f,i}$ and two orthogonal unit vectors $\vec{s}_{f,i}$ and $\vec{n}_{f,i}$. For example, the position vector $\vec{r}_{f,i}$ can represent a characteristic bifurcation point of the branches, unit vector $\vec{s}_{f,i}$ can represent characteristic direction of the parent branch and the unit vector $\vec{n}_{f,i}$ can represent the normal to a characteristic plane containing children branches in vicinity of their bifurcation. During the step 402A the probe 50C of FIG. 5 is inserted in the luminal structure with the sheath 50A until all the children branches of the i-th fiducial can be imaged in the forward view of the probe 50C. The probe 50C and the sheath 50A of FIG. 5 will be further referenced in the description of the navigation stage 402 of FIG. 6C, but it should be clear that other combinations of probes of the present invention with guide sheaths and guidewires can be used. The ability of the probe 50C to produce quantitative cross-sectional and/or volumetric images in the forward direction with ranging information as well as with quantitative images of sub-surface features enables efficient identification of the correct target branches on the route to the target location, which can be easier understood by referring to FIG. 6D. In FIG. 6D, the probe 50C and the sheath 50A are located in a parent lumen branch 260A of the i-th fiducial identified to be on the correct route to the target location and having label $\{label\}_k$. Branches 260B and 260C are children branches to the parent 260A and therefore have $n_{k+1}$ topological distances in their labels. The probe 50C is sufficiently advanced in the branch 260A so that so that the both branches 260B and 260C are within imaging range of the probe 50C in the forward direction represented by a volumetric cone 55FF. The volumetric image obtained by the probe 50C can be processes with the same algorithms as in the planning stage during labeling of the planned route to the target location to yield probe-obtained forward-view identifiers {INH'$_{dia}$,INH'$_{angle}$,d'$_f$,Θ', {Landmarks'$_f$}} for the each branch 260B and 260C separately. Then these probe-obtained forward-view identifiers are correlated with their equivalents {INH$_{dia,k+1}$, INH$_{angle,k+1}$,d$_{f,k+1}$,Θ$_{k+1}$,{Landmarks$_{f,k+1}$}} of the k+1 label from the planned route to the target location. Higher correlation score identifies next target branch at this iteration step. In case when only default anatomical model is available only the diameter and the inheritance factors should be correlated with the labels. Even when exact anatomic model is available, often it would be also sufficient just to correlate diameter and angle inheritance factors as luminal anatomical structures are typically asymmetrically branching networks. Nevertheless, adding more robust forward-view identifiers is advantageous as it always increases efficiency of the correlation. Referring back to FIG. 6C the above-described correlation and identification procedures constitute step 402B.

Referring again to FIG. 6C, the navigational stage 402 of the method of the invention further includes a step 402C of steering the distal end of the probe 50C until the lumen of the k+1 branch identified as the target branch at step 402B is in the center of forward view so that the probe 50C can be safely inserted in the target branch. Then the probe 50C together with the guide sheath 50A is advanced into the k+1 target branch beyond the i-th fiducial while simultaneously imaging lumen walls in the forward view until a next anatomic feature such as next bifurcation is observed and all children k+2 branches are within forward view of the probe 50C. The step 402C further includes obtaining the side-view identifiers of the k+1 target branch and testing if the target location is reached. For this, the probe 50C is disengaged from the sheath 50A and is pulled back while acquiring a side view image of lumens in a spiral scan. Preferentially, the side view volumetric image includes lumen walls, sub-wall anatomical features and the stationary sheath 50A made substantially transparent. The side-view volumetric image of step 402C preferentially covers both k+1 target branch and k parent branch of the i-th fiducial. If presence of the target location in the side view volumetric image is confirmed at this step, the practitioner of the present procedure proceeds to the diagnostic and/or therapeutic stage 403. If not, the practitioner continues with navigational procedure 402, which further include step 402D of updating correlation by additionally correlating at least some of the side-view identifiers {l',Δ$\vec{s}$',d'$_s$,{Landmarks'$_s$}}' for the k+1 target branch with their equivalents {l$_{k+1}$,Δ$\vec{s}_{k+1}$,d'$_{s,k+1}$,{Landmarks'$_{s,k+1}$}}' If from the {label}$_{k+1}$. Specifically, extraction of the branch length, the average diameter and the anatomical landmarks is straightforward from the volumetric image and can be done by the same methods and algorithms as those used during the planning stage 401 of FIG. 6B. Disposing calibrated distance marks along the length of the sheath 50A can be advantageous to improve accuracy of the branch length measurement as they can be imaged simultaneously with the lumens to compensate for pull-back non-uniformity.

The preferred method of determining relative orientation of the k+1 branch with respect to the k-th branch, i.e. determining the direction vector Δ$\vec{s}_{k+1}$ is to register a forward view image in the k+1 branch when the probe is positioned in the k-th branch with the side view volumetric image of the k-th branch obtained by pulling back of the probe inside the sheath 50A. Additional orientation marks present at the distal end of the sheath 50A and visible in the forward and/or side view may further facilitate such registration. An alternative method of determining relative orientation of the k+1 branch with respect to the k-th branch is to use distributed bending strain sensors in the sheath 50A interrogating the sheath bending strain in two orthogonal directions. The distributed bending strain sensor readings are then converted to local bending angles which can be integrated over the length of the k-th and (k+1)-th branches to yield total bending angle of the sheath. The sheath bending angle can then be used as an estimate of the relative deflection angle of the k+1 branch with respect to k parent branch Δ$\vec{s}_{k+1}$. The distributed strain sensors can be, for example, four optical-fiber-based distributed strain sensors known in the art embedded in the sheath walls along the sheath length oriented at 0 degree, 90 degree, 180 degree, and 270 degree azimuthally. Yet, a strain sensing method that exemplifies best the aspect of the invention allowing determination of bending in the sheath 50A is to analyze the side view volumetric image obtained during the step 402C and to perform speckle correlation of the sheath wall images to determine the sheath bending state. Use of other distributed bending strain sensing methods will be then obvious from the description of this exemplified method. Specifically, a thing wire or fiber can be embedded in the sheath wall and used as orientation features to define the azimuth zero in the spiral scan, the orientation feature that having substation length (few tens of mm) covering typical lengths of branches in luminal anatomical structures. Four narrow azimuthal sectors around 0, 90, 180 and 270 degrees with respect to the orientation feature can be selected in the side-view volumetric image of the sheath 50A wall. Then the azimuthal sectors can be further divided longitudinally in short segments with pre-determined length and spacing among them. These azimuthally and longitudinally small regions can sense the sheath 50A strain when their images are speckle correlated with the corresponding images of unperturbed sheath. The images of unperturbed regions can be obtained and stored in the CPU memory before the start of procedure as a calibration step and the amount of longitudinal scale change, i.e. expansion or compression that maximizes the speckle correlation at each region can be used as a local strain reading.

The previously mentioned calibrated distance marks distributed along the length of the sheath can be used to help identify the strain sensing regions in the image for the speckle correlation analysis. Denoting the length of the m-th sensor and its strain readings as l$_{sensor,m}$ and ε$_{m,0°(90°,180°,270°)}$ respectively, and denoting sheath diameter as d$_{sheath}$, the total deviation angle in each orthogonal direction can be symbolically represented as $$\Theta_{0°} = \sum_{m=1,M} \frac{l_{sensor,m}(\varepsilon_{m,0°} - \varepsilon_{180°})}{d_{sheath}} \text{ and}$$

$$\Theta_{90°} = \sum_{m=1,M} \frac{l_{sensor,m}(\varepsilon_{m,90°} - \varepsilon_{270°})}{d_{sheath}},$$

where M is total number of strain sensing regions along the combined k+1 and k branches length. Typically, the advancing of the sheath 50A into lumens can be done with minimal twisting and therefore the azimuthal orientation of the outer sheath and the i-th fiducial is preserved. That is, the registration of the unit vectors $\hat{\Theta}_{0°,k}, \hat{\Theta}_{90°,k}$ to the i-th fiducial is known and therefore the relative deviation angle of the k+1 branch can be expressed as $$\Delta \vec{s}_{k+1} = \frac{(\Theta_{0°,k+1}\hat{\Theta}_{0°,k} + \Theta_{90°,k+1}\hat{\Theta}_{90°,k})}{\sqrt{\Theta_{0°,k+1}^2 + \Theta_{90°,k+1}^2}}.$$

The geometrical identifiers $l_{k+1}\Delta\vec{s}_{k+1}$ determined during step 402D also allow tracking of the absolute (or global) position of the probe, which in turn enables detection of gross deviation from the target region when the navigation algorithm 402 is lost. This can be done because on each step relative distance and orientation to the previous fiducial mark is determine and the absolute, i.e. relative to the 3D reference frame, registration of the orientation of the 1$^{st}$ fiducial is known. Thus the position of the probe distal end in k+1 branch and its position error can be optionally determined as $\vec{r}_{probe,k+1} = \vec{r}_{probe,k} + l_{k+1}\cdot\vec{s}_{k+1}$ and $\Delta r_{probe,k+1} = |\vec{r}_{probe,k+1} - \vec{r}_{target}|$, respectively.

Referring again to FIG. 6C, the navigational stage 402 further includes optional analysis of the absolute probe position. If the probe deviation is within pre-determined range from the target, for example smaller then pre-determined fraction of the spatial extend of the target $\Delta r_{probe,k+1} < \alpha \Delta r_{target}$, the practitioner may proceed to the diagnostic and/or therapeutic stage 403. If the probe deviation exceeds a pre-determined maximal deviation from the target $\Delta r_{probe,k+1} > \Delta r_{max}$, the gross error in navigational algorithms are detected and the navigational stage 402 should re-start from the step 402A with re-calculated, alternative route to the target location. The recalculation of alternative route can be also triggered by detection of maximal number of iteration exceeded, i.e. when the maximal number of tried branches significantly exceeds number of labels in the calculated planned route to the target location. If the navigational stage 402 is still active and is not considered lost after the above mentioned comparisons, the correlation score obtain in the step 402D for the k+1 branch is compared with pre-determine acceptance threshold. If the correlation score is above the acceptance threshold, the k+1 branch is identified as a next i+1 fiducial and the navigational stage 402 is re-iterated from the step 402A. If the correlation score is below threshold, the algorithm attempts to recover by testing each alternative k+1 branch by advancing in the alternative branches of the k+1 generations and re-iterating from step 402C. If this recovery step fails to bring the correlation score above the acceptance threshold, the navigational stage is considered lost and should re-start from the step 402A with a re-calculated alternative route.

Figure 6E:
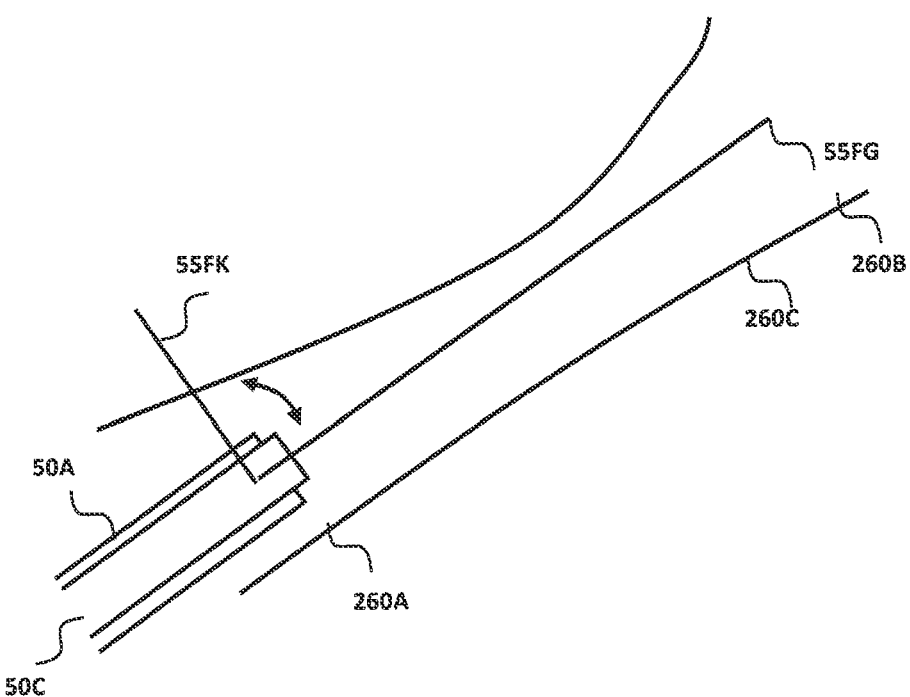

In some of embodiments of the imaging probe 50C, the forward scanning does not cover the complete 3D cone generative volumetric forward image but instead has substantially 2D scanning pattern in the forward direction. The use of the steering means and/or azimuthal rotation of the probe 50C, combined with side-view imaging, allows to use such 2D scanning in the navigation stage 402. Referring now to FIG. 6E that shows the probe 50C cross-sectionally in the plane perpendicular to the plane of bifurcation, e.g. perpendicular to the plane of FIG. 6D, the probe 50C of FIG. 6E has 2D scanning pattern 55FG in forward direction together with radial scanning pattern 55FK in the side view direction. While located in the branch 260A, the probe 50C can be steered "up" and "down" during imaging of the branches 260B and 260C, or alternatively it can be rotated azimuthally. It is possible to extract information from the 2D images in the cross-sections of the branches 260B and 260C that correlates with the identifiers from the labels of the planned route to the target location by known methods of morphometric analysis of features in the 2D images used in the field of image processing for histology. For example features that correlate with the diameter and angle inheritance factors can be easily determined especially when a convenient orientation of the cross-section with respect to the branches is obtained by steering and rotation of the probe 50C distal end. Yet, the preferred method of forward imaging with arrangements of FIG. 6E is to generate a volumetric image of the branches 260A, 260B and 260C with the forward scanning pattern 55FG while simultaneously continuously scanning the orthogonal direction ("up" and "down" of FIG. 6E) with the steering means of the probe 50C. To compensate for non-uniformity of steering or rotation to minimize distortions in the forward view volumetric image, a side view image of lumens walls obtained with radial pattern 55FK is used. Specifically, the correlation analysis of adjacent A-lines and B-scans of the side-view image (i.e. a frame-to-frame correlation) determines instant relative steering or rotational angle of the probe 50C relate to the branch 260A. The instant steering or rotational angle is then used to remap the B-scans of the forward view image.

Finally, during diagnostic or therapeutic stage 403 cross-section and/or volumetric images are taken in the target location, medication, ventilation, aspiration, or medical devices are delivered and guided. Further details of the image guidance of medical devices in accordance with the present invention will be clear from description of various embodiments of the probes of the present invention that follows.

It is appreciated, therefore, that embodiments of the invention provide a method for navigation of a high-resolution (and having side- and forward-oriented imaging capabilities) probe through or along the lumen tree such as to enable both the quantitative ranging and sub-surface imaging. The quantitative ranging includes collection of data representing absolute and/or relative separation between the probe and the location of a scattering point. The method includes designating a target location relative to the anatomical model of the branching points of the lumen tree and the 3D frame of reference, and identifying a route to the target location. The anatomical model may be obtained from prior acquired volumetric images or certain anatomic assumptions and/or models. The method additionally includes obtaining an image of a first anatomic feature (used as a first fiducial) with a defined registration to the 3D reference frame, and then advancing the probe to the next branching feature and obtaining an image of the next branching feature in the forward field of view of the probe. The method also includes determining unique anatomical identifiers of each branches associated with that next branching feature from the obtained 3D and sub-surface images, and correlating the determined identifiers with identifiers from anatomical model(s) of the tree to select the target branch based on such correlation. The method may optionally include obtaining a complete 3D and quantitative image of a portion of the lumen (between the next branching feature and the first fiducial) by a pull-back imaging, in order to extract the distance separating the corresponding points and the angular orientation of the next branching feature relative to the first fiducial, to register images of the next branching feature with the 3D reference frame. Furthermore, the navigation according to the method may employ steering of the distal end of the probe until lumen of the target branch is substantially centered, with respect to the probe axis, in the forward field of view, and then advancing the probe into the targeted branch. The next branching feature may be assigned to be a next fiducial point. Saving images and/or identifier information and repeating at least some of the above steps until the target location is reached is also within the scope of the method. Although the use of both forward view and side view is preferred method for efficient and reliable navigation, it is clear from the above description how to adapt the navigational method for using only forward view or side view identifiers and thus navigating using only forward view or only side view volumetric imaging. For example, when only forward view imaging is to be used, the step 402C should be modified to skip obtaining of the side view imaging and updating correlation with side view identifiers. When side view imaging only is to be used for navigation, the user of the probe may consider entering each tested branch to obtain a correlation score using side view identifiers and then repositioning the distal end to enter the target lumen that has been assigned with the highest score.
Embodiments of the Imaging Console.

Figure 12A:
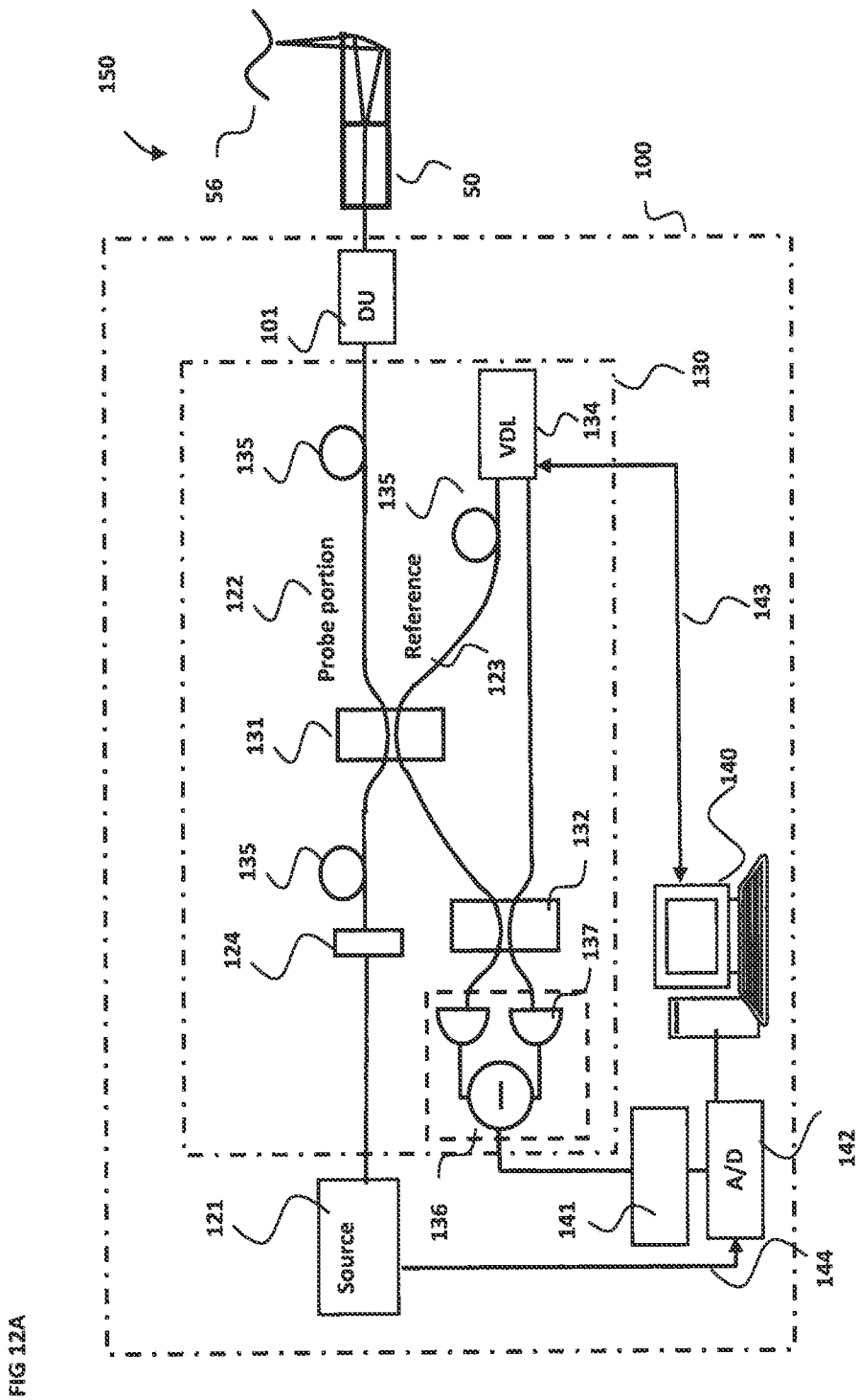
FIGS. 12A, 12B, 12BA, 12BB, 12C, 12D show embodiments for use with a system of the invention that employs a light-based imaging apparatus.

Turning now the attention to description of the imaging console for the embodiment of the probe that uses optical energy, the imaging console 100 of the imaging apparatus 150 can have arrangements shown in FIG. 2B. The rotary joint 107 of FIG. 2B can be a fiber optic rotary joint (FORJ) 107A commercially available for example from Princetel of New Jersey. The optical module 120 and its operation can be based on interferometric methods known as Optical Coherence Tomography (OCT). The methods of OCT that are described in U.S. Pat. Nos. 5,321,501 and 6,134,003 can be applied for the purpose of the present invention and are incorporated by reference herein in their entirety. Further modifications of the prior art for the purpose of the present inventions can be better understood if general description of OCT methods is given first. Specifically, exemplary implementations of the imaging apparatus 150 based on OCT with modifications of the present invention are shown in FIGS. 12A-12C and 13A-13F. In FIG. 12A the light from an optical energy source 121 is guided to an interferometer 130 where the light is split into a probe portion 122 and a reference portion 123 by an optical beamsplitter or optical coupler 131. The probe portion 122 is directed to the tissue 56 via the Drive Unit 101 and the probe 50. The returned optical energy from the probe portion 122 is guided back to the interferometer 130 where it interferes in an optical beamsplitter or optical coupler 132 with the reference portion 123 to produce an interference fringe pattern or an interferogram containing the depth-encoded tissue information. An optional polarization modulator or polarization switch 124 can be added to the interferometer input to toggle or modulate polarization state of the source light for various implementations of polarization sensitive imaging. All the components of the interferometer 130 can be made from off-the-shelf fiber optic components using standard single mode fiber. For example for the optical energy centered around the wavelength of 1.3 um the SMF-28 single mode fiber manufactured by Corning can be used.

There are three known types of OCT: time domain (TD-OCT), frequency domain (FD-OCT) and spectral domain (SD-OCT) and all the three can be used for the purpose of the present invention. In the TD-OCT the light source 121 is a broad band source with low coherence length such as commercially available superlumenecent diodes (SLED) from for example Inphenix of California. The optical path difference (OPD) between the probe and the references paths of the interferometer 130 varies rapidly in TD-OCT by means of a variable delay line (VDL) 134 to produce the interferogram. To ensure good visibility of the interferogram fringes, the returned probe and reference portions of light should be substantially in the same polarization, which can be achieved by using at least one polarization controller (PC) 135 disposed in the reference or the probe path. More controllers can be used to align polarization state in each path to be optimal for the fiber-optic components of the interferometer 130. The interferogram is detected by a balanced receiver 136 that consists of two well matched photo-detectors 137; alternatively one single detector 137 can be used. Then electrical signal from the balanced receiver 136 is optionally filtered and/or amplified by an electronics processing module 141, digitized by an A/D converter 142 and digitally processed by the CPU 140. The CPU can further synchronize VDL with A/D conversion by means of VDL control signal and VDL synchronization signal 143.

In the FD-OCT, the light source 121 is a frequency swept long coherence length source such as one commercially supplied by Thorlabs of New Jersey and the probe-reference OPD is kept substantially constant during the sweep time of the source. In this case, the interferogram is produces by changing instantaneous wavelength of the light source and is detected by the balanced receiver 136, optionally filtered and amplified by the electronics unit 141, digitized by the A/D converter 142 and processed by the CPU 140. In this case the CPU 140 also synchronizes A/D conversion with the source sweep rate by means of source to A/D sweep rate and clock synchronization signal 144. In some embodiments of FD-OCT, the broadband source combined with a dispersive optical element with high group velocity dispersion (GVD) can be used. In this arrangement, the dispersive elements spread different spectral components of the broadband source in time, producing a frequency sweeping source. An example of the broadband source for this arrangement is a white light continuum (WLC) source commercialized by Fianium, UK and an example of the dispersive element is a large dispersion micro-structured optical fiber or photonic crystal fiber described by A. Huttunen "*Optimization of dual-core and microstructure fiber geometries for dispersion compensation and large mode area*, Optics Express, Vol. 13, No. 2, p 627 (2005).

Figure 12B:
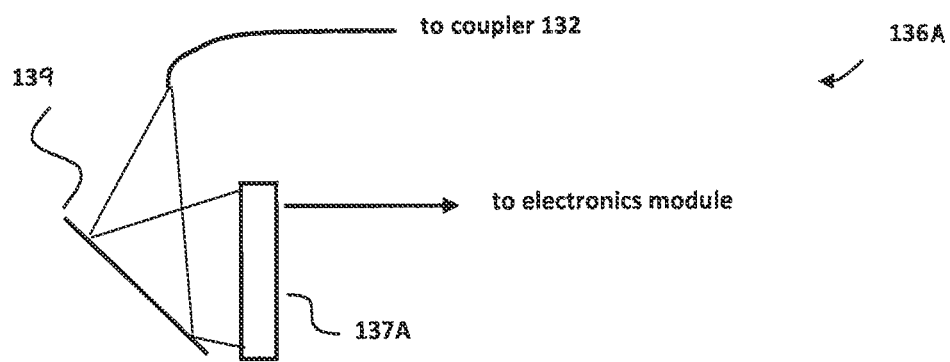
Figure 12C:
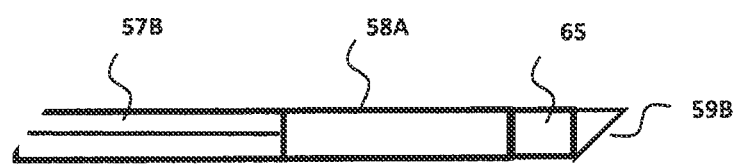
Figure 12B:
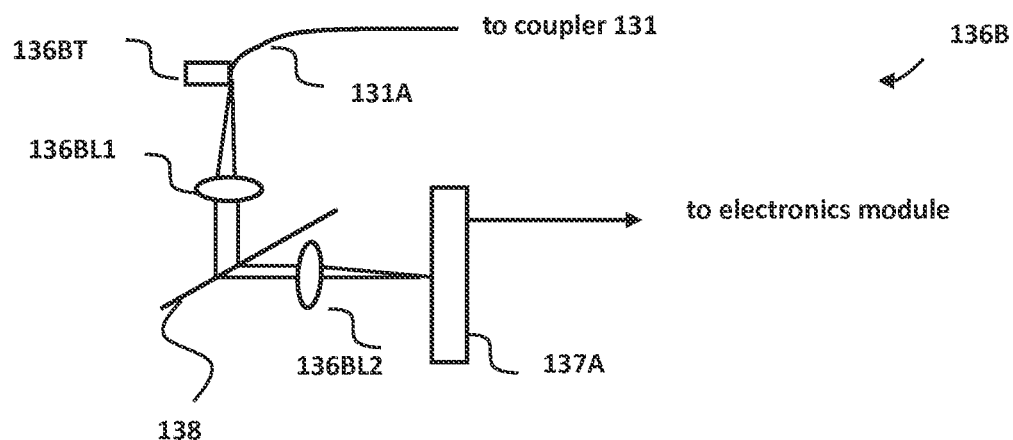
Figure 12B:
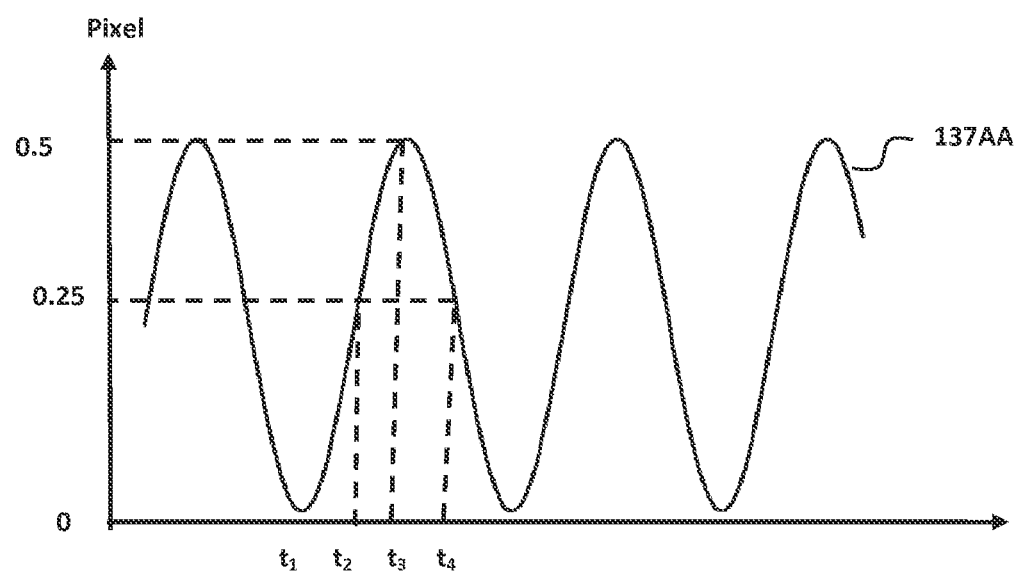
Figure 12D:
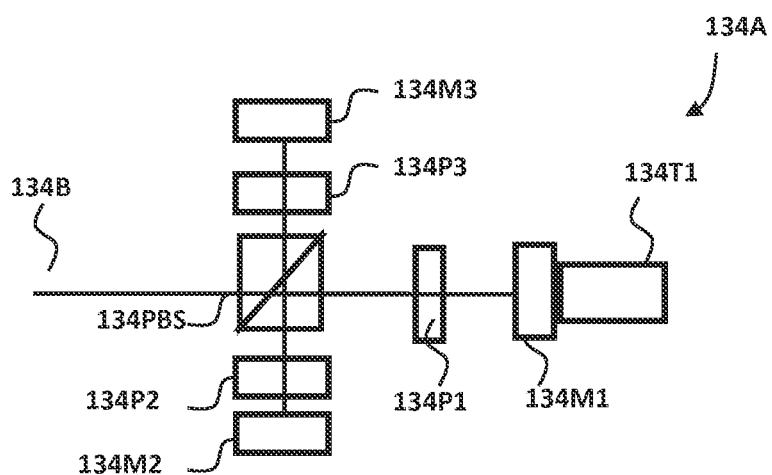

In the SD-OCT the light source 121 is, again, the broad band source such as, for example, a white light continuum (WLC) source comercialized by Fianium, UK but with the probe—reference OPD kept substantially constant and the interferogram is obtained by dispersing spectral components of the interferometer output with an arrangement 136A shown in FIG. 12B. The arrangement 136A consists of a grating 139 to obtain intensity of each spectral component with an array detector 137A and replaces the balanced receiver 136 in FIG. 17A for the SD-OCT implementations. The output of the array detector is then digitized by the A/D converter 142 and processed by the CPU 140.

One shortcoming of the SD-OCT is limited depth range caused by finite number of pixels of the array detector 137A. For example, the so-called Nyquist limit determines the maximal depth that can be imaged with SD-OCT. This deficiency can be reduced by using an arrangement 136B shown in FIG. 11BA that replaces the balanced receiver 136 in FIG. 17A for the SD-OCT implementation. Referring again to FIG. 11BA, the interferometer output is outcoupled into the arrangement 163A via an output fibers 131A of the coupler 131 (not shown). The interferometer output is then collimated by the collimating optical element 136BL1 onto the grating 138 and the light dispersed by the grating 138 is focused by a focusing element 136BL2 onto the array detector 137A. During operation the spectrally dispersed interferograms are acquired by the control electronics in the form of A-lines $A_n[m]$, n=0, 1, ... N−1; m=0, 1, ..., M−1 where N is number of A-lines and M is number of pixel elements of the array detector 137A. All M elemensts of the A-line are acquired simultaneously while each line is acquired sequentially. The fiber 131 is attached to a translational element 136BT that can laterally translate the outcoupling portion of the fiber 131 with respect to the optical axis of the element 136BL1. As a result of such translation the corresponding spectrally dispersed interferogram is transformed spatially on the array detector 137A with known transformational relationship with the translation of the element 136BT. Examples of such translation element are electrically drive piezo stacks or solenoids. Many other types of translators can be used as long as they result in sub-pixel translations of the interferograms on the array detector. The translation of the element 136BT can be done step-wise, for example by toggling between two positions that correspond to an unshifted interferogram an interferogram shifted by the distance equal to half pixel of the array detector. In this case when A-line acquisition is synchronized with the toggling of the translator, each subsequent A-line is half-pixel shifted with respect to the previous A-line. Modified A-lines $A_n^{ext}[m]$ with doubled range can be obtained by interleaving adjacent A-lines as follow $$A_n^{doube}[m] = \begin{cases} A_n[m/2] & m = 0, 2, \ldots, 2 \cdot (M-1) \\ A_{n+1}[(m-1)/2] & m = 1, 3, \ldots, 2 \cdot (M-1) - 1 \end{cases}$$

Alternative exemplary embodiment of using arrangement 136B illustrated in FIG. 12BB is to translate the element 136BT continuously with periodical motion represented schematically by curve 137AA of FIG. 12BB that corresponds to the shift of the interferogram of the array detector 137A. The amplitude of the motion 137 can be selected greater or equal to half of the pixel spacing of the array detector 137A. Also, acquisitions times of A-lines t1, t2, it can be synchronized with the repetion rate of the motion 137AA so that at each time $t_i$, the position of interferogram corresponds to predetermined interpixel shift with respect to initial position. For example there could be three A-lines acquired during the motion of the translator from two extreme positions as illustrated in FIG. 12BB, with the first and the third A-lines corresponding to 0 and half pixel shifts, respectively. In this case the modified A-lines with tripled depth range can be constructed by interleaving the points of adjacent A-lines as follows.

$$A_n^{tripple}[m] = \begin{cases} A_{t_i}[m/3] & m = 0, 3, 6 \ldots, 3 \cdot (M-1) \\ A_{t_i}[(m-1)/3] & m = 1, 4, 7 \ldots, 3 \cdot (M-1) - 1 \\ A_{t_i}[(m-2)/3] & m = 2, 5, 8 \ldots, 3 \cdot (M-1) - 2 \end{cases}$$

Another approach to improving the depth range of SD-OCT with the arrangement 136B is to replace the output fiber 131 with a fiber array of K fibers (not shown) with spacing between each fiber of the fiber array corresponding to predetermined interpixel shift of the interferogram on the array detector 137A. In this embodiment the fiber array is connected to the coupler 131 with 1:K fiber switch (not shown) synchronized with the electronics module so that during any given A-line acquisition the output of the interferometer is outcoupled from single pre-determined fiber of the fiber array. In this case each A-line will have corresponding interpixel shifts and reconstructed A-lines can be obtained as described previously.

One problem with application of OCT for endoscopic imaging of luminal anatomic structures is sensitivity of polarization and phase of the probe portion 122 of light to bending, rotation, and temperature of the probe 50. Uncontrollable changes of these parameters caused in particular by fast rotation and translation of the probe 50 during scanning may result in instabilities affecting quality of imaging. For example instabilities can be caused by polarization fading, i.e. by loss of the interferometric fringes visibility when the probe and the reference states of polarization (SOPs) become orthogonal. Therefore methods to address these image instability problems are needed.

Polarization fading can be addressed by using a polarization diversity detector in place of the balanced receiver 136 of FIG. 12A. The polarization diversity detector is commercially available from Thorlabs of New Jersey and allows simultaneous detection and processing of two SOPs at the output of the interferometer 130. The interference signal in each SOP at the output of the polarization diversity detector can be digitized by two channels of the A/D converter 140, while the electronics module 138 filters and amplifies inputs to each channel of the A/D converter 141. The polarization state of the reference light can be controlled by the polarization controller 135 to ensure that there is sufficient reference power in each polarization of the diversity detection. Then the CPU 140 processes the two channels independently and can generate sum of the processes signals that does not depend on the polarization state and thus is free of the polarization fading.

The direct implementation of polarization diversity detection for the case of SD-OCT can be impractical due to high cost of such detectors. This issue can be addressed by imposing differential phase modulation onto orthogonal SOPs in the reference arm of the interferometer 130. For example two linear polarization states (s and p) in the reference arm of the interferometer 130 can be phase modulated at two distinct frequencies $f_s$ and $f_p$ so that interferograms for the s and p polarizations have carrier frequencies $f_s$ and fp, respectively. Then the standard demodulating steps such as, for example, multiplication by a sine function with the carrier frequency followed by low pass filtering can decouple the signals for s and p polarization. To implement such modulation an arrangement 134A shown in FIG. 12 D can be attached to the VDL 134 of the interferometer 130 retro-reflecting the energy reference portion towards the coupler 131. Specifically, the optical energy enters the arrangement 134 having linear polarization aligned to pass through a polarizing beampsplitter (PBS) 134PBS. After the $1^{st}$ transmission by the PBS 134PBS the optical energy passes twice through a quarter wavelength retarder 134P1 and is reflected by a mirror 134M1 back towards the PBS 134PBS. The mirror 134M1 is mounted on a translating element 134T1 that moves with linear velocity v during acquisition. The retarder 134P1 is aligned to rotate optical energy polarization by 90 degrees after double pass so that the PBS 134PBS reflects the energy towards a fixed mirror 134M2. This reflected energy also passed twice through a quarter wavelength retarder 134P2. The retarder 134P2 is aligned to rotate the optical energy polarization by 45 degrees after double pass. As a result the optical energy is split equally in two portion with one portion directed towards the moving mirror 134M1 again and the other portion directed towards a third fixed mirror 134M3 via a quarter wavelength retarder 134P3 oriented to rotate linear polarization by 90 degrees. After final reflections from the mirrors and final double passes via the retarders the optical energy potions at both polarizations are recombined by the PBS 134PBS and directed back towards the VDL 134 and then to the coupler 131. Thus the arrangement 134A splits linear polarization into two orthogonal polarizations, one polarization being reflected twice than the other off the moving mirror 134M1. As a result the polarization reflected twice has twice higher frequency of its phase modulation enabling the demodulation of the interferometric signals at the two linear polarizations.

The polarization fading can be also removed without using the polarization diversity detection by incorporating a non-reciprocal optical element or Faraday rotator 65 that rotates liner polarization by 45 deg in the distal end of the probe 50. Such Faraday rotator can be made for example from ~100 um to 500 um thick pieces of MGL Garnet material and commercially supplied by Integrated Photonics of New Jersey. In one exemplary embodiment of arrangements in the distal end 51 of the probe 50 with the fiber 57B shown in FIG. 12C, the Faraday Rotator 65 is disposed between the focusing GRIN lens 58A and the directing prism 59B and keeps polarization of retuned light substantially orthogonal to input polarization thus effectively canceling polarization perturbations in the probe 50.

Figure 13A:
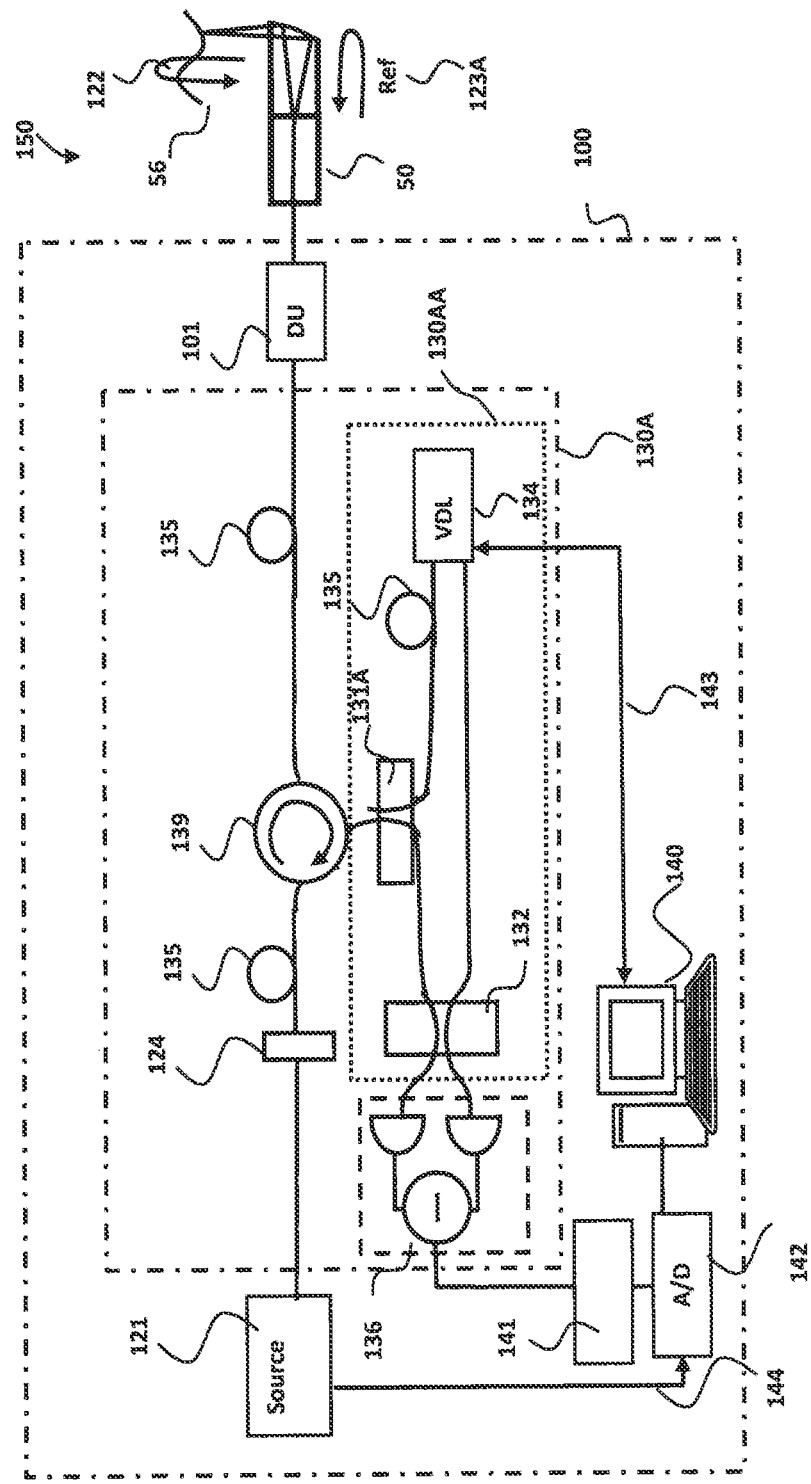
FIGS. 13A, 13B, 13C, 13D, 13E, 13F depict alternative embodiments for use with a system of the invention that employs a light-based imaging apparatus.
Figure 13B:
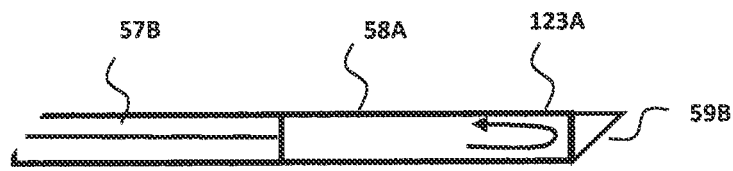

Another approach shown in FIG. 13A to improve stability of endoscopic imaging with the imaging apparatus 150 is to use a common-path interferometer 130A where the reference and the probe portions of the source light travel substantially common path in the probe 50. The substantially common path arrangement can be realized by delivering the light from the source 121 to the probe 50 via the optional polarization controller 135 and the optional polarization modulator 124 and a circulator 139 and the Drive Unit 101 and then splitting the source light at the distal end of the probe 50. When such splitting generates sufficient amount of back-reflection of the order of –10 dB to –40 dB, the back-reflection portion of light can be used as a reference portion 123A since it does not interact with the tissue 56. The probe portion 122 of light is back-scattered by the tissue to the probe and then returned to the interferometer 130A. The returned light that contains both the probe portion 122 and the reference portion 123A traveling substantially common path in the probe 50 is re-directed by the optical circulator 139 to a secondary interferometer 130AA. The returned light is further split in the secondary interferometer 130AA into two portions by an optical beamsplitter or coupler 131A. One of the split portions is delayed by the VDL 134 and then recombined with the other portion in the coupler 132 to produce interferogram. The polarization controller 135 disposed in the secondary interferometer 130AA is used to maximize the interferometric fringes visibility. The interferogram can be detected and processes in the same way as in arrangement with the separate path interferometer 130 described above for all three types of OCT. The back-reflection reference portion 123A can be obtained from any disruption or interface in the arrangements of the optical elements in the distal end of the probe 50. One example is shown in FIG. 13B where an interface between the GRIN lens 58A and the prism 59B provides required back reflection. By determining tilt, position and/or refractive index difference between the GRIN lens 58A and the prism 59B that results in required amount of back-reflection the probe 50 can be fabricated to accordingly. Many other interfaces can be chosen for generating back-reflected reference light; however for practical implementation it is important to suppress other back-reflections to acceptable levels significantly less than –40 dB controlling the tilt angle of all the interfaces. Because probe and reference portions of light travel substantially the same path they experience same phase and polarization perturbations. Thus sensitivity of imaging to the probe bending, rotation, and temperature changes is greatly reduced. All the components of the interferometer 130A can be made from off-the shelf fiber optic components using standard single mode fiber.

Figure 13C:
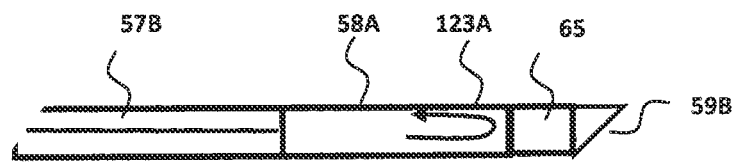
Figure 13D:
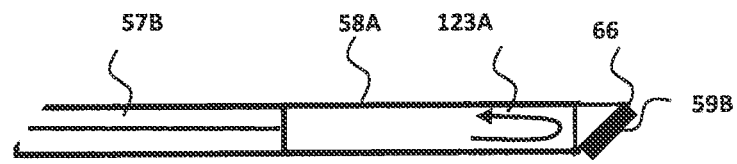
Figure 13E:
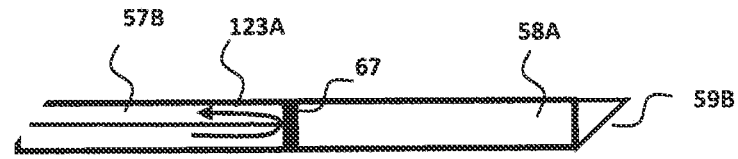
Figure 13F:
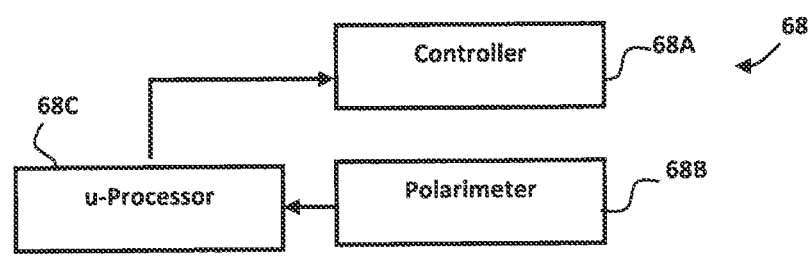

Because the probe and the reference portions of light are present in both arms of the secondary interferometer 130AA their interference may produce more artefacts and more beat noise compared to the separate path interferometer 130. Therefore it might be advantageous to have arrangements that facilitate separation of the probe and the reference portions into different paths of secondary interferometer while making sure that the probe and the reference portions experience substantially similar perturbations in the probe 50. In some embodiments, this goal can be achieved by using PM fibers in the common path interferometer 130A, the Drive Unit 101 and the probe 50. Launching the source light in one linear polarization mode of the PM fibers with the help of the polarization controller 135 with maintain polarization in the probe 50 distal end as well. The 45 degree Faraday Rotator 65 disposed in the distal end of the probe 50 between the interface producing the reference portion back-reflection 123A and the tissue, for example, between the GRIN lens 58A and the prism 59B as shown in FIG. 13C rotates linear polarization of probe portion by 90 degree relative to the reference portion making the probe and the reference portions separated by polarization. Then a polarizing beamsplitter can be used as the coupler 131A in the secondary interferometer 130AA of FIG. 13A to direct the probe and the reference portions towards different paths in the secondary interferometer 130AA. To achieve interference in the coupler 132B the polarization controller 125 can rotate polarization of one of the portions of light. The advantage of using the Faraday rotator 65 is that no alignment with the PM fiber axis is needed during fabrication of the probe 50. Nevertheless use of the faraday rotator at the distal end may increase dimensions of the probe. Alternative arrangement is shown in FIG. 13D where relative polarization rotation of the probe and the reference portions of light is achieved by means of a quarter wavelength retarder 66 oriented at 45 degree to the linear modes of the PM fiber. For example such retarder can be a reflective quarter wavelength retarder made from inorganic film fabricated by JDSU as disclosed by U.S. Pat. No. 7,170,574. This inorganic film can be conveniently deposited on hypotenuse of the prism 59B. While having advantage of smaller dimensions this embodiment requires alignment of the prism 59B and the PM fiber axis. Another arrangement is shown in FIG. 13E where a reflective polarizer 67 is placed between the PM fiber 57B and the GRIN lens 58A so that the polarization axis of the polarizer is aligned with the polarization axis of the PM fiber. In this case, when the polarization controller 135 in the image console 100 of FIG. 13A is aligned to send the source light in both polarizations of the PM fiber, the reference portion 123A of light reflected from the polarizer 67 will have one polarization while the probe portion of light transmitted through the polarizer and then back-scattered by tissue will have the orthogonal polarization. Metal nanowire grid polarizer deposited on the fiber facet can be used as the polarizer 67. Advantage of this arrangement is ability to adjust probe to reference power ration by adjusting polarization state with the polarization controller 135.

The use of single mode fibers in the probe of the embodiment using the common path interferometer 130A with facilitated separation of the probe and path portions in the secondary interferometer 130AA may be more advantageous because of the smaller diameters and smaller cost of SM fibers. For this, incorporation of high speed polarization stabilization arrangement 68 shown in FIG. 13F consisting of a high speed polarization controller 68A, a micro-processor 68C, and a polarimeter 68B into the common path interferometer 130A can be used. The high-speed polarization controller 68A and the polarimeter 68B can be for example commercially available dynamic polarization controller PolaRite II and in-line polarimeter PolaDetect, respectively, both from General Photonics of California. The micro-processor 68C can be the dedicated processor integrated into the General Photonics PolaDetect polarimeter, or the processor of the CPU 140. The polarimeter 68B should measure SOP of the returned light in location close to the PBS 131A of the common path interferometer 130A. Because the reference portion 123A of light can be made on in the range of −10 to −20 dB which is significantly larger than the probe portion of −30 to −100 dB, SOP measured by the polarimeter 68B is dominated by SOP of the reference portion of light 123A. The micro-processor 68C can control SOP of the reference portion at the distal end of the probe by measuring SOP with the polarimeter 68B and setting polarization controller 68A to make the distal end SOP locked at predetermined target state regardless of perturbations in the probe. The target SOP at the distal end can be selected to facilitate separation of the probe and the reference in the secondary interferometer 130AA. The relationship between SOP measured by the polarimeter and the target SOP at the distal end can be quite simple for many arrangements in the distal end of the probe. For example, if the probe distal end has the Faraday rotator 65, similar to arrangement shown in FIG. 13C but with single mode fibers instead of PM fiber, the probe and reference portions will have orthogonal SOP as long as the reference portion SOP is linear at the distal end. Thus if the circulator 139 has negligible effect on SOP and if the high-speed polarization controller is placed between the circulator and the probe in a double-pass configuration, maintaining SOP measured by the polarimeter to be substantially identical to input liner SOP ensures that probe and reference SOPs are orthogonal and linear in the SOP measurement location and therefore can be separated by the PBS 131A.

Embodiments with Means for Encoding of Location Information.

In related implementations, the imaging data (acquired by the probe system of the invention in response to projection of the interrogating energy from the module 120 of FIG. 1 by the means for coupling of the probe) is generated based on backscattering of the interrogating energy that contains encoded information representing tissue locations. FIGS. 14-16 illustrate examples of embodiments of an imaging probe of the present invention with encoding means that enable miniaturization of the probes, extending depth of imaging, and/or advantageously combining side imaging and forward imaging are now described.

Figure 14A:
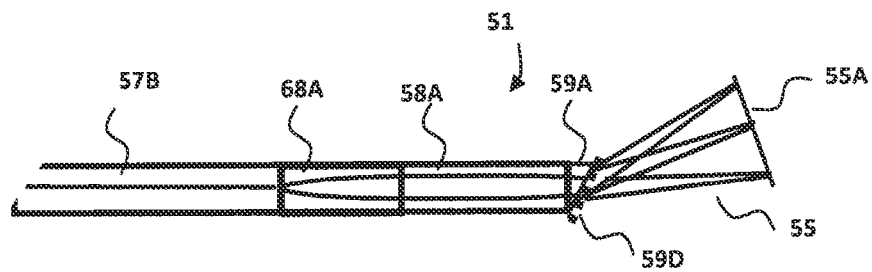
FIGS. 14A and 14B illustrate an embodiment of the invention employed in imaging with the use of spectral encoding.
Figure 14B:
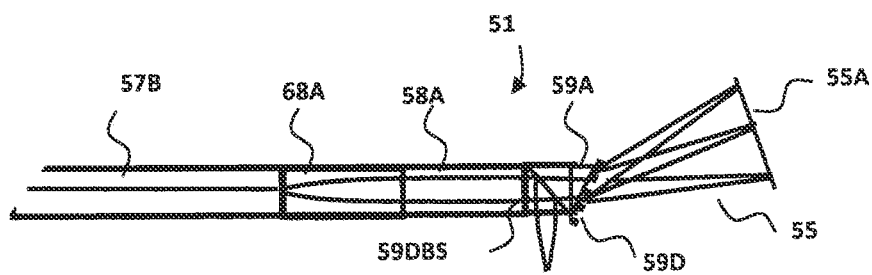

Spectral Encoding. FIG. 14A illustrates an embodiment containing means for spectral encoding of the locations of the interrogated tissue. Here, a diffraction grating 59D is juxtaposed with on the energy directing element 59A (structured as an angled prism) that is attached to the GRIN lens 58A. The GRIN lens 58A is in turn adjacent to the glass cylinder 68A and, through it, to the means for delivery of optical energy from the module 120 of FIG. 1. The diffraction grating 59D forms, in transmission and on a chosen surface such as for example an internal surface of the luminal tree, an imaging line 55A that projects different spectral content of the interrogating energy on different tissue locations along the line 55A. Accordingly, light backscattered by tissue at different locations corresponding to line 55A is spectrally encoded, and the imaging data representing spatial information characterizing the tissue is acquired by spectral processing of the backscattered light. An embodiment shown in FIG. 14B shows an improvement of the embodiment of FIG. 14A in that the energy directing element is configured as a beamsplitter 59DBS (dichroic and/or polarizing), thereby allowing side-looking imaging and volumetric forward-looking imaging. This embodiment can be used, for example, as an alternative embodiment of the shaft of the probe 50C or the probe 50D of FIG. 5. The beamsplitter 59DBS sends a portion of optical energy sideways to form side imaging scanning pattern and transmits the portion of optical energy toward the diffractive element 59D to form forward looking pattern. The separation between side imaging and forward imaging can be based on using different polarization state or on using different spectral bands. The side imaging is formed by scanning focused optical energy in the radial pattern, while forward imaging is formed by rotating the imaging line 55A thus producing volumetric images once the returned optical energy is decoded using methods described, for example, in US 2007/0188855. This volumetric forward image combined with side imaging and with steering capabilities can then be used for navigation as described above.

Accordingly, an embodiment of the navigational system includes the means structured to outcouple light towards the ambient medium such as to enable the data-processing unit to differentiate between first and second points of the ambient medium based on differences in spectra of light returned from the first and second points to the first means through the second means.

Figure 15A:
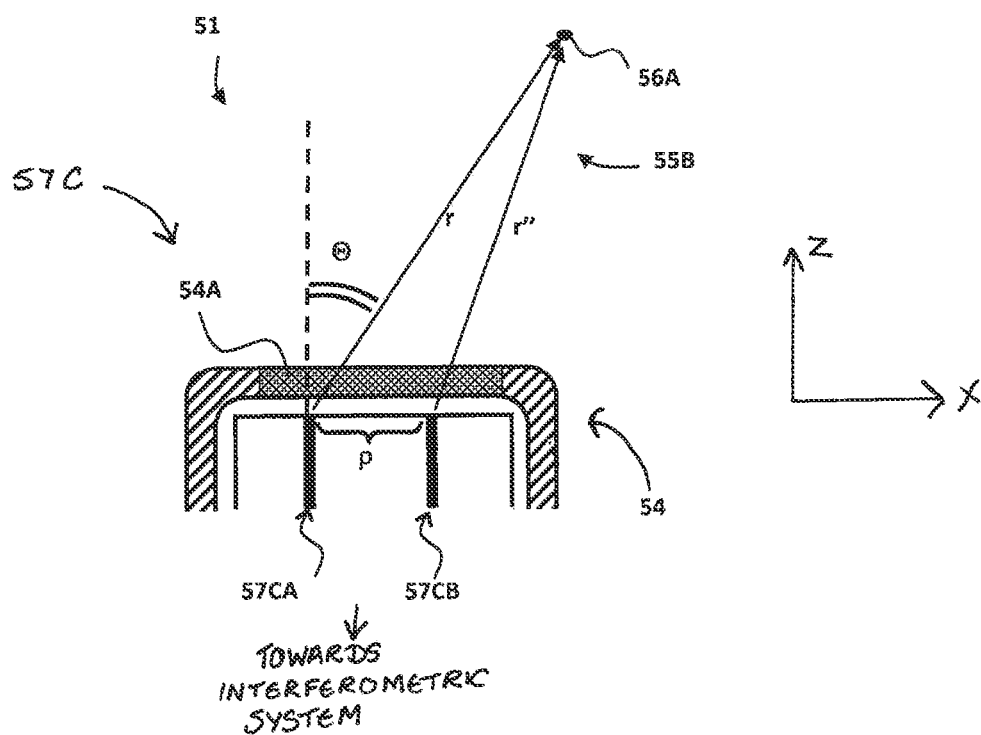
FIGS. 15A, 15B, 15C illustrate an embodiment of the invention employed in imaging with the use of frequency encoding.

Frequency Encoding. In a related embodiment, the optical response received from irradiated parts of the tissue is encoded with different frequencies of the interferometric signal. As illustrated in FIG. 15A, the distal end 51 of the probe 50 of the embodiment contains a dual core fiber 57C, in which the first and second cores 57CA, 57CB are separated by a distance ρ. The dual core fiber 57C is enclosed by the sheath 54 that is at least partially transparent in a cap region 54A. For the purposes of illustration, the sheath region 54A has a cylindrical surface focusing light emitted from the cores 57CA and 57CB at least in the plane of the drawing of FIG. 15A (xz-plane) while being divergent in this plane. In this manner an imaging region 55B is formed in the xz-plane. Light scatter from a location 56A (a tissue point) can be specified by a distance r separating the point 56A from the first core 57CA and an angle between the axis of the first core 57CA and the vector signifying the direction from the first core 57CA to the scattering point 56A. The distance between the scattering point 56A and the second core r″ can be expressed via the path difference parameter r−r″=Δ(r,Θ) ∼ρ·sin Θ∼ρ·Θ, the dependence of which on r is not significant, at least for small values of angle θ.

If the optical field in each of the cores 57ACA, 57CB is denoted as $E_0$, the optical field $E_1$ that results from emission of the field $E_0$ from the first core 57CA and scatter at the scatter point 56A and coupling back to the first core 57CA is expressed as $E_1 \sim E_0 e^{2ikr}$, where $$k = \frac{2\pi}{\lambda}$$

is the wavenumber and $\lambda$ is the wavelength of the optical radiation. Similarly, field $E_2$ that has been coupled into the first core 57CA as a result of emission of the field $E_0$ from the second core 57CB, scatter at the scatter point 56A, and coupling into the first core 57CA is expressed as $E_2 \sim E_0 e^{ikr} e^{ikr''}$. The total field $E_s$, acquired by the first core 57CA as a result of scattering of optical energy delivered from the module 120 of FIG. 1 by the optical fiber 57C and scattered by a tissue point 56A is, therefore, $$E_s = E_1 + E_2 \sim E_0 \cos\left(\frac{k}{2}\Delta(r,\Theta)\right) e^{ikr} e^{i\frac{k}{2}\Delta(r,\Theta)}.$$

Figure 15B:
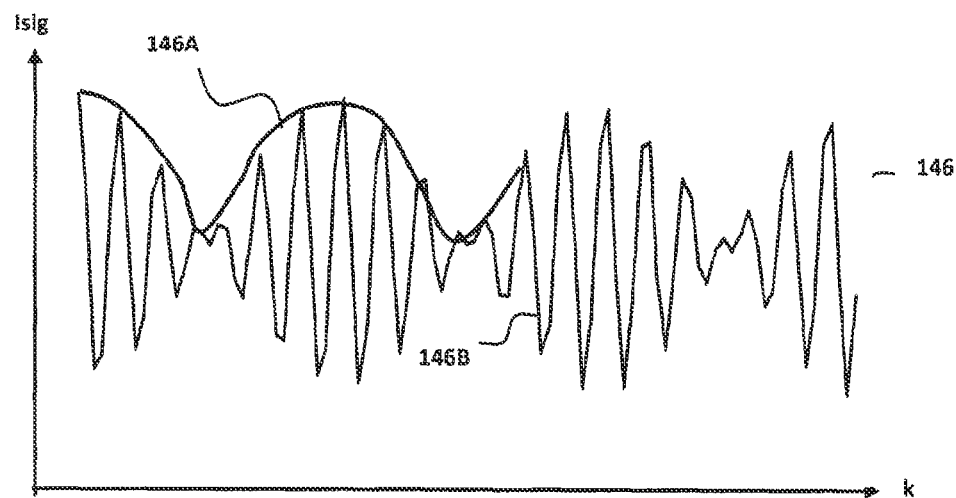

The interferogram formed by the interferometric set-up, appended to the proximal end of the probe 50 containing the embodiment 57C (for example, an interferometric system 130 of FIG. 12A or 130A of FIG. 13A), from interference of the scattered optical field $E_s$ collected by the fiber with the reference field $E_{ref} \sim E_0 e^{ikr_0}$ can be expressed as $$I_{sig} \sim E_0^2 \cos\left(\frac{k}{2}\Delta(r,\Theta)\right) \cos\left(k(r-r_0) + \frac{k}{2}\Delta(r,\Theta)\right),$$

where $r_0$ represents an optical path in the reference portion of the interferometer 130 or 130A. The intensity fringes corresponding to such interferogram are shown in FIG. 15B. As illustrated in FIG. 15B, the interferogram 146 includes the first oscillating cosine function 146B with its amplitude and phase modulated by the second oscillating cosine function 146A. The modulating cosine function 146A depends only on $\Delta(r,\Theta) \sim \rho \cdot \sin \Theta \sim \rho \cdot \Theta$ and thus encodes the polar angle of the location of the scattering point 56A, while the cosine function 146B also depends on the distance r and thus encodes the second coordinate of the scattering point 56A. By setting the appropriate value of the optical path $r_0$ in the reference portion of the interferometer 130 or 130A, one is enabled to slow down the oscillation of the modulation cosine function 146A to the oscillation rate that is lower than that of the carrier cosine function 146B.

The following example helps to understand the above-made assertion. Consider the dual core fiber 57C where each core has numerical aperture NA~0.3 and the separation between the cores is =240 microns. If the central wavelength of the optical radiation is $\lambda$=0.8 microns and the wavelength range is such that $\Delta\lambda/\lambda$=0.3, the modulation cosine function 146A will make $$\frac{\Delta\lambda}{\lambda} \cdot \frac{\rho}{\lambda} \cdot \Theta = 0.3 \cdot 300 \cdot 0.3 = 21$$

cycles when the scatter polar angle $\Theta$ changes from −0.3 radian to +0.3 radian. In contrast, setting $r_0$ such that $$r - r_0 > 10 \cdot 21 \cdot \frac{\lambda}{\Delta\lambda} \cdot \lambda = 0.5 \text{ mm}$$

ensures that the oscillations of the carrier cosine function 146B are at least 10 times faster. A person of skill in the art will readily appreciate how to achieve even larger oscillation-frequency-difference between the modulation cosine function 146A and the carrier cosine function 146B by using appropriate modulation techniques. For example a frequency shift to the reference field can be added by employing a commercial fiber optic frequency shifter in the reference portion of the interferometer 130 or 130A in the case of the FD-OCT implementation of the frequency encoding. In the case of SD-OCT implementation, a tilt angle to the reference field with respect to the signal field in the spectrometer potion of the interferometers 130 or 130A can be added.

Describing further modifications to the interferometric systems to practice this aspect of invention, the issue of stability of the interferogram 146 stability (e.g., polarization fading) needs to be addressed. Since the optical energy travels along the substantially equal paths in the cores of the dual core fiber 57C, the effects of polarization fading on the interference between optical fields of the first and second cores 57CA and 57CB may not be significant. The polarization fading effects can be further reduced by using polarization preserving cores in the fiber 57C, and/or by adding a polarization stabilizer, and/or by adding means to modulate polarization in one of the cores of the dual core fiber 57C. Appropriate modification of the interferometric system 130 or 130A to accommodate the above-mentioned additions, together with modifications of the drive unit 101 to operably append the dual core fiber to the image console 100 of the imaging apparatus may be required. To this end, for example, a 50:50 1-to-2 fiber-optic splitter can be disposed in the probe portion of the interferometer 130 of FIG. 12A between the polarization controller 135 and the drive unit 101. The outputs of the fiber-optic splitter can then be coupled, respectively, to the cores of the dual core fiber 57C independently at the proximal end of the probe 50. A polarization modulator similar to the polarization modulator 124 of FIG. 12A can be disposed in one of the outputs of the 50:50 fiber splitter and multi channel FORJ commercially available from Princetel of New Jersey can be used in the drive unit 101.

The algorithms for decoding the spatial information from the interferogram 146 can optionally employ a digital 2D matched filter. In further reference to FIG. 12A, one specific implementation the interferogram 146 is digitized by the A/D converter 142 and then convoluted with a matched filter function MF of the form $$MF(k, r', \Theta') \sim \cos\left(\frac{k}{2}\Delta(r',\Theta')\right) \cos\left(k'(r-r_0) + \frac{k}{2}\Delta(r',\Theta')\right)$$

to obtain the image irradiance expressed as $I_{image}(r',\Theta')=\int I_{sig}(k) \cdot MF(k,r',\Theta')dk$.

Other algorithms of signal-processing of the interferogram 146 in order to decode spatial information about the irradiated tissue can be employed to take advantage of the fact that both distance and angular dependencies are encoded by different range of frequencies in the interferogram 146. It is instructive to estimate spatial resolution of the frequency encoding imaging to help understand the frequency encoding aspect of the present invention further. The full width at the half maximum (FWHM) of the output of the matched filter processing for a point scatter can be used as a measure of the spatial resolution. The FWHM along the direction of vector r is substantially identical to the standard depth resolution of OCT methods and, therefore, is on the order of few micrometers to tens of micrometers (depending on the spectral range of the optical source). The angular FWHM resolution can be estimated to be as small as $$\delta\Theta \approx \frac{\lambda}{\Delta\lambda} \cdot \frac{\lambda}{\rho} \cdot \frac{1}{12} \approx 1 \text{ mrad}$$

for the separation between the cores $\rho=240$ microns, the central wavelength of the optical radiation $\lambda=0.8$ micron and the wavelength range corresponding to the ratio of $\Delta\lambda/\lambda=0.3$. As an optical fiber with a core defining the mean diameters of propagating fiber modes (mode field diameter or MFD) as small as few micrometers can be fabricated, the resulting full angle of divergence of the optical radiation upon exiting such a fiber is about several tenths of radians. Therefore, useful angular resolution of more than one hundred of scatter spots can be achieved with the frequency encoding methods of the high resolution imaging of the lumen wall tissue.

Figure 15C:
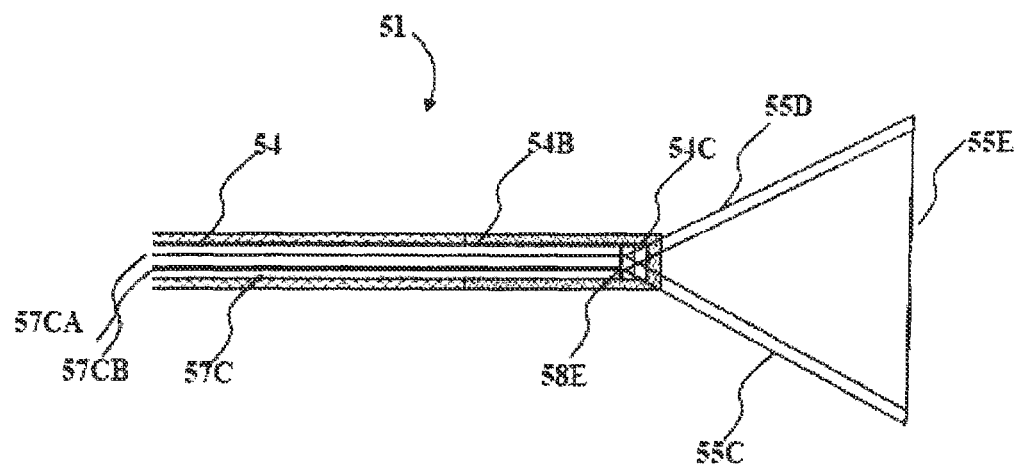

Turning now attention to detailed description of an example of the embodiment of the probe for frequency encoding imaging, FIG. 15C shows arrangements at the distal end 51 of the probe 50. The dual core fiber 57C desirably has cladding diameter of approximately 250 um or less, with the separation between the cores 57CA and 57CB of approximately 100 microns. The cores 57CA and 57CB have MFD less than 10 um and desirably have MFD 1.5 microns and support only single mode at wavelengths around 1 micron. The dual core fiber 57C with such specifications can be made, for example, by fabricating a photonic crystal fiber fabrication (see Alexis Mendez et al, "Specialty optical fibers handbook", Academic Press: 2007). For example, the highly nonlinear photonic crystal fiber model NL-2.4-800 supplied by Thorlabs of New Jersey has MFD of 1.5 um at 0.8 um wavelength and cladding diameter of 120 um. The design of the NL-2.4-800 fiber can be readily modified to include a second core with the same MFD, while keeping the cladding diameter under 250 um. Moreover, the outer sheath 54 can be deposited during the dual core fiber 57C fabrication using standard fiber optic coating process. Biocompatible coating material such as ETFE can be used and the thickness of the ETFE coating can be controlled to fabricate the dual core fiber 57C enclosed in the sheath 54 with diameters of 0.5 mm or less. For example, fiber coating diameters of 0.4 mm are common in fiber optics. The coating or the sheath 54 can be stripped at the end of the fiber using commercial fiber optic stripper and the fiber 57C can be cleaved by using any standard fiber optic techniques. Then an astigmatic focusing element 58E can be attached to the fiber 57C or fabricated directly on the fiber 57C facet in such way so that the optical radiation forms divergent patterns 55C and 55D from the each core in the drawing plane of FIG. 15B. At the same time the astigmatic focusing element 58E focuses the optical radiation to the plane of FIG. 15B to the linear spot size of approximately 30 um to form an imaging line 55E approximately 1 mm or less away from the probe end. Any other spot sizes can be used in this method as long as the divergence of the imaging line 55E in the plane orthogonal to the drawing of FIG. 15B does not affect the useful depth of imaging. The useful depth of imaging depends on diameter of lumens and in many practical situation should be approximately 1 mm or larger. The stripped portion of fiber with the astigmatic focusing element 58E is then enclosed with a transparent portion of the sheath 54B. The transparent portion of the sheath 54B can be fabricated from PTFE, FEP, or nylon micro-tubing and the tip of the transparent portion of the sheath 54B can be fabricated by standard tip processes such as RF tipping in a die. Then the transparent portion 54B is placed over the striped portion of the fiber 57C and bonded to the sheath 54 with heat fusion or adhesive, making sure that there is an air gap 54C between the astigmatic focusing element 58E and the transparent portion 54B. The fabrication of the astigmatic focusing element 58E can be done, for example, with the use of jet printing of optical materials. For example, the thermoplastic material disclosed in U.S. Pat. No. 5,707,684 with the refractive index of 1.7 can be used and a cylindrical surface of the jet printed focused element 58E can be fabricated as disclosed in U.S. Pat. No. 5,707,684. An intermediate glass cylinder can be fused or bonded to the dual core fiber 57C and polished to required length to serve as a substrate for the jet printing fabrication of the astigmatic focusing element 58E. Alternatively a GRIN lens with a pitch p=0.5 and diameter substantially equal to the diameter of the dual core fiber 57C cladding can be spliced to the dual core fiber 57C to serve as the substrate for the jet printing fabrication. Such GRIN lens acts as a relay lens with magnification m=−1 and can be fabricated as described in by William A. Reed et al, Optics Letters, Vol. 27, No 20, 2002, pp 1794-1796 with gradient index parameter g~2 min$^{-1}$ and thus having length less than 1 mm. The required specification for the astigmatic focusing element 58E is determined as follows. A spot diameter of 22.5 um at 0.8 um results in imaging depth in the air of approximately 1 mm. Therefore, the astigmatic focusing element 58E should magnify the MFD=1.5 um of the dual core fiber 58E in one plane by m=15. If the required distance from the astigmatic focusing element 58E to the imaging line is s'=1 mm, the required effective focal length of the astigmatic focusing element 58E is EFL=s'/(1+m)=62 um. The curvature radius $R_1$ of the cylindrical surface in the plane orthogonal to the drawing plane of FIG. 15B of the astigmatic focusing element with refractive index n=1.7 is related to the required EFL as follows $R_1=(n-1)\cdot EFL \approx 44$ μm while the curvature in the plane of drawing should be substantially zero. The thickness s of the astigmatic focusing element 58E can be determined from the required magnifications as s=s'/m=67 um. A person of skill in the field of optics will readily determine the required curvatures of the astigmatic focusing element 58E to achieve a desired location of the image line 55E and the desired spot size in that location using standard formulae of Gaussian optics and transformation of Gaussian beam by a spherical surface. It would be also clear from above descriptions how to modify the arrangement shown in FIG. 15C for different diameters of the probe and different operating wavelengths.

The embodiment of FIG. 15C can be easily converted to one having a side imaging capability by optically cooperating an approximately 90 degree turning mirror or prism with the distal end of the optical fiber 57C. The advantage of such modified arrangement (not shown) is its ability to enable cross-sectional imaging without a need for mechanical rotation of any component. Alternatively, if such modified arrangement is disposed inside another sheath that is rotating, a volumetric image of the tissue can be obtained without need for a pull-back. Similarly, the arrangement of FIG. 15C can be used as the rotating shaft of the probe 50D of FIG. 5 that has volumetric forward imaging capability and the working channel. Although the method of the frequency encoding is described for the case of the dual core fiber 57C, it is clear from the above description how to extend the described method to more than two cores and to the use of separate fibers in practicing of this aspect of invention.

Accordingly, an embodiment of the navigational system of the invention includes means structured to outcouple light towards the ambient medium such as to enable the data-processing unit to interferometrically differentiate polar coordinates of first and second points of the ambient medium based on frequency-shifted light delivered to the second means from the imaging console.

Doppler Encoding. While the frequency encoding solves many deficiencies of the spectral encoding, it still presents a shortcoming of added structural complexity both to the distal end of the probe and to the proximal end of the imaging apparatus. Another implementation of high-resolution imaging with encoding of spatial information free of these limitations is imaging employing phase- or Doppler encoding. In the Doppler encoding, relative motion of the tissue and the beam of optical radiation emitted by the probe results in different rate of phase changes (or different Doppler shifts) of light returned by different regions of the tissue. By processing and analyzing the phase of the returned optical energy it is possible to decode spatial information of the tissue response. The decoding of spatial information encoded with such Doppler shifts is already used in the field of synthetic aperture radars (SAR) or sonars (SAS). Methods of synthetic aperture imaging that use known forward model of optical fields followed by solving inverse problem the reconstruct tissue susceptibility have been also proposed for use in interferometric synthetic aperture microscopy (ISAM), but they cannot be easily applied for luminal structures imaging because of phase instabilities, non-uniform scanning speeds, loss of signal due to defocusing of optical energy, and difficulties in arranging imaging with ISAM in the forward direction inside body lumens, lack of knowledge of the exact model of optical field and large computational burden associated with solving inverse imaging problems.

Referring now to FIGS. 16-17, several embodiment of an imaging probe equipped with Doppler encoding means and associated signal processing algorithms that overcome at least some of the above mentioned problems are now described. The Doppler encoding imaging of the present invention can be more readily understood if it is contrasted with ISAM of U.S. Pat. No. 7,602,501 in luminal anatomical structures. According U.S. Pat. No. 7,602,501, ISAM is performed by scanning a Gaussian optical beam (rotationally for endoscopic application) and processing full frame data (i.e. all A-lines from full frame) with ISAM algorithms, which include direct and inverse Fourier transformations across A-lines (along scan directions) and data interpolations in w-k space. As a result, for the ISAM algorithms to function phase stability of data among A-lines needs to be maintained, typically better than 218 over the synthesized aperture. The phase stability is achieved in U.S. Pat. No. 7,602,501 for the case of OCM by using a reference reflector, namely an air-glass interface from a microscope slide in contact with imaged tissue, the imaged tissue being immobilized with respect to the reference reflector. The disclosure of U.S. Pat. No. 7,602,501 contains a speculation that a similar arrangement can be devised for an endoscopic version of ISAM, and, specifically, proposes to use reflection from a surface of the catheter sheath as the reference reflection. However, it is often required to image lumens with a wide range of inner diameters with a single imaging probe. One example is a need to image a main bronchus of approximately 10 mm inner diameter with a probe than can reach 2 mm ID bronchi (such as the probe 50B of FIG. 5, for example). Immobilization of the tissue being imaged with respect to the probe sheath is impractical in many clinical applications, for example during navigation in body lumens. During imaging tissue can move or dislocate with respect to the sheath, sometimes with velocities exceeding few mm/sec. The dislocation of this sort easily leads to phase errors exceeding one wavelength over the synthesized aperture, even when phase errors relative to the reference reflector (such as the probe sheath) are completely corrected. Also, because imaging probes in luminal structures can be required to bend significantly, one of the main sources of phase instabilities affecting the ISAM algorithms is non-uniformity of scanning. This source of error cannot be corrected by the use of a reference reflector as described in U.S. Pat. No. 7,602,501. Finally, the ISAM algorithms rely on solving complete inverse scattering problem and, as such, require significant computational resources. In contradistinction with the ISAM approach, the Doppler encoded imaging enabled according to embodiments of the present invention, light beam(s) at the output of the optical probe is shaped so that differential Doppler shifts encode the spatial location in the tissue with greatly reduced sensitivity phase instabilities. These differential Doppler shifts also allow simplified image reconstruction algorithms.

Figure 16A:
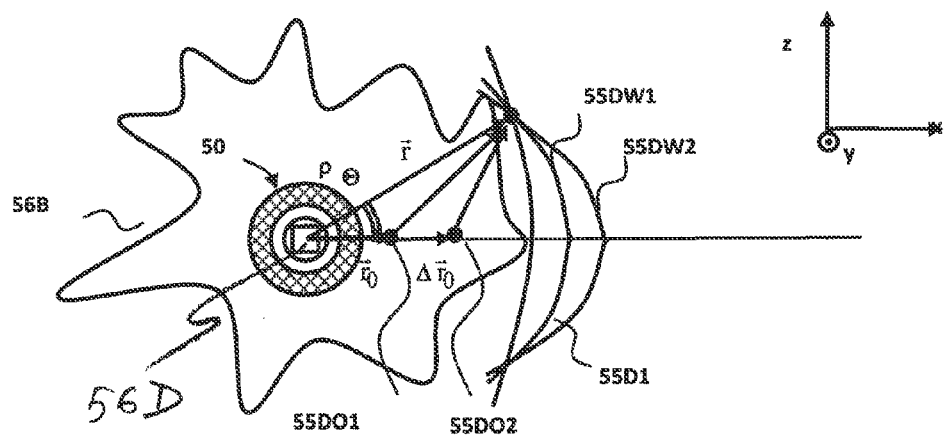
FIGS. 16A, 16B, 16C illustrate an embodiment of the invention employed in imaging with the use of Doppler encoding.

The principle of the differential Doppler encoding can be better understood by considering the interferometric signal from a scattering tissue point 56D of a lumen wall 56B, illustrated cross-sectionally in FIG. 16A. The spatially-moving scattering point 56D is illuminated by optical beam 55D1 emitted from the probe 50, the optical beam 55D1 with a Gaussian beam profiled and focused at the point characterized by vector $\vec{r}_0$ (so that the beam wavefronts 55DW1 can be modeled as spheres with radius $r_1$ outside of the confocal region). In the reference frame xyz that moves together with the shaft of the probe 50, the scattering point 56D with polar coordinates $\rho,\Theta$ has generally a circular trajectory $\rho(\tau)=\rho$, $\Theta(\tau)=\Theta'+\tau$. Here $\tau=\omega t$ represents real time variable that can be parameterized by A-line numbers in FD-OCT or SD-OCT and $\omega$ is the angular velocity of the shaft rotation. Outside of the confocal region, the interferometric signal from the optical beam 55D1 can be modeled as $V_{sig,1} \sim e^{2ik|\vec{r}-\vec{r}_0|} = e^{2ik\sqrt{\rho^2+r_0^2-2\rho r_0 \cos\Theta}}$. Defining $r_1^2(\rho,\Theta')=\rho^2+r_0^2-2\rho r_0 \cos\Theta'$, the interferometric signal model can be further simplified to yield $$V_{sig,1} \approx e^{2ik\sqrt{r_1^2+2\rho r_0 \sin\Theta' \tau}} = e^{2ikr_1\left(1-\frac{\rho r_0 \sin\Theta'}{r_1^2}\tau\right)} = e^{2ikr_1} e^{-\frac{2k\rho r_0 \sin\Theta'}{r_1}\tau}.$$

The polar angle coordinate is encoded by different phase shifts, or Doppler shifts, in the $V_{sig,1}$ function because the scattering point 56D crosses the wavefronts 55DW1 at different angles as it moves along its trajectory. If, during the imaging process, the scattering point 56D is also illuminated by a second Gaussian optical beam 55D2 (not shown; focused to a point 55D02 located at distance $r_0$ from the first focus 55D01 with its wavefront 55DW2 centered at the second focal point 55D02), the second interferometric signal from the optical beam 55D2 can be represented as $$V_{sig,2} \approx e^{2ikr_2} e^{\frac{2k\rho(r_0+\Delta r_0)\sin\Theta'}{r_2}\tau}$$

where $r_2^2(\rho,\Theta')=r_1^2+2r_0\Delta r_0+\Delta r_0^2-2\rho\Delta r_0 \cos \Theta'$. It is clear that the phase difference between $V_{sig,2}$ and $V_{sig,1}$ also encodes polar angles with different Doppler shifts, provided that $\Delta r_0$ is sufficiently larger than the confocal parameter of each beam. At the same time, the common phase error is cancelled, thereby reducing unwanted sensitivity of the imaging system to the motion of body and/or catheter/probe.

More specifically, a signal processing algorithm to decode spatial information can be implemented using a digital 2D matched filter. Here, the first interferometric signal is divided by the complex conjugate of the second interferometric signal, and the result is then convoluted with a matched-filter function $MF_S$ of the form $$MF(k, \tau, \rho, \Theta') \sim V_{sig,2} \approx e^{2ik(r_1-r_2)} e^{\left[\frac{r_0}{r_1}-\frac{r_0+\Delta r_0}{r_2}\right]2k\rho\sin\Theta'\tau}$$

to obtain the following image irradiance distribution:

$$I_{image}(\rho, \Theta') = \int\int \frac{V_{sig,1}(k,\tau)}{V_{sig,2}^*(k,\tau)} \cdot MF(k, r', \Theta')dkd\tau$$

From the above description, the modifications of other SAR algorithms such as, for example, range—Doppler, w-k, or back-projection to differential Doppler shifts will be readily understood by a person of skill in the art familiar with synthetic aperture imaging. Cancellation of the phase errors in these modified algorithms by using the differential Doppler shifts results in significant simplification and reduction of computational burden, because no auto-focusing will be required.

Figure 16B:
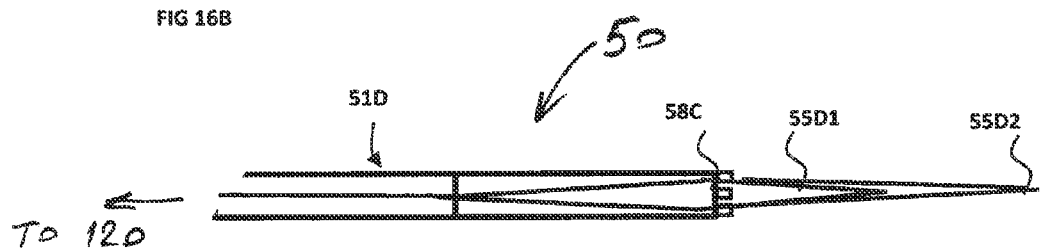
Figure 16C:
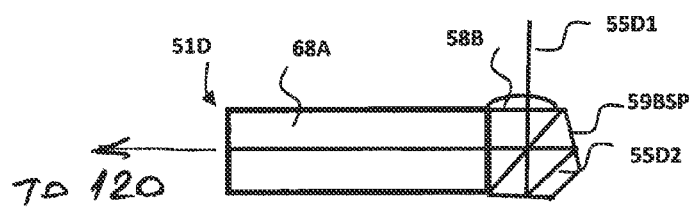

Referring now to the detailed description of multi-focal or dual-focus embodiments of the probes enabling differential Doppler encoding, FIG. 16B shows a distal end 51D of the probe with the diffractive focusing element 58C structured to introduce significant chromatic longitudinal aberration into light passing therethrough. Here, two different optical beams 55D 1 and 55D2 emanating from the distal end 51D of the optical probe have different optical wavelengths and, therefore, are focused at different locations. The arrangements at the proximal end for generating, detecting and processing different spectral bands are shown in FIG. 18 and explained in more detailed further below. Substantially any energy-directing element can be added to the arrangement of FIG. 16B to modify it to obtain side-looking imaging capability as discussed in this disclosure. Alternative embodiment of the dual focus distal end arrangement 51D for differential Doppler encoding imaging system is shown in FIG. 16C, where a beamsplitting directing element 59BSP is fused or bonded with adhesive to the glass cylinder 68A and the focusing element 58B is formed on the outside surface of the directing element 59BSP. One of the internal surfaces of the directing element 59BSP has a dichroic beamsplitting coating to redirect or split optical radiation in different spectral bands into two different divergent beams 55D1 and 55D2 that traverse different paths and, therefore, are focused at different locations. Alternatively, a polarizing beam splitting coating can be used and the two different beams 55D1 and 55D2 can be differentiated by using different polarization. In the embodiment with the polarizing beamsplitter, PM fiber should be used in the probe and the interferometer in the imaging console. It is clear from above description that many other dual focal arrangements can be used for differential Doppler encoding imaging of the present invention.

Figure 17A:
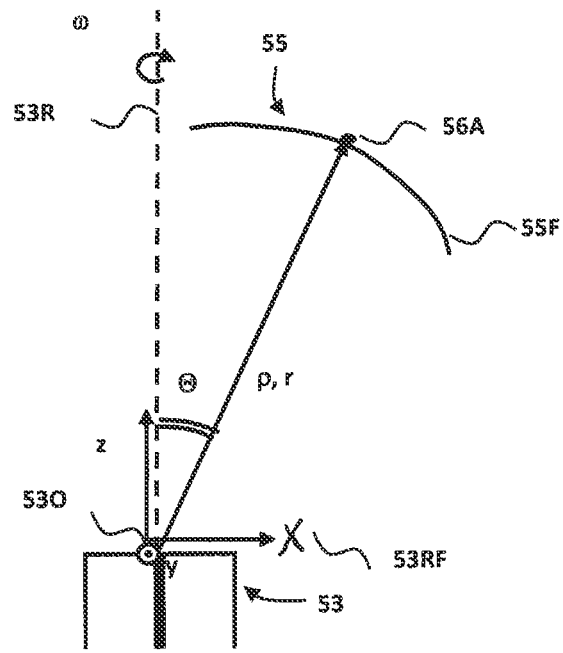
FIGS. 17A, 17B, 17BB, 17C, 17CA, 17CB, 17D illustrate an alternative embodiment employed in imaging with the use of Doppler encoding.

Spreading the optical energy in all directions outside the confocal region may result in loss of signal strength and degrading quality of the tissue image. Recreation of the two types of motion such as rotation and translation (which are substantially orthogonal to each other) for the Doppler encoded imaging may be complicated for forward-looking imaging embodiments of the imaging probe 50. Therefore, it might be advantageous to at least partially focus optical energy for direct imaging and use the Doppler encoding in the other, unfocused direction of optical energy. This can be achieved by asymmetrically shaping the optical beam out-coupled from the probe, as described in reference to FIG. 17A-17E. Specifically, FIG. 17A shows the optical energy 55 emitted from the probe shaft 53 that rotates with angular velocity ω. The optical energy 55 is substantially focused perpendicularly to the drawing plane of FIG. 17A (as shown, in a plane containing y-axis). For example, the optical energy 55 may have Gaussian intensity distribution $$I(y)\cdot = I_0 \cdot e^{\frac{-2y^2}{w_y^2}}$$

in the y direction indicated in FIG. 17A, where $w_y$ is substantially small. At the same time, the optical energy 55 is divergent in the x-z plane so that wavefronts 55F are astigmatic. For example the wavefronts 55F can be cylindrical surfaces centered on a line curvatures 53O perpendicular to a rotational axis 53R of the shaft 53. FIG. 17A also shows a coordinate system 53RF centered on the intersection of the rotational axis 53R aligned in the z direction and the line of curvatures 53O aligned in the y direction. The cylindrical surfaces of the wavefronts 55F have finite radii of curvatures $\rho_{wf}$ in one plane and an infinite radius of curvature in the perpendicular, where $\rho_{wf}$ is the distance between the scatter 56A and the line of curvatures 53O. The location of the point scatter 56A in the plane of the drawing is defined by the polar angle θ and the distance from the center of origin r. The optical energy scattered by the point scatter 56A and collected by the optical probe brings about the following signal $V_{sig}$ in the interferometer output:

$$V_{sig} \sim I(x, y, z) \cdot e^{2ik\rho_{wf}} = I_0 \cdot e^{\frac{-2y^2}{w_y^2}} \cdot e^{2ik\sqrt{x^2+z^2}}.$$

Due to rotation of the shaft 53 (or, alternatively, the movement of the scatter 56A), the signal $V_{sig}$ has rapidly changing phases or carrier modulated with slowly varying envelope:

$$V_{sig} \sim e^{-\frac{2r^2 \cdot \sin^2\Theta\sin^2\tau}{w_y^2}} \cdot e^{2ikr\sqrt{1-\sin^2\Theta\sin^2\tau}}$$

Here, τ=ωt represents real time variable and can be parameterized by A-line numbers in FD-OCT or SD-OCT. It can be seed from the above that the polar angle coordinate is encoded by non-linear phase shifts, or chirps, in the $V_{sig}$ function. In case when the scatter 56A rotation angle $\tau = \omega t$ is substantially small during exposure to the optical energy 55, the signal function can be approximated as $$V_{sig} \approx e^{-\frac{2r^2 \cdot \sin^2 \Theta \tau^2}{w_y^2}} \cdot e^{2ikr\left(1 + \frac{\sin^2 \Theta \tau^2}{2}\right)}.$$

FFT along k-variable "compresses" the signal function in the distance r direction, while still leaving uncompressed polar angle direction:

$$V_r(r') = FFT_k V_{sig} \approx e^{-\frac{2X^2 \tau^2}{w_y^2}} \cdot e^{-ik_0 \frac{X^2 \tau^2}{r}} \cdot PSF(r' - 2r).$$

Here, PSF is a point spread function as conventionally defined in OCT for scatter located at distance r and $X = r \cdot \sin \Theta$. The distance compressed function $V_r$ can be further compressed for the polar angles by many signal processing algorithms known in SAR imaging. One example is to perform a convolution with a chirp function $$CF(\Theta', \tau) = e^{ik_0 r \cdot \sin^2 \Theta' \tau^2} = e^{ik_0 \frac{X'^2 \tau^2}{r}}$$

and then take square magnitude of the convolution output as an image function $$I_{im}(r', \Theta') = \left| \int V_{sig}(r', \Theta) CF(\Theta', \tau) d\tau \right|^2 = \frac{\pi}{\sqrt{\left(\frac{2X^2}{w_y^2}\right)^2 + \left(\frac{k_0(X^2 - X'^2)}{r}\right)^2}} |PSF(r' - r)|^2$$

To appreciate spatial localization capabilities of the Doppler encoding (with the chirp function in this example), i.e. to evaluate spatial resolution for the Doppler encoding imaging, it is convenient to introduce dimensionless variables $$\alpha = \frac{k_0 (2w_y)^2}{4r} \text{ and } \zeta = \frac{\Delta X}{X} = \frac{X - X'}{X}.$$

Then the image function can be expressed as $$I_{im}(r', \Theta') \propto \frac{\pi}{\sqrt{1 + (\alpha \zeta)^2}}$$

so that the dimensionless parameter $\xi_{1/2}$ that corresponds to 3 dB drop in the image function is $$\xi_{1/2} = \frac{\sqrt{3}}{\alpha}.$$

By means of further example consider the optical energy 55 with the central wavelength $\lambda_0 = 0.8$ um focused in one direction to $2w_y = 100$ um and having angular spread between 0.1 rad and $\theta_1 = 0.5$ rad at the working distance r=1 mm. Then parameter $\alpha = 19$ and it would easy to show to anyone skilful in math there are about 20 resolvable spots in polar angular directions while the distance or depth resolution will be the same in conventional OCT.

Figure 9A:
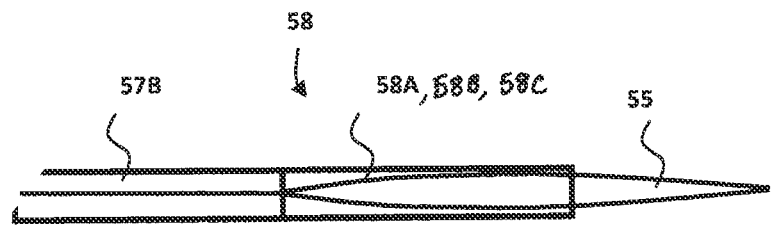
FIGS. 9A-9E illustrates several embodiments of an energy-focusing element for use with the probe of FIG. 8.
Figure 9B:
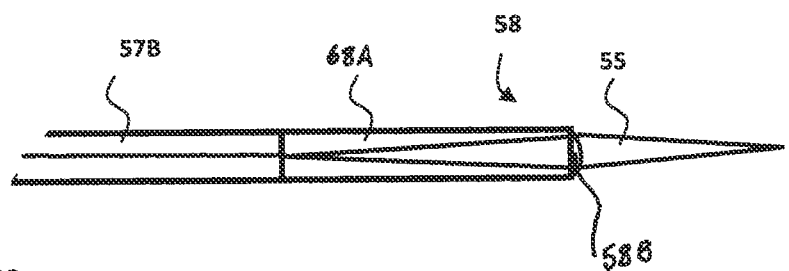
Figure 9C:
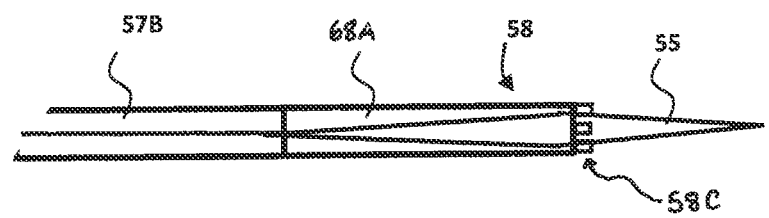
Figure 9D:
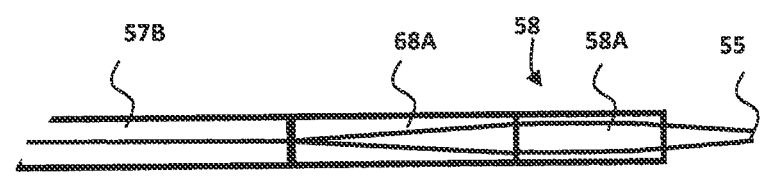
Figure 9E:
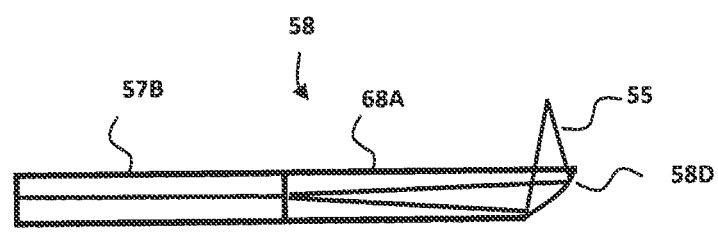
Figure 17B:
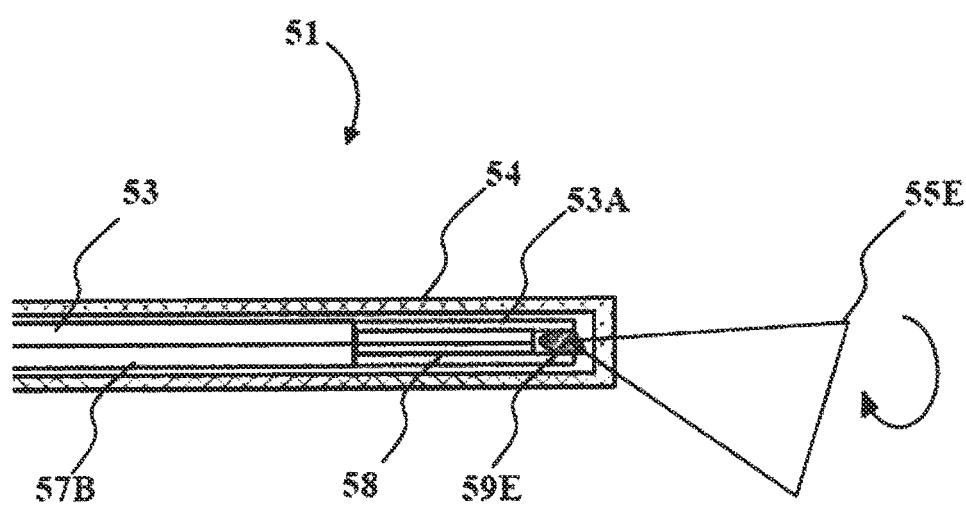
Figure 17B:
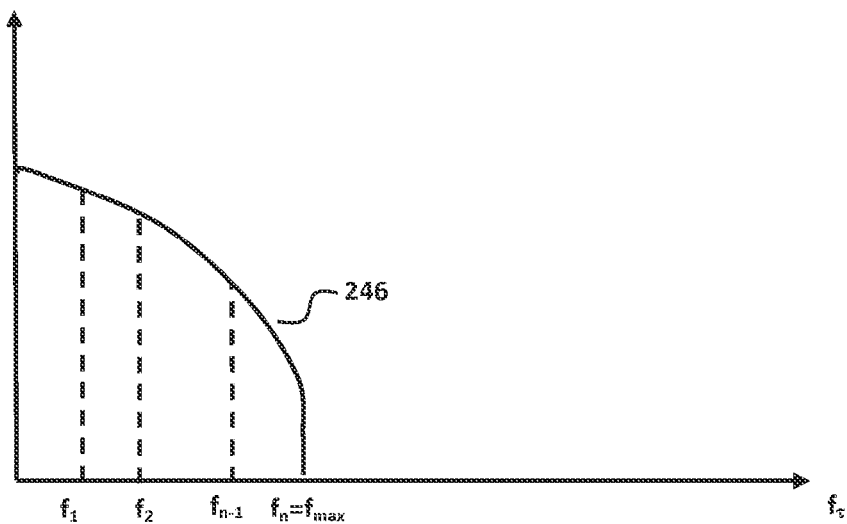

In one example of the embodiment of the distal end 51 of the probe (that is equipped for imaging with Doppler encoding using asymmetrical wavefront shaping shown in FIG. 17B), the shaft 53 is free to rotate inside the sheath 54. The shaft 53 comprises the optical fiber 57B such as a standard single mode fiber. The focusing element 58 described previously is attached to the single mode fiber 57B by means of fusion or adhesive bonding and focuses the optical radiation to required spot size at required working distance. For example, the required spot size can be 100 um and the required working distance can be 1 mm. The GRIN lens 58A (juxtaposed with the glass rod or cylinder 68A, as shown in FIG. 9D for example) can be used as the focusing element 58 in this embodiment and the selection of the GRIN lens, and the cylinder parameters that are required to achieve the chosen spot size can be easily determined by anyone skilful in the field of optics. The directing element 59E (that spreads the optical energy in one direction as well as deflects the optical energy) is also attached to the shaft 53 by means of a mounting tube 53A, which can be for example a metal or glass tube. In one implementation, the directing element 59E can be a modified Powell lens with one tilted surface. The Powell lens design is disclosed in U.S. Pat. No. 4,826,299 and, according to the present invention, can be adopted to fabricate the Powel lens on a small glass cylinder by first polishing a wedge and then shaping the surface (for example, with laser melting of the glass) and further adopted to fabricate the Powel lens that deflects the optical radiation. Specifically the Powel lens with full angle divergence of about 30 degrees from FIG. 16 of U.S. Pat. No. 4,826,299 and the last surface of the Powel lens can be polished at the angle to generate deflection angle approximately half of the divergence angle. In this manner, the directing element 59E forms the imaging line 55E in the tissue at the distance approximately 1 mm or less from the probe with dimension of about 0.5 mm. When the shaft 53 rotates, the imaging line 55E also rotates and covers a circle of approximately 1 mm in diameter in this exemplified arrangement. The sheath 54 may include a transparent window 54E securely attached to the sheath by adhesives or fusion process. Alternatively, the sheath material itself may act as the window 54E. Other means of decoding the radial position decoded with Doppler shifts broadening or speckle correlation broadening are also possible and will be recognized by a person of skill in the field. For example one can appreciate that FFT "across" A-lines, i.e. FFT in space of the signal collected by the distal end 51 results in the spectrum 246 of finite width with maximal frequency $f_{max}$ as illustrated in FIG. 17BB. The maximal frequency $f_{max}$ is determined by the speckles decorrelation time, i.e. by the decorrelation speed of the tissue response illuminated by the line 55F of FIG. 17A. Referring to the FIGS. 17A, 17B, and 17BB the maximal frequency $f_{max}$ is determined by the distal end 51 angular velocity of rotation $\Theta$, line width $w_y$, and the spread of the polar angle $\theta_{max}$.

$$f_{max} \propto \frac{2w_y}{\omega \cdot r \cdot \sin \Theta_{max}}$$

Thus applying band pass-filters in the f FFT space one can select component of the signal generated by the line 55F that corresponds to different ranges of polar angles. For example, one can perform FFT of the signal along variable, filter frequency components with a band-pass filter with the pass band between $f_{n-1}$ and $f_n$, frequencies, perform inverse FFT of the band pass filtered data, then perform standard OCT processing along k variables, and finally assign reconstructed data to polar angle range that corresponds to the range of frequencies $f_{n-1}$ and $f_n$.

Figure 17C:
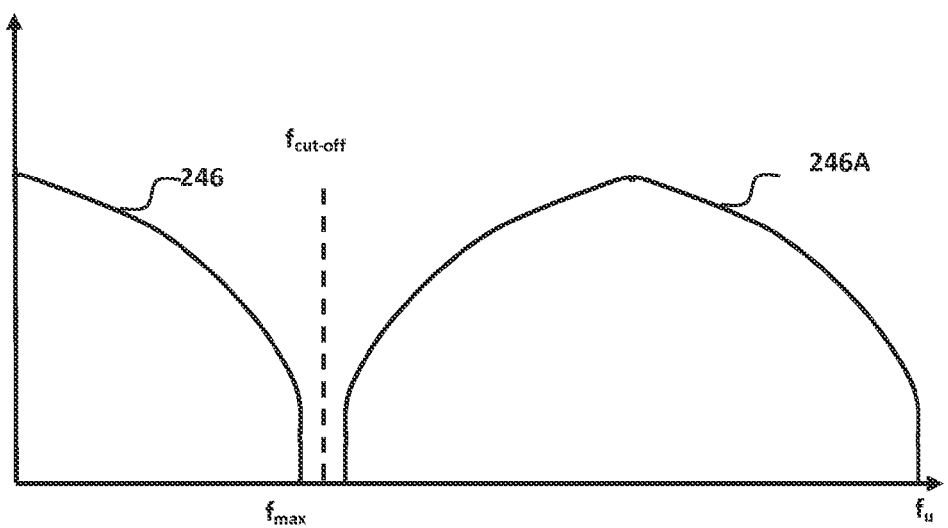
Figure 17C:
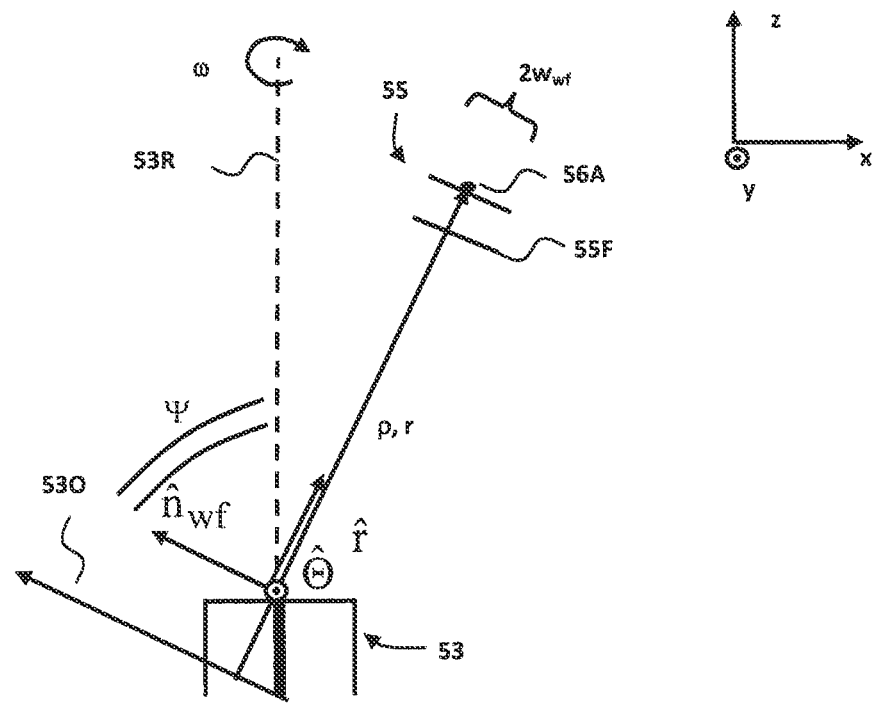

It is possible to further improve resolution of the Doppler encoding imaging by asymmetrically shaping optical energy so that that the positions of light-scattering points associated with the tissue being imaged are encoded by Doppler shifts (as illustrated in FIG. 17C) and not just by the Doppler broadening or chirp as illustrated in FIG. 17A. Specifically, FIG. 17C shows a diagram similar to that of FIG. 17A but with the optical energy 55 focused to a plane 55E defined by a unit normal vector $\hat{n}_{lc} = -\sin \Psi \hat{x} + \cos \Psi \hat{z}$. Here, the unit vectors $\hat{x}$, $\hat{y}$, $\hat{z}$ represent the reference frame xyz with the rotational axis 53R, or equivalently with a vector $\vec{\omega}$ aligned along z directions and the unit vector $\hat{n}_{lc}$ having an angle $\Psi$ with the rotational axis 53R. The spatial extend of the optical energy focusing in the plane 55E can be quantified by the focusing with $2w_{wf}$. The wavefronts 55F are the cylindrical surfaces with the line of curvatures 53O aligned along the vector $\hat{n}_{lc}$. The scatterer 56A lies in the plane 55E at time t=0 characterized by vector $\vec{r}_0 = r \cos \Theta \cdot \vec{r} + r \sin \Theta \cdot \vec{\Theta}$, where orthogonal unit vectors $\hat{r} = \cos \Psi \hat{x} + \sin \Psi \hat{z}$ and $\hat{\Theta} = \hat{y}$ define the reference frame in the plane 55E so that location $\vec{r}_0$ of the scatter 56A in this plane can be specified by the radial distance r and the polar angle $\Theta$. Due to rotation with the angular velocity $\vec{\omega}$, the position of the scatter 56A at time t for sufficiently small times is: $\vec{r}(t) = \vec{r}_0 + \vec{v} \cdot t = \vec{r}_0 + \vec{\omega} \times \vec{r}_0 \cdot t = r \cos \Theta \cdot \vec{r} + [r \sin \Theta - \cos \Psi r \cos \Theta \tau] \hat{\Theta} + r \sin \Theta \tau \hat{x}$. Here $\tau = \omega t$ again represents real time variable and can be parameterized by A-line numbers in FD-OCT or SD-OCT. Such motion of the scattering point 56A results in the following time dependence of the distance between the scatter 56A and the line of curvatures 53O.

$\rho_{wf} = |\vec{r} + \vec{z}_0 - \hat{n}_{lc}(\hat{n}_{lc} \cdot (\vec{r} + \vec{z}_0))| = |r \cos \Theta \cdot \vec{r} + \vec{z}_0 + [r \sin \Theta - \cos \Psi r \cos \Theta \tau] \hat{\Theta} + r \sin \Theta \tau \hat{x} - \hat{n}_{lc} r \sin \Theta \tau (\hat{n}_{lc} \cdot \hat{x}) - \hat{n}_{lc}(\hat{n}_{lc} \cdot \vec{z}_0)|$ Expanding unit vector $\hat{x} = \cos \Psi \cdot \hat{r} - \hat{n}_{lc} \sin \Psi$, and $\vec{z}_0 = z_0 \sin \Psi \cdot \vec{r} + \cos \Psi \hat{n}_{lc} = r_0 \cdot (\hat{r} + \text{ctg } \Psi \hat{n}_{lc})$ the distance $\rho_{wf}$ can be expressed as $\rho_{wf} = |[r \cos \Theta + r_0 + \cos \Psi r \sin \Theta \tau] \cdot \hat{r} + [r \sin \Theta - \cos \Psi r \cos \Theta \tau] \hat{\Theta} + [(\sin \Psi r \sin \Theta \tau)] \hat{n}_{lc}$.

By keeping only the lowest order terms in $\tau$, the expression for $\rho_{wf}$ can be further simplified $$\rho_{wf} = \sqrt{r^2 + r_0^2 + 2rr_0 \cos \Theta + 2rr_0 \cos \Psi \sin \Theta \tau} \approx (r + r_0)\left(1 + \tau \frac{r \cdot r_0}{(r + r_0)^2} \sin \Theta \cos \Psi\right),$$

thus making the phase term in the interferometric signal $$V_{sig} \sim \cdot e^{2ik(r+r_0)\left(1+\tau \frac{r r_0}{(r+r_0)^2} \sin\Theta \cos\Psi\right)}.$$

It would appreciated by an artisan skilled in the field of coherent imaging that the polar angle coordinate is encoded by frequency shifts in the $V_{sig}$ function. Therefore, it would be recognized by how to decode the polar angle coordinate in implementing the embodiment of the invention. For example, a sequence of FFT and convolution with appropriate function can be used. Specifically, FFT signal processing step "compresses" the signal function in the distance r direction, while still leaving uncompressed polar angle direction:

$$V_r(r') = FFT_k V_{sig} \approx e^{-2ik_0 \tau \frac{r r_0}{(r+r_0)} \sin\Theta \cos\Psi} \cdot PSF(r').$$

The distance compressed function V, can be further compressed for the polar angles by many known signal processing algorithms. One example is to perform a convolution with a frequency shift function $$SF(\Theta', \tau) = e^{2ik_0 \tau \frac{r r_0}{(r+r_0)} \sin\Theta' \cos\Psi}$$

and then take square magnitude of the convolution output as an image function $$I_{im}(r', \Theta') = \left| \int V_{sig}(r', \Theta)) SF(\Theta', \tau) d\tau \right|^2 = \left| e^{-i2k_0 \tau \frac{r r_0}{r+r_0}[\sin\Theta - \sin\Theta']\cos\Psi} \Big|_{-\frac{\tau_0}{2}}^{\frac{\tau_0}{2}} \right|^2 |PSF(r' - r)|^2.$$

Here $\tau_0$ is passing time of the scatterer 56A through the plane 55E of the focused energy which can be estimated as follows:

$$\tau_0 = \omega \frac{2w_{wf}}{\cos\Psi} / v_x = \omega \frac{2w_{wf}}{\cos\Psi} / \omega r \sin\Theta = \frac{2w_{wf}}{r \sin\Psi \sin\Theta}$$

$$I_{im}(r', \Theta') \propto \left| \frac{\sin\left(\left[\frac{\sin\Theta - \sin\Theta'}{\sin\Theta}\right] \frac{k_0 2 w_{wf} r_0}{r + r_0} \cdot \tan^{-1}\Psi\right)}{\left[\frac{\sin\Theta - \sin\Theta'}{\sin\Theta}\right] \frac{k_0 2 w_{wf} r_0}{r + r_0} \cdot \tan^{-1}\Psi} \right|^2.$$

To appreciate spatial localization capabilities of the embodiment enabled to operate with Doppler encoding employing the frequency shift function in this example, (i.e. to evaluate spatial resolution for the Doppler encoding imaging), it is convenient to introduce dimensionless variables $$\zeta = \frac{\sin\Theta - \sin\Theta'}{\sin\Theta} \quad \beta = \frac{k_0 2 w_{wf} \cdot r_0}{r + r_0}.$$

Then the image function can be expressed as $$I_{im}(r', \Theta') \propto \cdot \text{sinc}^2\left(\frac{\beta \zeta}{\tan\Psi}\right)$$

so that the dimensionless parameter $\xi_{1/2}$ that corresponds to 3 dB drop in the image function is $$\xi_{1/2} = \frac{1.4 \tan\Psi}{\beta}.$$

By means of further example consider the optical energy with the central wavelength $\lambda 0=0.8$ um focused in one direction to 2wwf=30 um with the angle between the normal to the focus plane and the rotational axis $\Psi=75$ degree. If the optical energy has the angular spread between 0.1 rad and $\theta 1=0.5$ rad, working distance r=2 mm and the wavefront curvature radius r0=0.5 mm, the parameter $\beta \sim 78$ and it would easy to show to anyone skilful in math there are about 25 resolvable spots in polar angular directions while the distance or depth resolution is the same in conventional OCT imaging. The preferred embodiment of the probe distal end to carryout the Doppler encoding imaging of FIG. 17C is similar to the distal end embodiment shown in FIG. 17B with an additional tilted surface polished on the directing element 59E so that the imaging line 55E is deflected from the drawing plane by angle 90–$\Psi$. It is also possible to further improve resolution of the Doppler encoding imaging with asymmetrically shaped optical energy as shown in FIG. 17A by additional axial translation of the asymmetrically shaped energy distribution with respect to the imaged tissue during imaging, for example by translating the distal end of the probe. In this case different light-scattering points associated with the tissue being imaged are encoded by different Doppler shifts due to different angles between the optical energy wavefront and local velocity of the tissue relative to the optical energy. The axial translation of the distal end can be implemented by translating the probe by the translation stages of the DU 101 of FIG. 2B. Alternatively the internal shaft can be translated with the translation stages of DU 101 while keeping the outer sheath stationery resulting in axial translation of the asymmetrically shaped energy distribution. It is also possible to modify the DU 101 to incorporate additional translational means for example in the form of solenoid or piezoelements dedicated to imposing the Doppler shifts to the asymmetrically shaped energy distribution by means of axial translation.

Figure 21A:
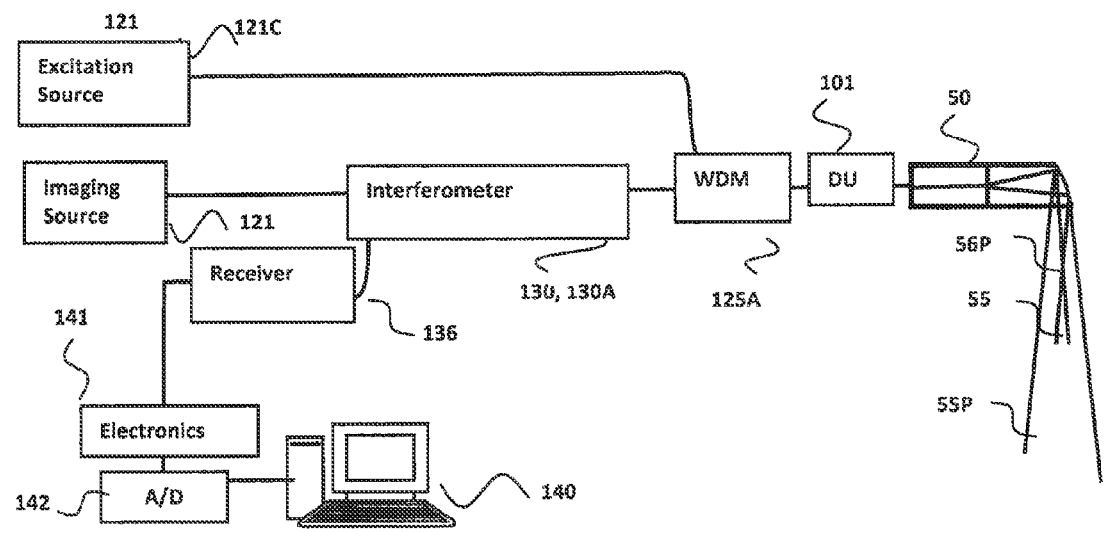
FIGS. 21A, 21B and 21C are diagrams illustrating a related embodiment of a photoacoustic imaging system.
Figure 21B:
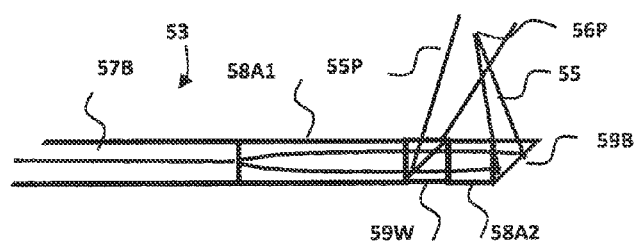
Figure 21C:
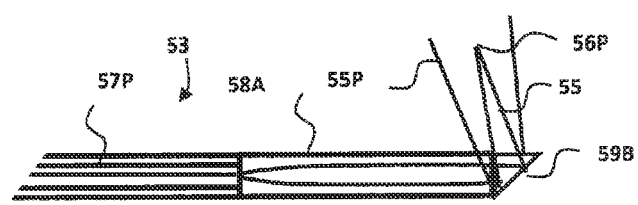

It is also possible to encode the different position of the tissue interrogated with such asymetrically shaped energy with different Doppler shifts by additionally illuminating the tissue with pulsed or modulated optical energy that causes motion of the tissue by means of thermal expansion and/or acoustic transients generated by absorbing this additional energy. The modifications required to implement outcoupling of this additional energy are described in the photoacoustic section of this disclosure as shown in FIG. 21B and FIG. 21C.

Axial translation of the optical energy with respect to the imaged tissue resulting in different Doppler shifts due to different angles between the optical energy wavefront and local velocity of the tissue relative to the optical energy can be advantageously applied to multi-view arrangements of FIGS. 11A-11I and related embodiments of this invention. Consider as an example the dual view arrangement shown in FIG. 11B, the interferometric signal acquired from either the forward view portion of optical energy 55F or the side view portion 55S has in-domain frequency content 246 characterized by maximal frequency finax as illustrated in FIG. 17CA. When the probe of FIG. 11B is translated axially during imaging, the backscattered energy from the forward portion 55F experiences Doppler shifts, while the backscattered energy from the side view portion experiences significantly smaller Doppler shifts or no shifts at all. Thus the spectral components associated with the forward view are up-shifted by the Doppler shifts and characterized by new extent 246A of FIG. 17CC that can be separated from the substantiall unchange extend of the side view components 246 by using high pass filter with the cut-off frequency $f_{cut-off} > f_{max}$.

Alternative way of imposing the differential phase modulation of different views of the probe is to offset the side view portion of the optical energy 55S from the axis of the probe as indicated in FIG. 17CB. FIG. 17CB shows cross-section the probe distal end 51 with a beam directing arrangement 59OFF rotating with angular velocity that allows the side view portion 55S to exit the probe with the offset $\Delta$ relative to the probe axis. In this case the side view portion of the back-scattered energy experiences significant Doppler shifts while the forward view portion remains unchanged thus allowing separation of interferometric signals associated with the different viewing angles. The directing arrangement 59OFF with the offsetting capabilities can be realized for example by attaching the offset focusing elements shown in FIG. 11E to the rotating shafts of the probes of the present invention.

Figure 17D:
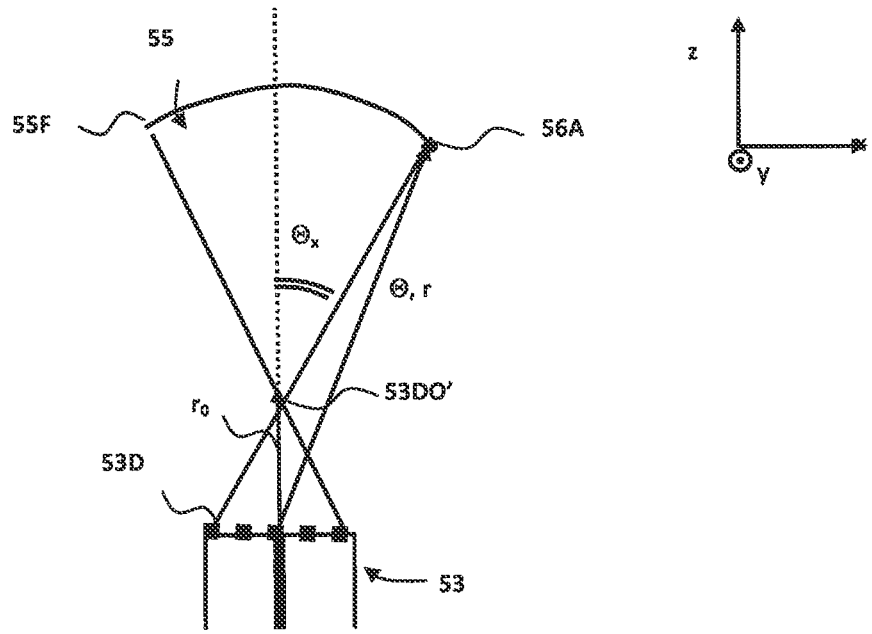
Figure 17C:
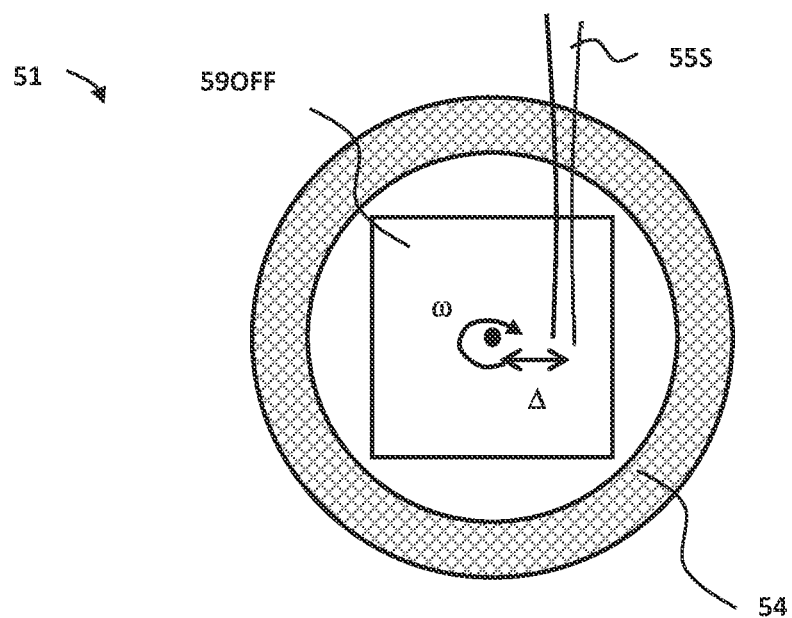

For embodiments of the invention carrying out the Doppler encoded imaging with FD-OCT, it is possible to use the wavelength tuning of the optical source to implement fast motion of properly shaped wavefronts of the optical energy without need for mechanical rotation of the probe shaft. This can be achieved by using a dispersing element such as a grating, a prism, a diffractive optical element, or a holographic element that converts the wavelength tuning to the motion of the optical energy wavefronts resulting in Doppler shifts and/or Doppler broadening. In contrast to the prior art of the spectral encoding of FIG. 14A, the imaging with Doppler encoding does not require focusing of the optical energy at each wavelength thus decreasing complexity of the probes distal end arrangements and removing the trade-off between lateral resolution and the depth resolution. To show how to practice the Doppler encoding imaging with the wavelength tuning, FIG. 17D depicts the optical energy 55 emitted from the stationary probe shaft 53 with the dispersing element 59D attached to the shaft 53. The dispersing element 59D is located in the center of the reference frame and aligned so that the optical energy 55 pivots around the center of the reference frame in the plane of the drawing when the wavelength changes. The optical energy 55 is substantially focused to the drawing plane of FIG. 23D and have Gaussian intensity distribution $$I(y) = I_0 \cdot e^{\frac{-2y^2}{w_y^2}}$$

in the y direction. At the same time the optical energy 55 is shaped by the dispersing element 59D to have divergence in x-z plane. For example the optical energy can be divergent Gaussian beam with intensity $$I(r, \Theta) = I_0 \cdot e^{\Theta_x^2 (r\cos\Theta - r_0)^2} \approx I_0 \cdot e^{\Theta_x^2 (r - r_0)^2}$$

and the wavefronts 55F have the curvature center 53DO' displaced from the center of origin by $r_0$. FIG. 23D shows the reference frame that moves with the optical energy when the wavelength changes therefore the scatter 56A moves in an approximately along circular trajectory centered on the center of the reference frame. In addition, the displacement of the curvature center 53DO' is generally wavelength dependent: $\vec{r}_0 = \vec{r}_0(k)$. The location of the point scatterer 56A in the plane of the drawing is defined by polar angle $\theta_0$ and the distance r from the center of origin for the center wavenumber $k_0$. The dependence of the polar angle on the wavenumber is known once the dispersive element 56D is specified and can be approximated as linear $\Theta = \Theta_0 + \Theta_k(k - k_0)$. The optical energy scattered by the point scatter 56A and collected by the probe shaft 53 results in the following signal $V_{sig}$ in the interferometer output:

$$V_{sig} \approx I_0 \cdot e^{\frac{-2\Theta^2 r^2}{\Theta_x^2 (r-r_0)^2}} \cdot e^{2ik\sqrt{r^2+r_0^2-2rr_0+rr_0\Theta^2}} =$$

$$I_0 \cdot e^{\frac{-2\Theta^2 r^2}{\Theta_x^2 (r-r_0)^2}} \cdot e^{2ik\sqrt{(r-r_0)^2+rr_0\Theta^2}} = I_0 \cdot e^{\frac{-2\Theta^2 r^2}{\Theta_x^2 (r-r_0)^2}} \cdot e^{2ik(r-r_0)\left[1-\frac{rr_0\Theta^2}{2(r-r_0)^2}\right]} \approx$$

$$I_0 \cdot e^{\frac{-2(\Theta_0+\Theta_k(k-k_0))^2 r^2}{\Theta_x^2 (r-r_0)^2}} \cdot e^{2ik(r-r_0)\left[1-\frac{2rr_0\Theta_0\Theta_k(k-k_0)}{(r-r_0)^2}\right]}$$

It would be immediately appreciated by anyone skilful in the field of coherent imaging that while the distance r coordinate is encoded by the frequency of $V_{sig}$ as customary in FD-OCT, the polar angle $\Theta_0$ is encoded by non-linear frequency shifts or chirps in the $V_{sig}$ function.

To decode the spatial information, the signal function Vsig can be "compressed" for example by performing convolution with a matched filter function $$MF2(r', \Theta') = e^{-2ik(r'-r_0)\left[1-\frac{2rr_0\Theta_0'\Theta_k(k-k_0)}{(r-r_0)^2}\right]}.$$

Then a square magnitude of the convolution output can be used as an image function: $I_{im}(r',\Theta'_0) \propto |\int V_{sig}(r,\Theta_0)MF2(\Theta'_0, r')dk|^2$. The image function $I_{im}$ can be approximated as a product of a customary depth PSF function corrected for the finite exposure time of the scatter 56A to the optical energy 55 and a function that determines resolution for the polar angle.

$$I_{im}(r', \Theta'_0) \propto \frac{\pi}{\sqrt{\left(\frac{2\Theta_k^2 r^2}{\Theta_x^2(r-r_0)^2}\right)^2 + \left(\frac{4rr_0(\Theta_0-\Theta'_0)\Theta_k}{(r-r_0)}\right)^2}} \approx$$

$$\frac{\pi}{\frac{2\Theta_k^2 r^2}{\Theta_x^2(r-r_0)^2}\sqrt{1+\left(2r_0\Theta_x \cdot \frac{\Theta_x}{\Theta_k} \cdot \frac{(r-r_0)}{r}(\Theta_0-\Theta'_0)\right)^2}}$$

To appreciate localization properties of the Doppler encoding with the wavelength tuning, it is convenient to introduce dimensionless variable $$\delta = 2r_0\Theta_x \cdot \frac{\Theta_x}{\Theta_k} \cdot \frac{(r-r_0)}{r}$$

and define $\Delta\Theta = \Theta_0 - \Theta'_0$. One can use, for the purpose of an example, the relation between the probe shaft diameter and the maximum divergence angle $D_{probe} = 2r_0\Theta_x$. One can also assume an exemplary Littrow configuration of the dispersing element $$\Theta_k \approx \frac{\tan\Theta_{dif}}{k_0} \approx \frac{K_g}{2k_0^2\sqrt{1-\left(\frac{K_g}{2k_0}\right)^2}} \approx \frac{K_g}{2k_0^2},$$

and further assume that the optical energy shaping or divergence is implemented by a "chirp" in the dispersive element grating.

$$\Theta_x \approx \frac{\Delta K_g}{k_0},$$

where $K_g$ is the grating wavenumber. Then, the dimensionless parameter can be further simplified as $$\delta = D_{probe}k_0 \cdot \frac{\Delta K_g}{2K_g} \cdot \frac{(r-r_0)}{r}$$

and the image function can be expressed as $$I_{im}(r', \Theta) \propto \frac{\pi}{\sqrt{1+(\delta\Delta\Theta)^2}}$$

so that the polar angle $\Delta\Theta_{1/2}$ that corresponds to 3 dB drop in the image function is $$\Delta\Theta_{1/2} = \frac{\sqrt{3}}{\delta}.$$

In another example, the optical energy 55 can be considered with the central wavelength $\lambda_0 = 1$ um having half angle divergence $\Theta_x$ of 0.3 radian at the working distance r=1 mm. The diffractive element has a chirped pitch ranging from 1200 lines/mm to 600 lines/mm, and the probe shaft diameter is 0.25 mm. Then the parameter $\delta$ is $\delta=243$ and it would easy to show there are about 80 resolvable spots in polar angular directions while the depth resolution is the same as in conventional OCT imaging. The preferred embodiment of the probe distal end to carryout the Doppler encoding imaging of FIG. 17D is similar to the distal end embodiment shown in FIG. 17B with the chirped grating with parameters described above fabricated on the focusing element 58 for example as shown in FIG. 7C. Also the directing element 59E should be removed or replaced with the directing element 59A as shown in FIG. 7A to direct the optical energy in desired location.

Accordingly, an embodiment of the navigational system of the invention includes means structured to outcouple light towards the ambient medium such as to define multiple beams of the outcoupled light, and to enable the data-processing unit to interferometrically differentiate between first and second point of the ambient medium based on difference in rate of phase change of light from said multiple beams return to the second means by the ambient medium.

Overall, means for enabling an imaging probe to employ spectral, frequency and Doppler encoding can be advantageously combined in a specific embodiment for use in diagnostic imaging and guidance. Such combinations are also within the scope of the present invention.

Embodiments Configured to Determine Blood Oxygenation.

Figure 18A:
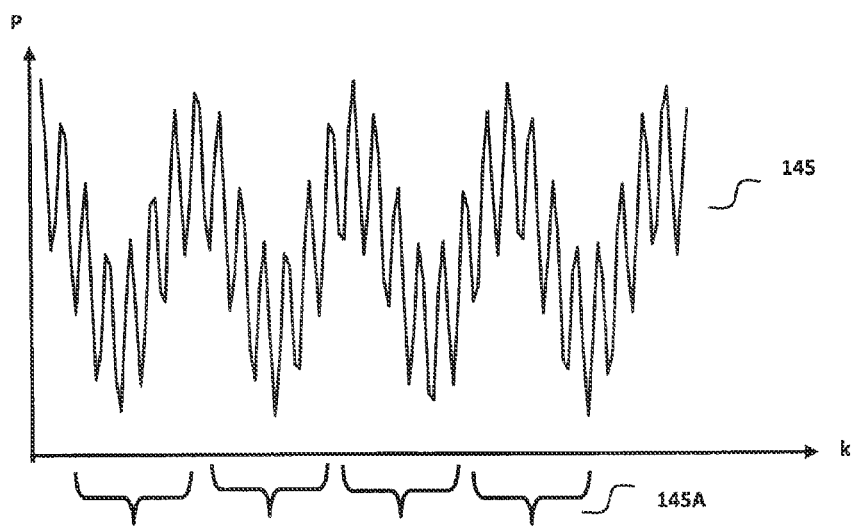
FIGS. 18A, 18B, 18C, 18D depict implementations of the invention employed in spectral contrast imaging.
Figure 18B:
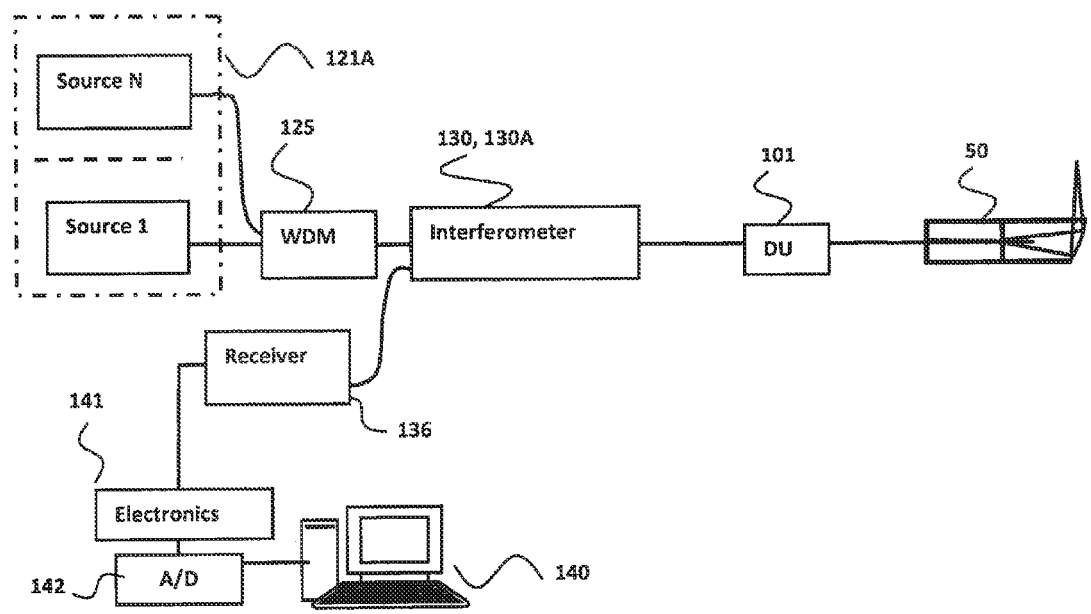
Figure 18C:
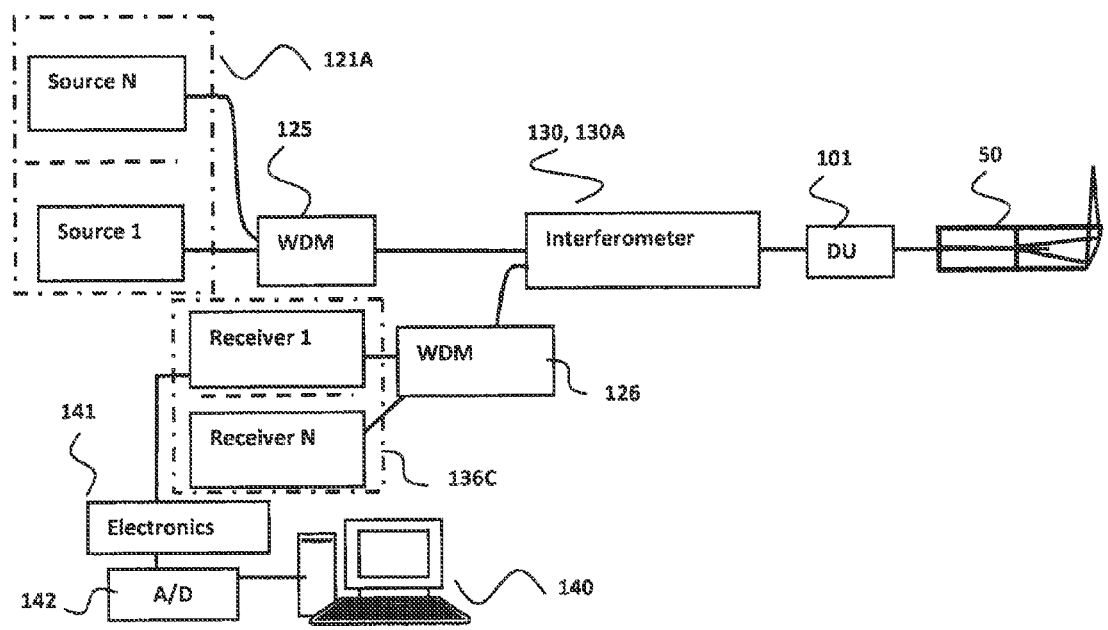
Figure 18D:
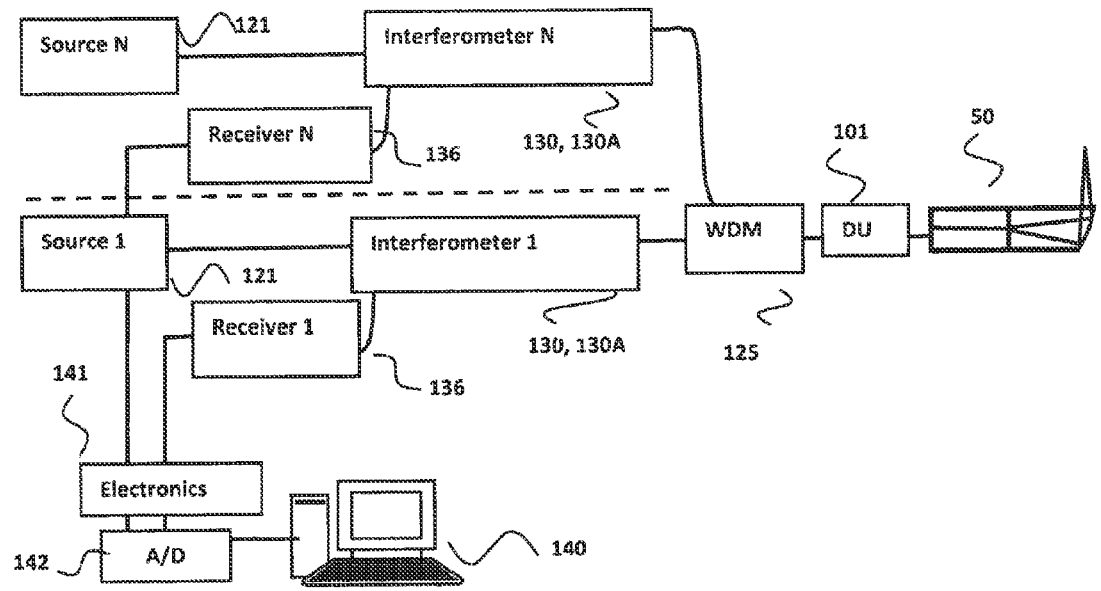
Figure 19A:
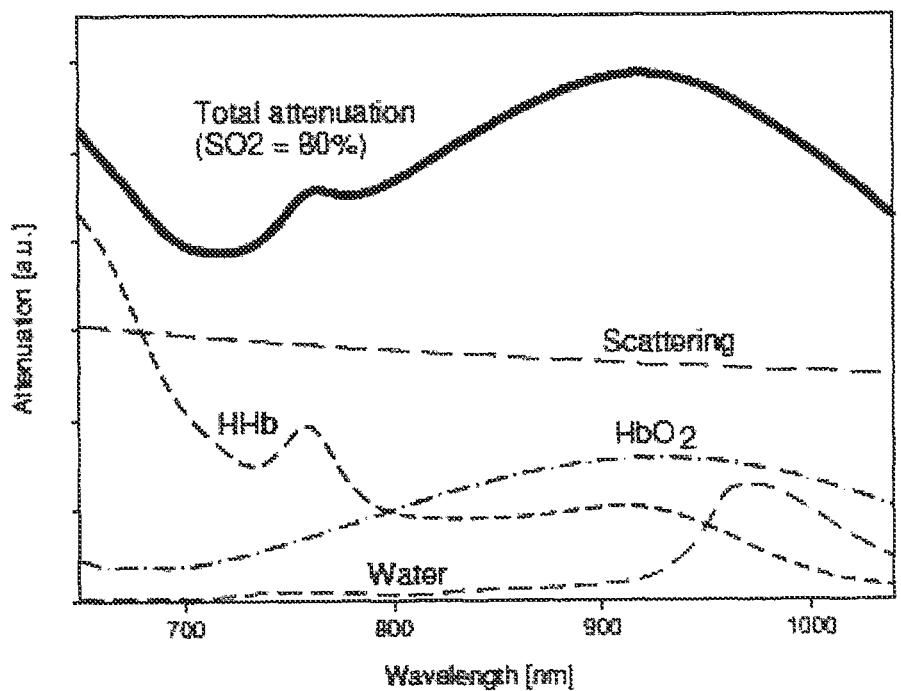
FIGS. 19A and 19B are graphs presenting, respectively, spectral properties of blood and an example of the spectral dependence of an OCT signal.

Turning attention to implementation of OCT imaging with spectral contrast required for spectral absorbance mapping in tissue, FIGS. 18A-18D show different proximal end arrangements for such imaging, which can also be used for extending spectral range in the frequency, Doppler and spectral encoding imaging described above. FIG. 18A, which is relevant for FD-OCT and SD-OCT, shows an interferogram 145 that can be separated into different portions 145A that correspond to different spectral regions of the source 121. The portions 135A can be processed independently to extract properties of tissue that affect spectral content of the returned light. The disadvantage of this approach is loss of spatial resolution and limited spectral range determined by the spectral range of the single source 121. Alternative embodiment shown in FIG. 18B uses a plurality 121A of broad band or swept frequency sources. Each source of the plurality 121A covers different spectral region and can be coupled to the separate path interferometer 130 or the common path interferometer 130A via a division wavelength multiplexer, or a switch 125. The light from the plurality of the sources 121A is directed to the probe 50 via the drive unit 101. The interferogram is detected by the receiver 136, pre-amplified and filtered by the electronics module 141, digitized by the A/D converter 142, and processed by the CPU 140 similar to the arrangements above. The spectral analysis of the interferogram 145 can be implemented by analyzing its different portion as shown in FIG. 19A. Alternatively a wavelength demultiplexer or a switch 126 can be used that sends different spectral regions after the interferometer 130 or the interferometer 130A to plurality of receivers 136C which then are pre-amplified and filtered separately in the electronics module 141 and digitized by separate channels of the A/D converter 142 as shown in FIG. 18C. Finally the arrangement shown in FIG. 18D with a plurality of interferometers 130 or 130A, with each interferometer having its own source 121 and own receiver 136 can be used. In the arrangement of FIG. 18D the light from different interferometers is directed to the drive unit 101 and then to the probe 50 via the WDM or the switch 125.

Figure 19B:
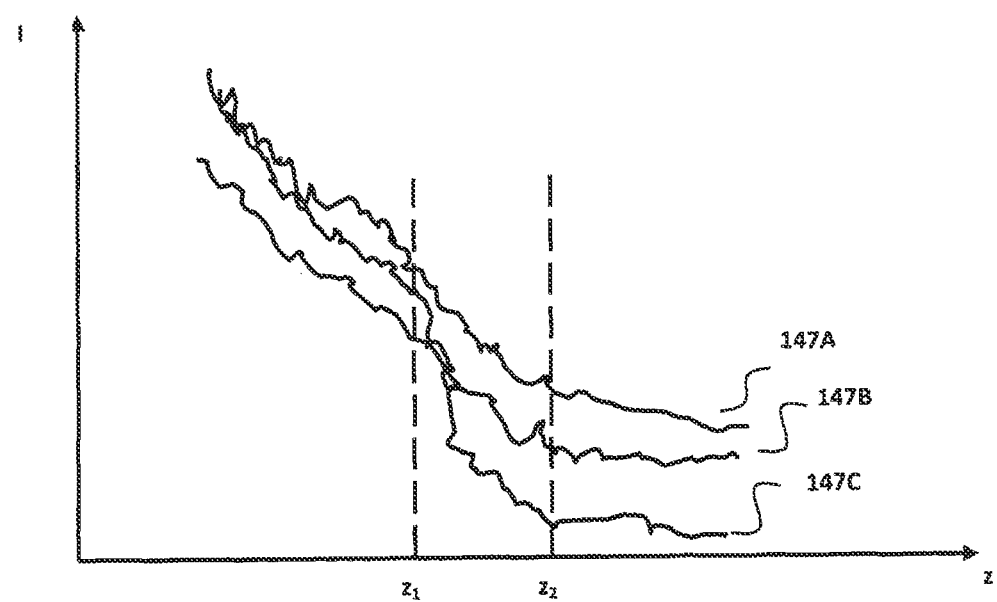

Using blood oxygenation mapping as a descriptive example for spectral absorbance mapping, FIG. 19A illustrates NIR spectral absorption in blood dominated by three chromophores: deoxyhemoglobin (HHb), oxyhemoglobin (HbO2), and water. In addition, a spectral dependence of scattering and example of total attenuation for blood hemoglobin oxygen saturation SO2=80% are shown in FIG. 19A. In contrast with the slow varying wavelength dependence of the scattering, the optical absorption of HHb and HbO2 both have strong wavelength dependence. For example, wavelengths $\lambda_1$~700 nm, $\lambda_2$~800 nm, $\lambda_3$~900 nm indicate spectral regions where absorption of HHb is substantially larger than, equal to, and smaller than absorption of HbO2, respectively. For all the three wavelengths $\lambda_1$ $\lambda_2$ $\lambda_3$ hemoglobin absorption is substantially larger than that of water. By analyzing OCT signal I(z) (z is depth in tissue) at different wavelengths, extraction of tissue absorption coefficients is possible allowing determination of hemoglobin concentration and oxygenation level. The OCT signal I(z) can be in the context of this aspect of the invention the magnitude of processed interferogram, for example magnitude of power FFT output in FD-OCT and SD-OCT. The dependence of OCT signal I(z) on scattering and absorptive properties of the tissue is known and can be modeled for example as described by Ilya Turchin et al in *Journal of Biomedical Optics*, 10(6), 06024 (November/December, 2005). At small depths, such dependence will be dominated by Beer's law attenuation resulting in exponential type decay I(z)∝exp(−2$\mu_{eff}$z) where $\mu_{eff}$ is effective OCT signal decay coefficient which can be approximated as a sum of the scattering coefficient and the absorption coefficient $\mu_{eff} \approx \mu_s + \mu_a$. At larger depths, diffusive regime OCT signal will result in more complicated dependence as described by Turchin et al with nevertheless dominating exponential decay. FIG. 19B illustrates exemplary dependence of OCT signals 147A, 147B, 147C on the tissue depth for the three wavelengths $\lambda_1$ $\lambda_2$ $\lambda_3$ of FIG. 19A respectively also indicating the regions $z_1$-$z_2$ that need to be analyzed to extract hemoglobin concentration and oxygen saturation. For example, the measured OCT signals 147A, 147B, 147C at each wavelength $\lambda_1$ $\lambda_2$ $\lambda_3$ can be fitted with the modeled OCT signals at each wavelength $\lambda_1$ $\lambda_2$ $\lambda_3$ with varying scattering and absorption coefficients until a good fit is obtained. The modeled OCT signals can be approximated in many practical cases by simple exponentially decay as described above. The absorption coefficient in the tissue can be written as the linear sum of the individual absorption contributions of each chromophore (neglecting water absorption) $\mu_a(\lambda) = \alpha_{HHb}(\lambda)c_{HHb} + \alpha_{HbO_2}(\lambda)c_{HbO_2}$ where $\alpha_{HHb}(\lambda)\alpha_{HbO_2}(\lambda)$ are the wavelength dependent specific absorption coefficients of HHb and HbO2 respectively which are known with high accuracy and $c_{HHb}$ $c_{HbO_2}$ are HHb and HbO2 concentrations that need to be determined. The scattering coefficient can be written as $\mu_s(\lambda) = \alpha_{scat}(\lambda)\eta$ where $\alpha_{scat}(\lambda)$ is normalized scattering efficiency and represents slow varying wavelength dependence that may be neglected in most practical cases while η is wavelength independent constant that represents dependence of scattering on hemoglobin concentration in tissue. Since there are three independent unknown parameters (HHb and HbO2 concentrations and parameter η, fitting three independent OCT signals 147A, 147B, 147C for the three wavelengths $\lambda_1$ $\lambda_2$ $\lambda_3$ with the model OCT signal for three wavelengths allows determination of these unknown parameters and therefore determination of hemoglobin concentration $c_{Hb} = c_{HbO_2} + c_{HHb}$ and oxygen saturation $$SO_2 = \frac{^cHbO_2}{^cHbO_2 + ^cHHB} \times 100\%.$$

The method described above for determination of blood oxygenation can be used for determination of concentration of other chromophores for example lymph liquid.

The scattering coefficients of tissue can be much larger than absorption coefficients. As a result direct measurements of absorptive optical properties of tissue can have limited sensitivities. In addition, the large optical scattering of denser tissue limits imaging depth to few mm. In order to overcome these shortcomings probes that combine use of optical and ultrasound energies can be used as described in the next embodiment.

Photoacoustic Embodiments.

To determine chromophores concentrations for example concentrations of HHb and HbO2 in tissue indirect measurement of absorption coefficients by means of photoacoustic imaging can be used. This can be done by detecting transient and inhomogeneous heating of regions where transient light is absorbed. For example, it is possible to detect the inhomogeneous heating by detecting ultrasound transients generated by the heated regions illuminated by time-varying optical energy due to thermal expansion of those regions as described by Mingua Hu et al in *Review of Scientific Instruments* 77, 04101(206). In embodiments of the imaging apparatus 150 for indirect measuring or mapping of absorption coefficients using photoacoustic effects, the imaging console 100 has the same components as in the embodiment of the imaging console with the acoustic energy described before. In addition, a time-varying or an excitation optical source 121C with at least one optical wavelength efficiently absorbed by the tissue chromophores illuminates airway wall and/or parenchyma. The inhomogeneous tissue heating due to optical absorption results in inhomogeneous time-varying thermal expansion of tissue. This expansion generates ultrasound transients that can be detected by the ultrasound transducer 65 as previously described. By analyzing time arrival and magnitude of the ultrasound transients, the mapping of tissue absorption coefficients can be done. Such analysis is particular simple and the ultrasound generation is particular efficient if the optical transients from the excitation source 121C are in the form of short pulses so that condition known as the stress confinement is met. Other transients such as a chirp, i.e. modulated optical energy with variable modulation frequency, can be used and usual matched filter processing can be applied for absorption coefficient mapping.

Figure 20A:
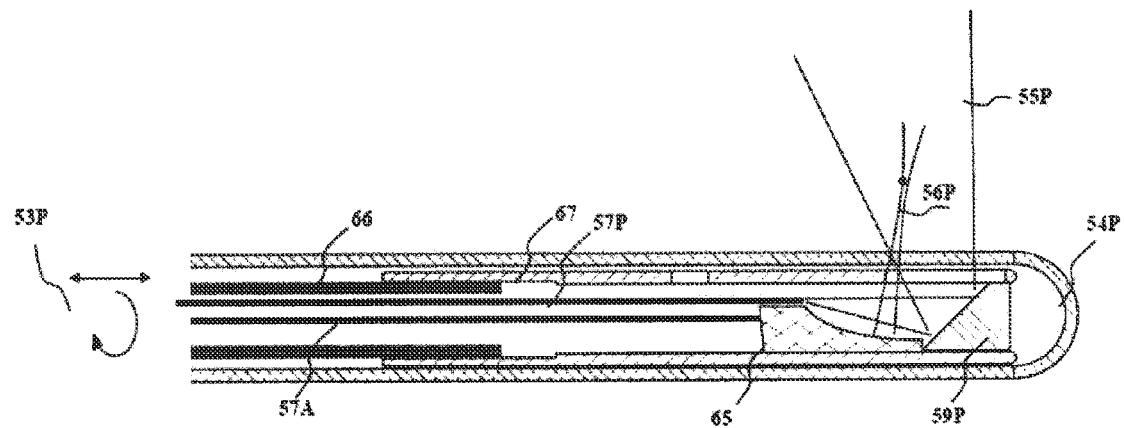
FIGS. 20A and 20B show embodiments of photoacoustic imaging probe and its use in a system of the invention.

In some embodiment of the photoacoustic imaging with the distal end arrangement shown in FIG. 20A, an optical energy 55P from the excitation source 121C is delivered to the tissue through the probe 50 consisting of a shaft 53P and a sheath 54P. In this embodiment the shaft 53P is similar to the shaft 53 of FIG. 7 but has an additional optical fiber 57P. The optical fiber 57P can be any optical fiber described before. The shaft 53P also has an optical directing element 59P for example a mirror attached to the shaft body with the mounting tube 67. The directing element 59P projects the optical energy 55P to tissue regions substantially overlapped with a region 56P where the ultrasound transducer 65 can effectively collect ultrasound transients. The sheath 54P is similar to the sheath 54 of FIG. 7 but is made of material at least partially substantially transparent for both acoustic and optical energies. Pebax is one example of such material. For this embodiment, the rotary join 107 is a combined optical and electrical rotary joint commercially available for example from Princetel, N.J.

Figure 20B:
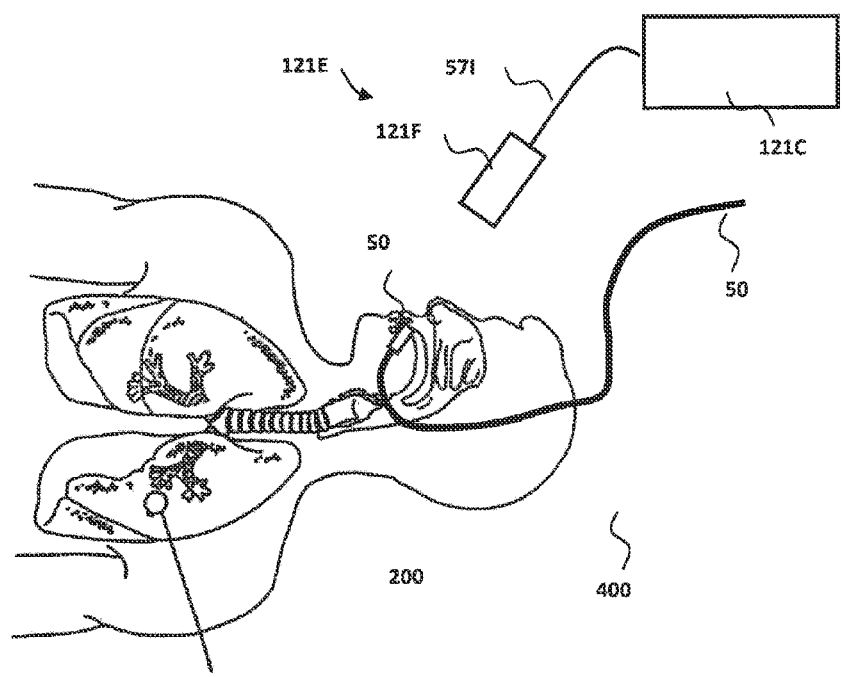

In an alternative embodiment shown in FIG. 20B, the optical energy from the excitation source 121C illuminates the lumen wall tissue from outside of the patient 400, through the patient skin, and is delivered by an illuminating fixture 121E. The illumining fixture 121E can be in the form of an optical fiber 57I with a diffusing element 121F such as defocusing lens. In this case the probe 50 is identical to the probe 50 of FIG. 13 simplifying the probe design. The disadvantage of this embodiment is higher optical power required to produce detectable ultrasound transients.

In both embodiments of FIGS. 20A and 20B the optical energy will not be focused in the illuminated region but will be spread due to large multiple scattering of optical radiation in tissue. However, the ultrasound resolution will be free of the scattering limitations. By using signal processing algorithms such as back projection algorithms described by Mingua Hu et al in *Review of Scientific Instruments* 77, 04101(206) for analysis of the ultrasound transients, the spatial resolution of absorption coefficient mapping can be made significantly better than limits imposed by light scattering. Specifically, spatial resolution can be made on the order of the acoustic wavelength generated by the light absorption and then detected by the transducer 65, which can be few hundred micrometers or better. By obtaining absorption coefficient mapping at several wavelengths, for example by using a wavelength tunable time varying optical source or by using a plurality of the time varying optical sources of different wavelengths, concentration of chromophores can be obtained as described above. As a result hemoglobin concentration and blood oxygenation can be determined.

Additional advantage of this method is ability to use exogenous contrast agents that preferentially attach to specific tissue type and selectively absorb optical energy. Such contrast agents can be for example nanomaterials such as gold nano-particles.

The drawback of the embodiments shown in FIG. 20A and FIG. 20B is that the use of these embodiments requires imaging contact with respect to the tissue, and the probe structure may be complicated. These embodiments can be improved as described below. An alternative arrangement for mapping the chromophores concentration free of the limitations of the embodiments of FIGS. 20A and 20C is shown in FIG. 21A. In FIG. 21A the optical source 121 is coupled to the interferometer 130 or 130A described before. The imaging optical energy 55 from the source 121 is directed to the probe 50 via the drive unit 101. Also there is the transients excitation optical source 121C of wavelengths that can be absorbed by the chromophores to be analyzed. For example a tunable pulse laser source in the vicinity of $\lambda_1$ $\lambda_2$ $\lambda_3$ wavelengths of FIG. 19A, or two separate pulsed lasers with $\lambda_1$ and $\lambda_3$ wavelengths can be used for analysis of HHb and HbO2 concentrations. Alternatively, a chirp modulated CW laser or lasers with several wavelengths can be used. The excitation source 121C and the imaging source 121 are in communications at least for some embodiments of the imaging apparatus 150 in this embodiment. For example the sweeping frequency of the swept source 121 and the repetition rate of the excitation transients from the source 121C can be synchronized. The light from the excitation source 121C is directed to the Drive Unit 101 and then to the probe 50 via and an WDM, or cladding mode coupler 125A. At the distal end of the probe 50, excitation optical energy 55P from the excitation source 121C substantially overlaps with the imaging optical energy 55 from the imaging source 121 so that there is a locality 56P in the tissue from where returned imaging optical energy 55 is changed by acoustic transients generated by the excitation optical energy 55F absorption by the tissue chromophores. The changes in the returned imaging optical energy manifest themselves via changed in the interferogram produced by the interferometer 130 or 130A as will be described in more details further below. The interferogram is detected by the receiver 136, digitized by the A/D converter 142, pre-amplified and filtered by the electronics module 141 and then processed by the CPU 140 similarly to arrangements described before. The arrangement of FIG. 2A can be also easily adapted for navigation in luminal structures by employing absorption contrast between lumen wells and media fill the lumen interior. For example, when the luminal network includes the airway tree, the difference in absorption between water in the tissue and air in the lumen can be used. Also this arrangement can be easily adapted to map absorptive features without generating acoustic transient instead having the returned imaging optical energy 55 changed by local heating and thermal expansion.

Turning attention to distal end arrangements of the shaft 53 for the probe 50 of FIG. 21A, FIGS. 21B and 21C show exemplary arrangements that allow overlapping illumination of the tissue with the excitation and imaging optical energy.

In FIG. 21B, the imaging optical energy 55 and the excitation optical energy 55P are delivered to the distal end via the same core of the optical fiber 57B that can be any optical fiber described previously. In FIG. 21B, the imaging optical energy 55 and the excitation optical energy 55P also have different wavelengths and therefore can be separated at the distal end of the probe by means of a WDM prism 59P that directs the excitation optical energy toward the tissue while transmitting the imaging optical energy. Such WDM prisms are commonly used in the telecom industry. A GRIN lens 58A1 and a GRIN lens 58A2 and the reflective prism 59B allow independent focusing and directing of the imaging optical energy 55 and the excitation optical energy 55P so that the sensing region 56P can be formed. For this embodiment, the shaft 53 is further enclosed in the transparent sheath 54 described before (not shown) and the DU 101 of FIG. 21B employs standard SM FORJ. In alternative embodiment shown in FIG. 21C, a dual clad fiber (DCF) 57P is used as the waveguide of the probe shaft 53 so that the imaging optical energy 55 is coupled to the core of the dual clad fiber 57P while the excitation optical energy 55P is coupled to the cladding mode of the DCF 57P. The imaging optical energy can be at least partially focused by the GRIN lens 58A or any other focusing element described before. Both the imaging optical energy 55 and the excitation optical energy 55P can be directed to the tissue by the same directing element described before for example by the prism 59B ensuring overlap and formation of the sensing region 56P in the tissue. The probe shaft 53 is also enclosed in the sheath 54 in this arrangement (not shown). In this arrangement the Drive Unit 101 of FIG. 21B employs FORJ that use the DCF and the cladding mode coupler 125A can be realized by removing second clad from DCF in one location and coupling light from any fiber in to the first clad of DCF in that location.

FIG. 22 shows exemplary A-lines signal processing steps that allows extraction of acoustic transients for the case of the FD-OCT. In this case, the repetition rate of the excitation source 121C is smaller than the sweeping rate of the swept source 121. For example if the repetition rate is half of the sweeping rate, one half of the A-lines are affected by the acoustic transients while the other half is not affected. Analysis of the difference between affected and non-affected A-lines allows extraction of the acoustic transients. Specifically, a digitized waveform 128 of a n-th A-line $V_n[t_m]$ is digitally FFT transformed 128A then multiplied by a Heaviside function 128B. Then a tracking maximum 128C of the FFT transform is determined, that is the maximum of the FFT transform of the n-th A-line that uses the value and locations of maxima determined from the previous (n−1) A-line to improve robustness to outliers of the maximum search algorithm. The location of maximum is used to determine location of the center of the adaptive bandwidth filter 128D. The output of the adaptive bandwidth filter is inversely Fourier transformed 128E to produce the processed complex waveform A-line $\tilde{V}_n[t_m]$ that contains the tissue interferometric response around the maximum. Steps 128A through 128E are then repeated for the next, n+1 A-line and phase difference 129A or magnitude difference 129B between n+1-th and i line is estimated as a function of time. The phase and/or magnitude difference is proportional to acoustic transients and therefore photoacoustic images can be constructed for example, using processing steps described by Mingua Hu et al in *Review of Scientific Instruments* 77, 04101(206) once the steps 129A and/or 129B are performed. The frequency shifts induced by the acoustic transients can be estimated in the step 129A using the Kasai autocorrelation function. The Kasai autocorrelation function measures phase shifts between two adjacent A-line and is shown in the next equation $$\Delta\varphi = \arctan\left\{\frac{\sum_{m=1}^{M}\sum_{n=1}^{N-1}(I_{n+1}[m]Q_n[m] - Q_{n+1}[m]I_n[m])}{\sum_{m=1}^{M}\sum_{n=1}^{N-1}(I_{n+1}[m]Q_n[m] + Q_{n+1}[m]I_n[m])}\right\}$$

Here, M and N define the size of the averaging mask used to improve signal-to-noise ratio. The magnitude changes induced by the acoustic transients in the step 129B can be estimated using the following algorithm $$\Delta\langle S^2\rangle = \sum_{m=1}^{M}\sum_{n=1}^{N-1}(I_{n+1}^2[m] - I_n^2[m] + Q_{n+1}^2[m] - Q_n^2[m])$$

References throughout this specification have been made to "one embodiment," "an embodiment," "a related embodiment," or similar language. Such references mean that a particular feature, structure, or characteristic described in connection with the referred to "embodiment" is included in at least one embodiment of the present invention. Thus, appearances of the phrases "in one embodiment," "in an embodiment," and similar language throughout this specification may, but do not necessarily, all refer to the same implementation of the inventive concept. It is to be understood that no portion of disclosure, taken on its own and in possible connection with a figure, is intended to provide a complete description of all features of the invention.

It is to be understood that no single drawing used in describing embodiments of the invention is intended to support a complete description of all features of the invention. In other words, a given drawing is generally descriptive of only some, and generally not all, features of the invention. A given drawing and an associated portion of the disclosure containing a description referencing such drawing do not, generally, contain all elements of a particular view or all features that can be presented is this view, for purposes of simplifying the given drawing and discussion, and to direct the discussion to particular elements that are featured in this drawing. A skilled artisan will recognize that the invention may possibly be practiced without one or more of the specific features, elements, components, structures, details, or characteristics, or with the use of other methods, components, materials, and so forth. Therefore, although a particular detail of an embodiment of the invention may not be necessarily shown in each and every drawing describing such embodiment, the presence of this detail in the drawing may be implied unless the context of the description requires otherwise. In other instances, well known structures, details, materials, or operations may be not shown in a given drawing or described in detail to avoid obscuring aspects of an embodiment of the invention that are being discussed. Furthermore, the described single features, structures, or characteristics of the invention may be combined in any suitable manner in one or more further embodiments.

The invention as recited in claims appended to this disclosure is intended to be assessed in light of the disclosure as a whole, including features disclosed in prior art to which reference is made.

At least some elements of a device of the invention can be controlled, in operation with a processor governed by instructions stored in a memory such as to enable desired operation of these elements and/or system or effectuate the flow of the process of the invention. The memory may be random access memory (RAM), read-only memory (ROM), flash memory or any other memory, or combination thereof, suitable for storing control software or other instructions and data. Those skilled in the art should also readily appreciate that instructions or programs defining the functions of the present invention may be delivered to a processor in many forms, including, but not limited to, information permanently stored on non-writable storage media (e.g. read-only memory devices within a computer, such as ROM, or devices readable by a computer I/O attachment, such as CD-ROM or DVD disks), information alterably stored on writable storage media (e.g. floppy disks, removable flash memory and hard drives) or information conveyed to a computer through communication media, including wired or wireless computer networks. In addition, while the invention may be embodied in software, the functions necessary to implement the invention may optionally or alternatively be embodied in part or in whole using firmware and/or hardware components, such as combinatorial logic, Application Specific Integrated Circuits (ASICs), Field-Programmable Gate Arrays (FPGAs) or other hardware or some combination of hardware, software and/or firmware components.

While the invention is described through the above-described exemplary embodiments, it will be understood by those of ordinary skill in the art that modifications to, and variations of, the illustrated embodiments may be made without departing from the disclosed inventive concepts. Furthermore, disclosed aspects, or portions of these aspects, may be combined in ways not listed above. Accordingly, the invention should not be viewed as being limited to the disclosed embodiment(s).

What is claimed is:

1. A multi-view imaging probe configured to image a tissue, the probe comprising:
    an elongated flexible body having a proximal end portion, an opposite distal end portion, a longitudinal axis, and an outer wall extending from the proximal end portion to the distal end portion, the wall having at least a portion that is at least partially transparent to light used for imaging by the probe;
    an optical waveguide extended inside the flexible body to support optical communication between the proximal and distal ends;
    a first beam-directing element disposed at the distal end in optical communication with the optical waveguide; the first beam directing element configured to be continuously rotatable to scan the tissue through the at least a portion of the outer wall with the light emitted from the optical waveguide and redirected by the first directing element to define a rotating scanning beam that forms a side field-of-view (FOV) within a first angular range;
    at least one second beam-directing element configured to remain immovable with respect to the distal end during imaging of the tissue with the probe and disposed at the flexible body to intersect a portion of light emitted from the optical waveguide and transmitted through the first beam-directing element and redirect said portion to form a forward FOV of the imaging probe within a second angular range;
    wherein the first angular range is defined outside a range of −45 degrees to 45 degrees with respect to the longitudinal axis; and wherein the second angular range is defined within the range of −45 degrees to 45 degrees with respect to the axis.

2. A multi-view imaging probe according to claim 1, further comprising a steering mechanism disposed in the flexible body and configured to deflect the distal end and rotate the distal end around the longitudinal axis, wherein the steering mechanism includes a pull wire extended in the flexible body.

3. A multi-view imaging probe according to claim 1, further comprising a steering mechanism disposed in the flexible body and configured to deflect the distal end and rotate the distal end around the longitudinal axis, wherein the steering mechanism incorporates a shape memory element disposed at the distal end and in thermal contact with a portion of the flexible body, the shape memory element configured to change its shape when said portion of the flexible body is heated by imaging energy delivered by the energy guide.

4. A multi-view imaging probe according to claim 1, further comprising a steering mechanism disposed in the flexible body and configured to deflect the distal end and rotate the distal end around the longitudinal axis, wherein the steering mechanism incorporates a tubular element configured to be either slideable coaxially over the flexible body or slideable within a lumen inside the flexible body.

5. A multi-view imaging probe comprising:
    an elongated flexible body having
        proximal and distal ends,
        a longitudinal axis,
        a side surface extending from the proximal end to the distal end, the side surface being at least partially transparent to light used for imaging by the probe, and
        a transparent cap containing a plurality of optical elements immovably affixed to one another and to the flexible body, wherein said plurality includes an optical lens element having a first axis;
    an optical waveguide inside the flexible body and configured to support optical communication between the proximal and distal ends;
    a beamsplitting element inside the flexible body and appended to the optical waveguide at the distal end to redirect a first portion of light delivered along the optical waveguide to the distal end transversely with respect to the longitudinal axis through the side surface to form a first beam of light while transmitting a second portion of said light inside the flexible body along the axis towards and through the transparent cap to form a second beam of light, the beamsplitting element configured to be continuously rotatable about a chosen axis.

6. An imaging probe according to claim 5, wherein said plurality of optical elements include a second optical lens element having a second axis that is laterally offset with respect to the first axis such as to shape the second beam of light as a non-rotationally-symmetric cone.

7. An imaging probe according to claim 5, further comprising a steering mechanism disposed in the flexible body and configured to deflect the distal end and rotate the distal end around the longitudinal axis, wherein the steering mechanism incorporates a shape memory element disposed at the distal end and in thermal contact with a portion of the flexible body, the shape memory element configured to change its shape when said portion of the flexible body is heated by light delivered by the optical waveguide.

8. An imaging probe according to claim 5, wherein the first and second portions of light are different in either spectral content or polarization.

9. An imaging probe according to claim 5, wherein said optical lens element is configured to focus light only in one dimension.

10. An imaging probe according to claim 5, wherein the plurality of optical elements includes at least one optical prism located to receive said second portion from the beamsplitting element and configured such as to make a solid angle subtended by the second beam outside the transparent cap smaller than a solid angle subtended by the second portion received from the beamsplitting element.

11. An imaging probe according to claim 5, further comprising steering mechanism disposed in the flexible body and configured to deflect the distal end and rotate the distal end around the longitudinal axis, wherein the steering mechanism incorporates a tubular element configured to be either slideable coaxially over the flexible body or slideable within a lumen inside the flexible body.

12. An imaging probe according to claim 5, further comprising
   a steering mechanism disposed in the flexible body and configured to deflect the distal end and rotate the distal end around the longitudinal axis, wherein the steering mechanism includes a pull wire extended in the flexible body.

13. A method for collecting optical information with the use of a multi-view imaging probe having an axis, a side surface, proximal and distal ends, and a transparent cap disposed across the axis at the distal end, the method comprising:
   i) redirecting a first portion of light, delivered by an optical waveguide enclosed by the side surface, by a beamsplitting element along a first direction through the side surface to form a first beam of light that defines a sideway field-of-view (FOV) of the probe within a first angular range
      while transmitting a second portion of said light through the beamsplitting element along the axis towards the transparent cap, the transparent cap containing a plurality of optical elements immovably affixed to one another;
      wherein the beamsplitting element is enclosed by the side surface at the distal end,
      wherein the first direction is transverse to the axis;
   ii) transmitting the second portion of light through said plurality of optical elements that are immovably disposed with respect to the distal end at the imaging probe and further through the transparent cap along a second direction to form a second beam of light that defines a forward FOV of the probe within a second angular range, the second direction being inclined to the axis;
   iii) repositioning the distal end with respect to a target to receive, by the optical waveguide, first light reflected by the target illuminated with the first beam in the sideway FOV and second light reflected by the target illuminated with the second beam in the forward FOV;
   iv) with the use of an imaging console containing a processor, operably cooperated with the distal end, forming a 3D forward image data of the target with the use of the first light, and
      tracking position and angular orientation of the distal end by using image data of the tissue acquired from the second light,
wherein said tracking position and angular orientation is based on cross-correlation of the image data of the tissue acquired from the second light in the sideway FOV,
wherein said cross-correlation uses image data acquired with the probe in the sideway FOV provided by the imaging console that is configured to generate image data based on OCT.

14. A method according to claim 13, further comprising steering the distal end by pulling a slideable wire extended in the probe flexible body and attached to the distal end.

15. A method according to claim 13, further comprising steering of the distal end by changing a shape of a shape memory element disposed at the distal end in thermal contact with at least one portion of the distal end by heating said portion with light delivered by the optical waveguide.

16. A method according to claim 13, further comprising sliding the flexible body inside a tubular element and flexing the tubular element.

17. A method according to claim 13, further comprising spatially spreading the second beam in the forward FOV
   with a spectrally-dispersive element of said plurality of optical elements, and
   with said imaging console, generating 3D image data of the target in the forward FOV based on decoding of spectrally encoded light reflected from the tissue illuminated with a spatially spread second beam.

18. A method according to claim 13, further comprising rotating the beamsplitting element continuously while steering the distal end to scan the second beam of light in a first scanning pattern with respect to the target.

19. A method according to claim 18, further comprising remapping the first scanning pattern to a circular pattern based on an instant angular velocity, of the beamsplitting element, that has been estimated from the first light collected by the probe in a sideway FOV.

20. An imaging system configured to image a tissue, the system comprising:
   an imaging probe having
      an elongated flexible body having a proximal end, an opposite distal end, a longitudinal axis, and an outer wall extending from the proximal end to the distal end, said outer wall having at least a portion which is at least partially transparent to imaging energy used for imaging by the probe;
      an optical waveguide extended inside the flexible body and configured to deliver light between the proximal end and the distal end;
      a beam-directing element disposed within the outer wall at the distal end in optical communication with the optical waveguide, the beam-directing element configured to be continuously rotatable to scan the tissue through the at least a portion of the outer wall with light received from the optical waveguide to form a beam that defines a field-of-view (FOV) of the probe within an angular range; and
      an optical element configured to be rotatable together with the beam-directing element and disposed to spatially-spread said beam at any spectral component thereof, in the FOV across the tissue, to introduce different Doppler shifts in light of a spatially-spread beam reflected from different locations at the tissue to form Doppler-encoded reflected light; and an imaging console, including a data-processing unit, in operable communication with the imaging probe and configured
  to process imaging energy acquired by the probe to generate image data based on optical coherence tomography (OCT), and
  to generate 3D image data of tissue in the FOV based on decoding the Doppler encoded reflected light.

* * * * *